US008609632B2

(12) United States Patent
Shriver et al.

(10) Patent No.: US 8,609,632 B2
(45) Date of Patent: Dec. 17, 2013

(54) LOW MOLECULAR WEIGHT HEPARIN COMPOSITION AND USES THEREOF

(75) Inventors: Zachary Shriver, Cambridge, MA (US); Mallikarjun Sundaram, Randolph, NJ (US); Ganesh Venkataraman, Bedford, MA (US); Pat Oliver-Shaffer, Acton, MA (US); Yiming Yao, West Newton, MA (US); Zainab Sirajbhai Mamuwala, Lowell, MA (US); Ian David Fier, Southborough, MA (US); Yiwei Qi, Andover, MA (US); Ishan Capila, Ashland, MA (US); Nur Sibel Gunay, Brookline, MA (US); Daniela Beccati, Brighton, MA (US); Cuihua Liu, Belmont, MA (US); Corinne Bauer, Sudbury, MA (US); Ying Li, Wellesley, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 167 days.

(21) Appl. No.: 11/805,829

(22) Filed: May 24, 2007

(65) Prior Publication Data
US 2007/0287683 A1 Dec. 13, 2007

Related U.S. Application Data

(60) Provisional application No. 60/809,136, filed on May 25, 2006, provisional application No. 60/849,578, filed on Oct. 4, 2006, provisional application No. 60/849,628, filed on Oct. 5, 2006.

(51) Int. Cl.
*A61K 31/727* (2006.01)
*A61K 31/715* (2006.01)
*A01N 43/04* (2006.01)

(52) U.S. Cl.
USPC ............................................. 514/56; 514/54

(58) Field of Classification Search
USPC ..................................................... 514/56, 54
See application file for complete search history.

(56) References Cited

U.S. PATENT DOCUMENTS

| | | | |
|---|---|---|---|
| 5,707,973 A | 1/1998 | Baron et al. | |
| 5,721,357 A | 2/1998 | Baron et al. | |
| 5,744,457 A | 4/1998 | Weitz et al. | |
| 5,763,427 A | 6/1998 | Weitz et al. | |
| 5,849,721 A | 12/1998 | Uzan | |
| 6,075,013 A | 6/2000 | Weitz et al. | |
| 6,608,042 B2* | 8/2003 | Mourier et al. | 514/54 |
| 6,869,789 B2 | 3/2005 | Liu et al. | |
| 6,969,705 B2 | 11/2005 | Pecquet et al. | |
| 7,008,933 B2 | 3/2006 | Welzel | |
| 7,575,886 B2 | 8/2009 | Venkataraman et al. | |
| 2001/0046974 A1 | 11/2001 | Weitz et al. | |
| 2002/0009782 A1 | 1/2002 | Miron | |
| 2003/0050802 A1 | 3/2003 | Jay et al. | |
| 2003/0092671 A1 | 5/2003 | Johansen et al. | |
| 2003/0099628 A1 | 5/2003 | Liu et al. | |
| 2003/0134823 A1 | 7/2003 | Welzel | |
| 2003/0203385 A1* | 10/2003 | Venkataraman et al. | 435/6 |
| 2006/0067928 A1 | 3/2006 | Liu et al. | |
| 2006/0182734 A1 | 8/2006 | Liu et al. | |
| 2006/0183713 A1 | 8/2006 | Liu et al. | |
| 2006/0205662 A1 | 9/2006 | Armstrong et al. | |
| 2007/0092507 A1 | 4/2007 | Balthasar et al. | |
| 2007/0248981 A1 | 10/2007 | Snider et al. | |
| 2007/0287683 A1 | 12/2007 | Shriver et al. | |

FOREIGN PATENT DOCUMENTS

| | | |
|---|---|---|
| EP | 0244236 | 11/1987 |
| EP | 625166 B1 | 10/1997 |
| EP | 1252194 B1 | 10/2004 |
| JP | S62-283103 | 12/1987 |
| JP | 4226101 | 8/1992 |
| JP | 07-503496 | 4/1995 |
| JP | 09-510736 | 10/1997 |
| JP | 2003-504428 | 2/2003 |
| JP | 2004-504451 | 2/2004 |
| RU | 2005105423 | 8/2006 |
| WO | 9316112 | 8/1993 |
| WO | 98/55515 | 12/1998 |
| WO | 01002443 | 1/2001 |
| WO | 0151525 A1 | 7/2001 |
| WO | 01/02443 | 11/2001 |
| WO | 02/08295 | 1/2002 |
| WO | 0223190 | 3/2002 |
| WO | 03078960 | 9/2003 |
| WO | 2004/033503 | 4/2004 |
| WO | 2005/010051 | 2/2005 |
| WO | 2007140231 A2 | 12/2007 |

OTHER PUBLICATIONS

Fareed, J., Hoppensteadt, D., Schultz, C., Ma, Q., Kujawski, M.F., Messmore, H. (2004) Biochemical and Pharmacologic Heterogeneity in Low Molecular Weight Heparins. Impact on the Therapeutic Profile. Current Pharmaceutical Design, vol. 10, p. 983-999.*
Shriver, Z., Sundaram, M., Venkataraman, G., Fareed, J., Linhardt, R., Biemann, K., Sasisekharan, R. (2000) Cleavage of the antithrombin III binding site in heparin by heparinases and its implication in the generation of low molecular weight heparin. Proceedings of the National Academy of Sciences, vol. 97, No. 19, p. 10365-10370.*
Crowther et al., "Mechanisms Responsible for the Failure of Protamine to Inactive Low-Molecular-Weight Heparin", British Journal of Haematology, vol. 116, pp. 178-186, 2002, Great Britain.
Maddineni et al., "Relative Neutralization of the Biological Actions of Sulfaminoheparosans (K5 Derivatives) and Heparins by Protamine Sulfate", Clinical and Applied Thrombosis/Hemostasis, vol. 13, No. 1, pp. 52-64, Jan. 2007.

(Continued)

*Primary Examiner* — Scarlett Goon
(74) *Attorney, Agent, or Firm* — Lando & Anastasi LLP

(57) ABSTRACT

Preparations of low molecular weight heparins (LMWHs) having improved properties, e.g., properties that provide a clinical advantage, are provided herein. Methods of making and using such preparations as well as methods of analyzing starting materials, processing, intermediates and final products in the production of such LMWH preparations are provided.

12 Claims, 17 Drawing Sheets

(56) References Cited

OTHER PUBLICATIONS

Frampton et al., "Parnaparin A Review of its Pharmacology and Clinical Application in the Prevention and Treatment of Thromboembolic and Other Vascular Disorders", Drugs, vol. 47, No. 4, pp. 652-676, 1994.

Verli et al, "Molecular Dynamics Simulation of a Decasaccharide Fragment of Heparin in Aqueous Solution", Carbohydrate Research, vol. 339, pp. 281-290, 2004.

Lubineau et al., "Synthesis of Tailor-Made Glycoconjugate Mimetics of Heparan Sulfate That Bind IFN-γ in the Nanomolar Range", Chem. Eur. J., vol. 10., pp. 4265-4282, 2004.

Linhardt et al., "Analysis of Glycosaminoglycan-Derived Oligosaccharides Using Fast-Atom-Bombardment Mass Spectrometry", Carbohydrate Research, vol. 225, pp. 137-145, 1992.

Chai et al., "Characterisation by LSI-MS and H NMR Spectroscopy of Tetra-, and Octa-Saccharides of Porcine Intestinal Heparin", Carbohydrate Research, vol. 269, pp. 139-156, 1995.

Sundaram et al., Rational Design of Low-Molecular Weight Heparins with Improved In Vivo Activity , PNAS, vol. 100, No. 2, pp. 651-656, Jan. 21, 2003.

MacFarlane et al., "An Introduction to Low-Molecular-Weight Heparins and their Use in the Treatment of Deep Vein Thrombosis", American Journal of Therapeutics, vol. 2, pp. 569-580, 1995.

International Search Report mailed Oct. 10, 2008 for PCT Application PCT/US2007/069626.

Written Opinion mailed mailed Oct. 10, 2008 for PCT Application PCT/US2007/069626.

Glusa, E., et al., "Effects of a Supersulfated Low Molecular Weight Heparin (IK-SSH) on Different Hemostatic Parameters" Haemostasis, 1998;28:45-56.

Extended Search Report from European Application Serial No. 11172772.3 dated Dec. 18, 2012.

Kishimoto et al., "M118—a rationally engineered low-molecular-weight heparin designed specifically for the treatment of acute coronary syndromes", Thrombosis and Haemostasis, vol. 102, No. 5 pp. 900-906, (1999).

European Search Report from European Application Serial No. 10190250.0 dated Dec. 27, 2010.

Database CA, "Process for preparing low mol. wt. heparin", Dec. 15, 2004, CN 1554671.

Extended Search Report from European Application Serial No. 11172771.5 dated Feb. 22, 2012.

International Search Report mailed Nov. 19, 2010 for PCT Application PCT/US2010/49890.

Pangrazzi J et al., "Antithrombotic and bleeding effects of a low molecular weight heparin fraction", Biochemical Pharmacology, vol. 34, No. 18, p. 3305-3308, Sep. 15, 1985.

\* cited by examiner

US 8,609,632 B2

LOW MOLECULAR WEIGHT HEPARIN COMPOSITION AND USES THEREOF

This application claims priority to U.S. Provisional Application Ser. Nos. 60/809,136, filed, on May 25, 2006; 60/849,578, filed on Oct. 4, 2006; and 60/849,628, filed on Oct. 5, 2006, the contents of which are incorporated herein by reference.

BACKGROUND

Coagulation is a physiological pathway involved in maintaining normal blood hemostasis in mammals. Under conditions in which a vascular injury occurs, the coagulation pathway is stimulated to form a blood clot to prevent the loss of blood. Immediately after the vascular injury occurs, blood platelets begin to aggregate at the site of injury forming a physical plug to stop the leakage. In addition, the injured vessel undergoes vasoconstriction to reduce the blood flow to the area and fibrin begins to aggregate forming an insoluble network or clot, which covers the ruptured area.

When an imbalance in the coagulation pathway shifts towards excessive coagulation, the result is the development of thrombotic tendencies, which are often manifested as heart attacks, strokes, deep vein thrombosis, and acute coronary syndromes such as myocardial infarcts, and unstable angina. Furthermore, an embolism can break off from a thrombus and result in a pulmonary embolism or cerebral vascular embolism including stroke or transient ischemia attack. Current therapies for treating disorders associated with imbalances in the coagulation pathway involve many risks and must be carefully controlled.

Heparin and low molecular weight heparins (LMWHs), complex, sulfated polysaccharides isolated from endogenous sources, are potent modulators of hemostasis. Heparin, a highly sulfated heparin-like glycosaminoglycan (HLGAG) produced by mast cells, is a widely used clinical anticoagulant, and is one of the first biopolymeric drugs and one of the few carbohydrate drugs. Heparin and molecules derived from it are potent anticoagulants that are used in a variety of clinical situations, especially for thromboembolic disorders including the prophylaxis and treatment of deep venous thrombosis and pulmonary embolism, arterial thromboses, and acute coronary syndromes like myocardial infarction and unstable angina. Heparin and LMWHs interact with multiple components of the coagulation cascade to inhibit the clotting process. Heparin primarily elicits its effect through two mechanisms, both of which involve binding of antithrombin III (AT-III) to a specific pentasaccharide sequence, $H_{NAc/S,6S}GH_{NS,3S,6S}I_{2S}H_{NS,6S}$ contained within the polymer. First, AT-III binding to the pentasaccharide induces a conformational change in the protein that mediates its inhibition of factor Xa. Second, thrombin (factor IIa) also binds to heparin at a site proximate to the pentasaccharide/AT-III binding site. Formation of a ternary complex between AT-III, thrombin and heparin results in inactivation of thrombin. Unlike its anti-Xa activity that requires only the AT-III pentasaccharide-binding site, heparin's anti-IIa activity is size-dependent, in addition to the pentasaccharide unit responsible for anti-Xa activity for the efficient formation of an AT-III, thrombin, and heparin ternary complex. Heparin also mediates the release of tissue factor pathway inhibitor (TFPI) from endothelial cells. TFPI, a heparin cofactor, is a serine protease that directly binds to and inhibits factor X. TFPI is a potent anti-thrombotic, particularly when co-administered with heparin.

Although heparin is highly efficacious in a variety of clinical situations and has the potential to be used in many others, the side effects associated with heparin therapy are many and varied. Anti-coagulation has been the primary clinical application for unfractionated heparin (UFH) for over 65 years. Due to its erratic intravenous pharmacokinetics and lack of subcutaneous bioavailability, UFH has been administered by intravenous injection instead. Additionally, the application of UFH as an anticoagulant has been hampered by the many side effects associated with non-specific plasma protein binding with UFH.

This has led to the explosion in the generation and utilization of low molecular weight heparin (LMWH) as an efficacious alternative to UFH. LMWH provide a more predictable pharmacological action, reduced side effects, and better bioavailability than UFH. Since the commercially available LMWH preparations are not fully neutralized by protamine, an unexpected reaction could have extremely adverse effects; the anti-Xa activity of enoxaparin and other LMWH are neutralizable only to an extent of about 40% with ≤2 mg Protamine/100 IU anti-Xa LMWH. The anti-IIa activity is neutralizable only to an extent of about 60% with ≤2 mg Protamine/100 IU anti-Xa LMWH. (On the other hand, the anti-Xa and anti-IIa activity of UFH is neutralizable almost completely (>90%) with ≤3 mg Protamine sulfate/100 IU anti-Xa UFH.)

Pharmaceutical preparations of these polysaccharides, typically isolated from porcine intestinal mucosa, are heterogeneous in length and composition. As such, only a portion of a typical preparation possesses anticoagulant activity. At best, the majority of the polysaccharide chains in a pharmaceutical preparation of heparin or LMWH are inactive, at worst, these chains interact nonspecifically with plasma proteins to elicit the side effects associated with heparin therapy. Therefore, it is important to develop novel LMWHs that retain the anticoagulant activity and other desired activities of UFH but have reduced side effects. LMWHs, essentially due to their reduced chains sizes and dispersity, display markedly less non-specific plasma protein binding. However, all LMWHs that are currently clinically available also possess reduced anti-IIa activity as compared to UFH. Because of this decreased activity, a larger dose of LMWH is required (compared to UFH) in order to achieve a similar anti-Xa and anti-IIa activity, and the standard tests for UFH activity, activated partial thromboplastin time (aPTT) or activated clotting time (ACT), are not useful as they rely primarily on anti-IIa activity for a readout. The most widely used test for monitoring LMWH levels is an anti-Xa activity test, which depends on the subject having sufficient levels of antithrombin III (ATIII), which is not always the case. This test is quite costly (well over $100.00) and is not routine or readily available, as samples generally must be sent to an outside lab for analysis. Consequently, the use of LMWHs so far has been largely limited to the prevention of thrombosis and not to their treatment, and the population of patients to whom it can be administered has been limited, excluding, among others, pediatric patients, patients with abnormal renal function as measured by RFI, urea, creatinine, phosphorus, glomerular filtration rate (GFR), or BUN (Blood Urea Nitrogen level) in blood and urine and the interventional cardiology patient population.

SUMMARY OF THE INVENTION

The invention is based, in part, on the development of preparations of LMWHs having, e.g., designed to have, improved properties, e.g., properties that provide a clinical advantage. Such functional properties include, by way of example, one or more of: reversibility in response to protamine sulfate; predictable or otherwise improved pharmacokinetics; improved anti-IIa activity, as compared, e.g., to enoxaparin; a relatively constant anti-Xa activity to anti-IIa activity ratio over a period of about 30 to 180 minutes; monitorable activity levels; subcutaneous bioavailability; and reduced likelihood of causing heparin induced thrombocytopenia (HIT). LMWHs disclosed herein can also have structural characteristics that distinguish them from other commercially available LMWHs. For example, a LMWH preparation provided herein can have one or more of the following characteristics: substantially undetectable linkage region; an increased amount of 3-O sulfates as compared to commercially available LMWH preparations; a subset of the chains have an unsulfated ΔU at the non-reducing end; a subset of the chains, e.g., a majority, e.g., substantially all of the chains, have an N-acetylated hexosamine at the reducing end; a ratio of $\Delta UH_{NAc,6S}GH_{NS,3S,6S}$ to $\Delta U_{2S}H_{NS,6S}IH_{NAc,6S}GH_{NS,3S,6S}$ of about 1:1 to 4:1 (e.g., about 1:1, 2:1, 3:1, 4:1), and substantially no modified reducing end structures. The invention includes LMWH preparations having one or more of these properties and characteristics as well as methods of making and using such preparations. The invention also features methods of analyzing starting materials, processing, intermediates and final products in the production of such LMWH preparations.

Accordingly, in a first aspect, the invention features, a LMWH composition having: a weight average molecular weight of about 5000 to 9000 Da, e.g., about 5000 to 8300 Da, e.g., about 5500 to 8000 Da, e.g., about 5700 to 7900 Da, e.g., about 5800 to 6800 Da; and an anti-IIa activity of about 50 to 300, e.g., about 70 to 280, e.g., about 90 to 250 IU/mg, e.g., about 100 to 250 IU/mg, e.g., about 100 to 140 IU/mg, 150 to 200 IU/mg, about 130 to 190 IU/mg, e.g., about 155 to 195 IU/mg.

In a second aspect, the invention features, a LMWH composition having:

a weight average molecular weight of about 5000 to 9000 Da, e.g., about 5000 to 8300 Da, e.g., about 5000 to 8000 Da, about 5500 to 8000 Da, e.g., about 5700 to 7900 Da, e.g., about 5800 to 6800 Da; and anti-IIa activity that is at least 50%, 60%, 70%, 80%, 85%, 90%, 95%, 99% or 100% neutralizable with protamine, e.g., as measured by activated partial thromboplastin time (ACT) or activated partial thromboplastin time (aPTT). Preferably, the anti-IIa activity of the LMWH is neutralized by at least 50%, 60%, 70%, 80%, 85%, 90%, 95%, 99% or 100% within 5, 10, 15, 30 minutes after protamine administration.

In a third aspect, the invention features, a LMWH composition having:

a weight average molecular weight of about 5000 to 9000 Da, e.g., about 5000 to 8300 Da, e.g., about 5500 to 8000 Da, e.g., about 5700 to 7900 Da, e.g., about 5800 to 6800 Da; and $\Delta UH_{NAc,6S}GH_{NS,3S,6S}$ is 5 to 15%, e.g., 7 to 14%, e.g., 9 to 12%, of the composition, e.g., as measured by mole %. Preferably the $\Delta UH_{NAc,6S}GH_{NS,3S,6S}$ at the non-reducing end of the molecule of about 5 to 15%, e.g., 7 to 14%, e.g., 9 to 12%, of the chains in the composition, e.g., as measured by mole %.

In a fourth aspect, the invention features, a LMWH composition having:

an average chain length of about 9 to 18 disaccharides or 8 to 18 disaccharides, e.g., about 9 to 16 or 8 to 16 disaccharides; and $\Delta UH_{NAc,6S}GH_{NS,3S,6S}$ is 5 to 15%, e.g., 7 to 14%, e.g., 9 to 12%, of the composition, e.g., as measured by mole %. Preferably the $\Delta UH_{NAc,6S}GH_{NS,3S,6S}$ at the non-reducing end of the molecule of about 5 to 15%, e.g., 7 to 14%, e.g., 9 to 12%, of the chains in the composition, e.g., as measured by mole %.

In a fifth aspect, the invention features, a LMWH composition having:

a weight average molecular weight of 5000 to 9000 Da, e.g., about 5000 to 8300 Da, e.g., about 5500 to 8000 Da, e.g., about 5700 to 7900 Da, e.g., about 5800 to 6800 Da; and an anti Xa to anti-IIa ratio of 3:1 or less, e.g., 2:1, e.g., 1.6:1, 1.5:1, 1.4:1, 1.3:1, 1.2:1, 1.1:1, 1:1 or 0.5:1.

Preferably, the anti-Xa to anti-IIa ratio remains relatively constant over the course of an administration of the LMWH preparation, e.g., the anti-Xa to anti-IIa ratio varies no more than about ±1.5, ±1, ±0.5, or ±0.2, over a period of about 30, 60, 120, 180, 240, 300 minutes. For example, if an initial ratio of anti-Xa activity to anti-IIa activity is 2, then the ratio measured at a second time (e.g., 30, 60, 120, 180, 240, 300 minutes) after the initial administration will preferably be less than 3, and preferably at or around 2.

In a seventh aspect, the invention features, a LMWH composition having:

optionally, a weight average molecular weight of about 5000 to 9000 Da, e.g., about 5000 to 8300 Da, e.g., about 5500 to 8000 Da, e.g., about 5700 to 7900 Da, e.g., about 5800 to 6800 Da; and when analyzed by digestion with heparinase I, heparinase II and heparinase III and capillary electrophoresis, each of peaks 1-14 of Table 10A is present.

In a preferred embodiment: the amount of each peak in the LMWH composition, as analyzed by digestion with heparinase I, heparinase II and heparinase III and capillary electrophoresis is about that found in Table 10A, the amount of each peak is within a range provided in Table 10A; the amount of peaks 10 and 11 are within a range provided in Table 10A.

In an eighth aspect, the invention features, a LMWH composition having:

optionally, a weight average molecular weight of about 5000 to 9000 Da, e.g., about 5000 to 8300 Da, e.g., about 5500 to 8000 Da, e.g., about 5700 to 7900 Da, e.g., about 5800 to 6800 Da; and when analyzed by 2D nuclear magnetic resonance (NMR) protons for each of the structures of Table 11A are present.

In a preferred embodiment: the amount of each of the structures in the LMWH composition, as analyzed by 2D NMR is about that found in Table 11A.

In a ninth aspect, the invention features a LMWH composition having one or more of the following characteristics:

the composition has substantially no (e.g., at least 85%, 90%, 95% or more of the chains do not have) modified reducing end structures; at least 60%, 70%, 80%, 85%, 90%, 95%, 99% of the chains of the composition have $H_{NAc}$ at the reducing end; less than 90%, 95%, 98%, 99%, preferably none of the chains of the composition have a sulfated ΔU at the non-reducing end; there is substantially no linkage region (e.g., less than 0.1% linkage region) present in the composition; the composition has more chains with 3-O sulfates than commercially available LMWHs, e.g., enoxaparin or dalteparin; and the ratio of $\Delta UH_{NAc,6S}GH_{NS,3S,6S}$ to $\Delta U_{2S}H_{NS,6S}IH_{NAc,6S}GH_{NS,3S,6S}$ in the composition is about 1:1 to 4:1.

In one embodiment, the composition has two, three, four, five or all of these characteristics.

In a tenth aspect, the invention features a LMWH composition having the following structure:

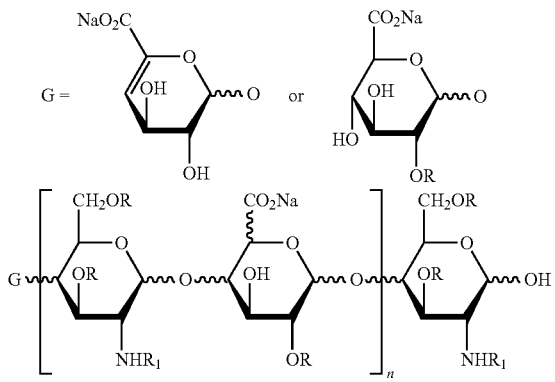

wherein R is H or SO₃X;

R1 is SO₃X or COCH₃;

X is a monovalent or divalent cation;

n=2-50, e.g., 2-40; and the composition preferably has an average value for n of 9-16, 8-16 or 8-15.

In one embodiment, the LMWH composition has the following structure:

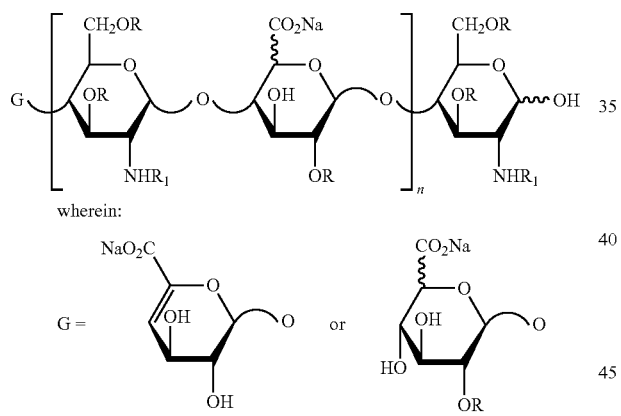

R is H or SO₃X;

R1 is SO₃X or COCH₃;

X is a monovalent or divalent cation;

n=2-50, e.g., 2-40; and the composition preferably has an average value for n of 9-16, 8-16 or 8-15.

In an eleventh aspect, the invention features, a LMWH composition having the following structure:

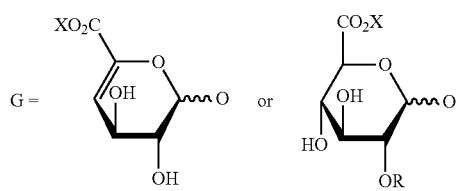

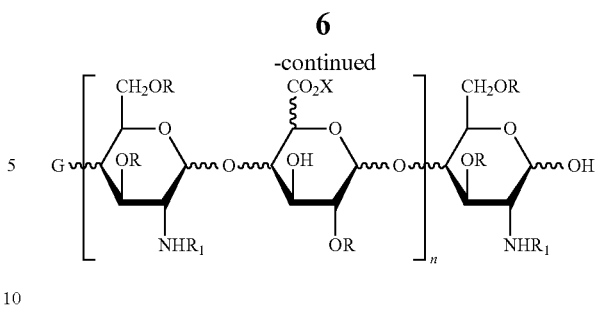

wherein X is Na or Ca, R is H or SO₃Na;

R1 is SO₃Na or COCH₃;

n=2-45, e.g., 2-35; and the composition preferably has an average value for n of 7-11 or 8-12.

In one embodiment, the LMWH composition has the following structure:

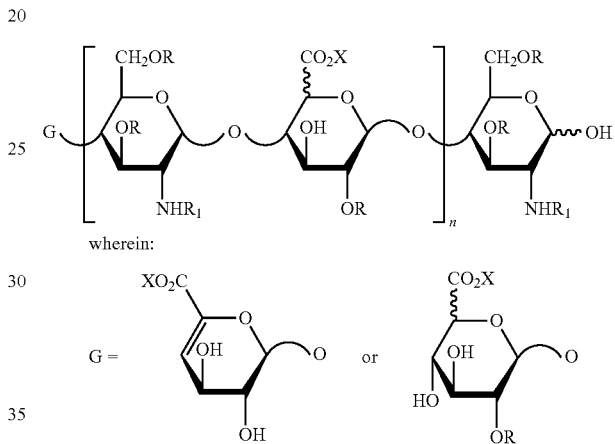

X is Na or Ca, R is H or SO₃Na;

R1 is SO₃Na or COCH₃;

n=2-45, e.g., 2-35; and the composition preferably has an average value for n of 7-11 or 8-12.

This composition can occur as an intermediate in the production of a LMWH, e.g., as the product of enzymatic digestion of the fast moving fraction (as discussed herein).

In a twelfth aspect, the invention features, a LMWH composition having the following structure:

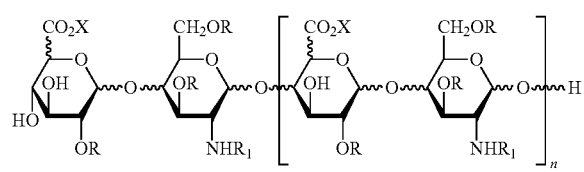

wherein X is Na or Ca, R is H or SO₃Na;

R1 is SO₃Na or COCH₃;

n=2-50, e.g., 2-40; and the composition preferably has an average value for n of 8 to 15, e.g., 10 to 15, or 9 to 16, e.g., 11 to 16.

In one embodiment, the LMWH composition has the following structure:

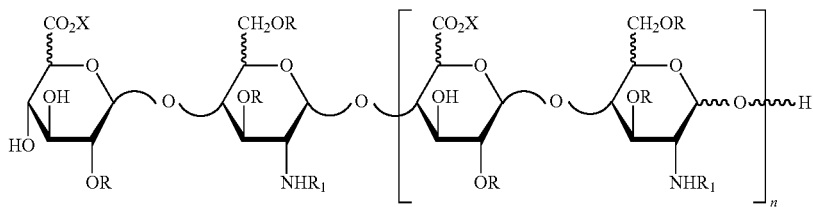

wherein X is Na or Ca, R is H or $SO_3Na$;
R1 is $SO_3Na$ or $COCH_3$;
n=2-50, e.g., 2-40; and
the composition preferably has an average value for n of 8 to 15, e.g., 10 to 15, or 9 to 16, e.g., 11 to 16.

This composition can occur as an intermediate in the production of a LMWH, e.g., as the product of precipitations to provide a fast moving fraction (as discussed herein).

Any of the LMWHs described herein, e.g., described above, can have other properties. E.g., one of the above described compositions can further have one or more of functional or structural properties set out below.

Thus, in one embodiment, the LMWH composition has an anti-Xa activity of about 100 to 400 IU/mg, e.g., about 120 to 380 IU/mg, e.g., about 150 to 350 IU/mg, e.g., about 170 to 330 IU/mg, e.g., about 180 to 300 IU/mg, e.g., about 150 to 200 IU/mg, 200 to 300 IU/mg, 130 to 220 IU/mg, 225 to 274 IU/mg.

In one embodiment, the LMWH composition has an anti-Xa activity that is at least 50%, 60%, 70%, 80%, 85%, 90%, 95%, 99%, 100% neutralizable, e.g., as measured by anti-Xa activity, ACT or aPTT. Preferably, the anti-Xa activity is neutralized by at least 50%, 60%, 70%, 80%, 85%, 90%, 95%, 99% or 100% within 5, 10, 15 minutes after protamine administration. For example, the anti-Xa activity can be neutralized by at least 50%, 60%, 70%, 80%, 85%, 90%, 95%, 99% or 100% within 5, 10, 15, 30 minutes after protamine administration at a dose of about 1, 2, 3 mg of the LMWH composition per 100 anti-Xa IU of plasma.

In another embodiment, the LMWH composition has one or more of the following properties: the activity of the composition can be monitored by aPTT and/or ACT; the polydispersity of the composition is less than 1.6, e.g., the polydispersity is about 1.6 to 1.1, e.g., 1.5 to 1.1, e.g., 1.4 to 1.1, e.g., 1.3 to 1.1, e.g., 1.2 to 1.1; less than 70%, 60%, 50%, 45%, 40%, 35%, 30% of the chains present in the composition have a molecular weight greater than 7500 or 8000 Da; less than 40%, 35%, 30%, 25% of the chains present in the composition have a molecular weight less than 5500 or 5000 Da; the composition comprises a mixture of $\Delta U$ and I/G structures at the non-reducing ends of the chains; and fewer chains in the composition have PF4 binding sites than enoxaparin, dalteparin, UFH.

In one embodiment, about 15%, 20%, 25%, 30%, 35%, 45%, 50% of the chains in the LMWH composition have a $\Delta U$ at the non-reducing end. Preferably, about 15% to 50%, e.g., 15% to 35% of the chains, e.g., 20% to 35% of the chains in the composition have a $\Delta U$ at the non-reducing end.

In one embodiment, the LMWH composition has a higher degree of sulfation than enoxaparin or dalteparin. In one embodiment, the LMWH composition has more trisulfated disaccharides present in the composition than enoxaparin or dalteparin, e.g., the LMWH composition has about 50 to 65% trisulfated disaccharides, e.g., 55 to 60%, 55 to 58%, 57 to 60% trisulfated disaccharides, as determined by mole %.

In one embodiment, the composition comprises a higher level of $\Delta UH_{NAc,6S}GH_{NS,3S,6S}$ than enoxaparin, daltaparin and/or UFH, e.g., comprises about 5 to 15 mole %, e.g., 7 to 14 mole %, e.g., 9 to 12 mole %.

In one embodiment, the LMWH composition has a calcium content less than 3%, 2.5%, 2%, 1.5%, 1.0%, and/or a sodium content less than 30%, 25%, 20%, 15%, 10%. In one embodiment, the LMWH composition comprises: less than 1000 ng/mg, 750 ng/mg, 500 ng/mg, 250 ng/mg of a heparinase enzyme, e.g., a heparinase enzyme described herein; less than 1.0%, 0.5%, 0.3% w/w methanol; less than 1.0%, 0.5%, 0.3%, 0.1% w/w ethanol; less than 2.0%, 1.75%, 1.25%, 1.0%, 0.5%, 0.3%, 0.15% chloride; less than 15%, 10%, 5%, 2.5% water by weight; less than 2000, 1500, 1000, 950, 900, 850, 800, 750, 700, 650, 600, 550, 500, 450, 400, 350, 300 ppm of free sulfate.

In one embodiment, the LMWH composition provides increased TFPI release as compared to enoxaparin. In one embodiment, the LMWH provides at least a 2, 3, 4, 5, 6, 7, 8, 9, 10, 15, 20, 30, 40 fold increase in TFPI release as compared to enoxaparin.

In one embodiment, the LMWH composition has an intravenous half life of about 30 minutes to 3 hours, e.g., about 1 to 2 hours. In one embodiment, the LMWH composition has a subcutaneous half life of about 30 minutes to 3.0 or 3.5 hours, e.g., about 1.5 to 2.5 hours, e.g., about 2 hours.

In one embodiment of any of the first, second, third, fourth, fifth, sixth, seventh, eighth, ninth and tenth aspects, the LMWH composition has one or more of the following characteristics:
the composition has substantially no (e.g., at least 85%, 90%, 95% or more of the chains do not have) modified reducing end structures; at least 60%, 70%, 80%, 85%, 90%, 95%, 99% of the chains of the composition have $H_{NAc}$ at the reducing end; less than 90%, 95%, 98%, 99%, preferably none of the chains of the composition have a sulfated $\Delta U$ at the non-reducing end; there is substantially no linkage region (e.g., less than 0.1% linkage region) present in the composition; the composition has more chains with 3-O sulfates than commercially available LMWHs, e.g., enoxaparin or dalteparin; and the ratio of $\Delta UH_{NAc,6S}GH_{NS,3S,6S}$ to $\Delta U_{2S}H_{NS,6S}IH_{NAc,6S}GH_{NS,3S,6S}$ in the composition is about 1:1 to 4:1 (e.g., 1:1.2:1, 3:1 or 4:1). In one embodiment, the LMWH composition has two, three, four, five or all of these characteristics.

In another aspect, the invention features, a LMWH composition having the following properties:
a weight average molecular weight of about 5000 to 9000 Da;
anti-IIa activity of about 50 to 300 IU/mg;
anti-IIa activity that is at least 50% neutralizable with protamine, e.g., as measured by ACT or aPTT;
$\Delta UH_{NAc,6S}GH_{NS,3S,6S}$ is 5 to 15% of the composition, preferably $\Delta UH_{NAc,6S}GH_{NS,3S,6S}$ at the non-reducing end of about 5 to 15% of the composition;

an average chain length of about 9 to 16 disaccharides;
an anti Xa to anti-IIa ratio of 3:1 or less;
the anti-Xa to anti-IIa ratio remains relatively constant over the course of an administration of the LMWH, e.g., the anti-Xa to anti-IIa ratio varies no more than about ±1.5, ±1, ±0.5, or ±0.2, over a period of about 30, 60, 120, 180, 240, 300 minutes. For example, if an initial ratio of anti-Xa activity to anti-IIa activity is 2, then the ratio measured at a second time (e.g., 30, 60, 120, 180, 240, 300 minutes) after the initial administration will preferably be less than 3, and preferably at or around 2.

In a preferred embodiment, the LMWH composition has the following structure:

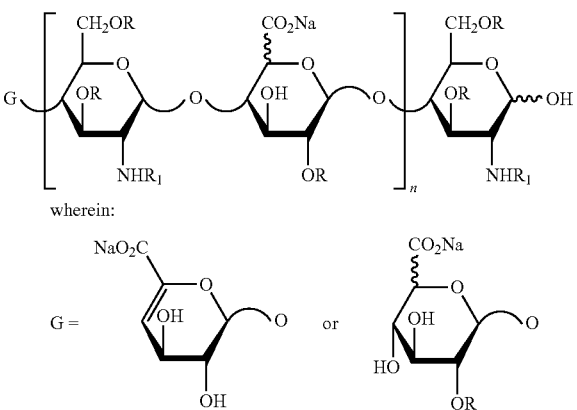

wherein:

R is H or $SO_3Na$;
R1 is $SO_3Na$ or $COCH_3$;
n=2-50, e.g., 2-40; and
the composition preferably has an average value for n of 9 to 16 or 8 to 15.

In a preferred embodiment, the LMWH composition has the following properties:
anti-Xa activity of about 100 to 400 IU/mg;
anti-Xa activity that is at least 50% neutralizable, e.g., as measured by anti-Xa activity, ACT or aPTT;
a polydispersity of less than 1.6;
less than 70%, 60%, 50% of the chains present in the composition have a molecular weight greater than 7500 Da;
less than 40% of the chains present in the composition have a molecular weight less than 5000 Da;
it includes a mixture of $\Delta U$ and I/G structures at the non-reducing ends of the chains;
it has substantially no modified reducing end structures;
fewer chains in the composition have PF4 binding sites than enoxaparin, dalteparin, or UFH;
at least 60%, 70%, 80%, 90% of the chains of the composition have HNAc at the reducing end;
about 15% to 35% of the chains in the composition have a $\Delta U$ at the non-reducing end;
less than 90%, 95%, 98%, 99%, preferably none of the chains of the composition have a sulfated $\Delta U$ at the non-reducing end.

In a preferred embodiment, the LMWH composition has the following properties:
it has a higher degree of sulfation than enoxaparin or dalteparin;
it has more trisulfated disaccharides present in the composition than enoxaparin or dalteparin, e.g., the LMWH composition has about 50 to 65% trisulfated disaccharides, as determined by mole % it has a higher level of $\Delta UH_{NAc,6S}GH_{NS,3S,6S}$ than enoxaparin, dalteparin and/or UFH, e.g., $\Delta UH_{NAc,6S}GH_{NS,3S,6S}$ is present at about 5 to 15 mole %.

In a preferred embodiment, the LMWH composition has the following properties:
it has a calcium content less than 3% and/or a sodium content less than 20%;
it includes less than 1000 ng/mg of a heparinase enzyme;
it has less than 1.0% w/w methanol;
it has less than 1.0% w/w ethanol;
it has less than 2.0% chloride;
it has less than 15% water by weight;
it has less than 2000 ppm of free sulfate.

In a preferred embodiment, the LMWH composition has the following properties:
it provides increased tissue factor pathway inhibitor (TFPI) release as compared to enoxaparin.

In a preferred embodiment, the LMWH composition has an intravenous half life of about 30 minutes to 3 hours.

In another aspect, the invention features, a method of making a LMWH. The method includes:
subjecting UFH to one, or a step-wise series, of aqueous alcohol (e.g., ethanol) precipitations (at least one with a sodium salt (or a salt other than a calcium salt)), to extract a lower molecular weight fraction from the unfractionated heparin (e.g., the fast moving fraction) to provide a first intermediate, wherein the first intermediate preferably has a average chain length of 10 to 16 disaccharides;
digesting the first intermediate using an agent, e.g., an enzyme or chemical, that cleaves glycosidic linkages of unsulfated uronic acids, e.g., an enzyme described herein, e.g., in aqueous buffer, e.g., in aqueous salt buffer, e.g., a sodium acetate buffer, pH of about 5-9, e.g., 7-8, at 25° C. to 52° C., e.g., 37° C., to produce a second intermediate, wherein the second intermediate preferably has a average chain length of 8 to 14 disaccharides, e.g., 8-12 disaccharides;
separating high molecular weight high anti-factor Xa and IIa components of from the second intermediate from the lower activity materials by a size based step, e.g., size exclusion chromatography (SEC), to produce the third intermediate wherein the third intermediate preferably has a average chain length of 9 to 16 disaccharides; and optionally
dissolving the third intermediate in purified water, filtering, e.g., through a 0.2 pm filter, and lyophilizing to drug substance.

In another aspect, the invention features, a LMWH composition made by a method described herein.

In another aspect, the method includes an intermediate or reaction mixture from any of the methods for making or analyzing a LMWH described herein.

In another aspect, the invention features, a pharmaceutical composition that includes a LMWH composition described herein.

In one embodiment, the pharmaceutical composition further includes a pharmaceutically acceptable carrier.

In one embodiment, the pharmaceutical composition is in a form suitable for systemic administration. In a preferred embodiment, the pharmaceutical composition is suitable for subcutaneous, intravenous, intra-arterial, intrasynoval, intramuscular, intraperitoneal, intravitreous, epidural, subdural or intrathecal administration. In one embodiment, a pharmaceutical composition for systemic administration can be an isotonic solution, e.g., an isotonic solution with or without preservatives. Examples of preservative include, but are not limited to, benzyl alcohol, mannitol and leucine. A unit dosage amount of a pharmaceutical composition of the invention can be disposed within a package or a device suitable for administration. E.g., a composition suitable for subcutaneous delivery can be disposed within a syringe configured for subcutaneous delivery, a composition suitable for intravenous delivery can be disposed within a syringe configured for intravenous delivery or within another device for intravenous delivery, e.g., an intravenous drip bag or bottle.

In one embodiment, the pharmaceutical composition is in a form suitable for local invasive administration, e.g., coating or within a device suitable for implantation. Examples of devices suitable for implantation include, but are not limited to, a stent, and an excorporeal circuit. In one embodiment, the pharmaceutical composition is in a form suitable for subcutaneous implantation, implantation into a tissue or organ (e.g., a coronary artery, carotid artery, renal artery, other peripheral arteries, veins, kidney, heart, cornea, vitreous, and cerebrum), or implantation into a space surrounding a tissue or organ (e.g., kidney capsule, pericardium, thoracic or peritoneal space.

In one embodiment, the pharmaceutical composition is in a form suitable for non-invasive administration, e.g., topical, transdermal, pulmonary, nasal, oral, auditory canal, rectal or vaginal administration. A unit dosage amount of a pharmaceutical composition of the invention can be disposed within a package or a device suitable for such administration.

In one embodiment, the LMWH composition is lyophilized. In another embodiment, the LMWH composition is a liquid.

In one embodiment, the invention features a container, e.g., an ampoule, syringe or vial, containing the pharmaceutical composition. In one embodiment, the LMWH composition is present at about 1500 IU, 2000 IU, 2500 IU, 3000 IU, 3500 IU, 4000 IU, 4500 IU, 5000 IU, 5500 IU, 6000 IU anti-Xa activity per mL pharmaceutically acceptable carrier.

In one embodiment, the pharmaceutical composition has an osmolality of about 200 to 400 mOsm/L, e.g., about 250 to 350 mOsm/L, about 280 to 330 mOsm/L. In one embodiment, the pharmaceutical composition further comprises sodium chloride and water.

In another aspect, the invention features a method of treating a subject including administering a LMWH disclosed herein to the subject. The treatment can be therapeutic, e.g., a treatment which lessens, mitigates or ameliorates an existing unwanted condition or symptom thereof, or prophylactic, e.g., a treatment which delays, e.g., prevents, the onset of an unwanted condition or symptom thereof. A LMWH composition described herein can be used to treat disorders which are treatable with UFH or with a commercial LMWH, e.g., enoxaparin, daltaparin or tinzaparin. The invention includes methods for treating a subject having, or at risk of having, a disorder or condition selected from the group consisting of: a disorder associated with coagulation, e.g., deep vein thrombosis (DVT) or pulmonary embolism, thrombosis or cardiovascular disease, e.g., acute coronary syndrome (ACS), stable or unstable angina, myocardial infarction, e.g., ST-segment elevated myocardial infarction (STEMI) or non-ST-segment elevated myocardial infarction (NSTEMI), vascular conditions or atrial fibrillation; migraine; atherosclerosis; an inflammatory disorder, such as autoimmune disease or atopic disorders, psoriasis, arthritis, sepsis; disseminated intravascular coagulopathy (DIC); an allergy or a respiratory disorder, such as asthma, emphysema, adult respiratory distress syndrome (ARDS), cystic fibrosis, or lung reperfusion injury; stenosis or restenosis; a cancer or metastatic disorder; an angiogenic disorder; a fibrotic disorder such as major organ fibrosis, fibroproliferative disorders and scarring associated with trauma; osteoporosis; Alzheimer's; bone fractures such as hip fractures. The subject can be undergoing, or have undergone, a surgical procedure, e.g., organ transplant, orthopedic surgery, joint replacement, e.g., hip replacement or knee replacement, percutaneous coronary intervention (PCI), stent placement, angioplasty, or coronary artery bypass graft surgery (CABG). The compositions of the invention are administered to a subject having or at risk of developing one or more of the diseases in an effective amount for treating the disorder or condition.

In one embodiment, the method further includes monitoring the activity of the LMWH composition in the subject using a coagulation assay, e.g., using ACT and/or aPTT.

In one embodiment, the method further includes administering protamine sulfate after administration of the LMWH composition to neutralize some or all of the activity, e.g., anti-Xa activity and/or anti-IIa activity, of the LMWH composition. In one embodiment, about 50%, 60%, 70%, 80%, 90%, 95% or all of the anti-IIa activity of the LMWH composition is neutralized, e.g., about 50%, 60%, 70%, 80%, 90%, 95% or all of the anti-IIa activity of the LMWH composition is neutralized within 5, 10, 15, 20, 25, 30, 40 minutes after protamine administration. In one embodiment, about 50%, 60%, 70%, 80%, 90%, 95% or all of the anti-IIa activity of the LMWH composition is neutralized, e.g., about 50%, 60%, 70%, 80%, 90%, 95% or all of the anti-IIa activity of the LMWH composition is neutralized within 5, 10, 15, 20, 25, 30, 40 minutes after protamine administration. In one embodiment, protamine sulfate is administered at a dose of about 1 mg, 2 mg, 3 mg, 5 mg of the LMWH composition per 100 anti-Xa IU of plasma. Neutralization of anti-Xa activity and/or anti-IIa activity can be determined, e.g., by ACT and/or aPTT.

In another aspect, the invention features, a method of treating (e.g., therapeutically or prophylactically treating) a disorder, e.g., a thrombotic disorder, in a subject. The method includes administering a LMWH composition described herein, to thereby treat, preferably prevent, the disorder. In one embodiment, the disorder is one or more of ACS, myocardial infarction, e.g., NSTEMI OR STEMI, stable angina and unstable angina. Preferably, the thrombotic disorder is arterial thrombosis, e.g., including STEMI. The disorder can be, e.g., associated with surgical intervention, e.g., PCI, stent placement or angioplasty. For example, the subject can have, or be at risk of having, or be recovering from, a surgical intervention, e.g., cardiology intervention (e.g., angioplasty, PCI, stent placement). In one embodiment, the subject is at risk for (e.g., is being considered for) receiving surgical intervention, e.g., CABG.

In one embodiment, the LMWH composition is administered to the subject intravenously, e.g., at a dose of about 0.03 mg/kg to 0.45 mg/kg, e.g., 0.03 mg/kg, 0.05 mg/kg, 0.1 mg/kg, 0.15 mg/kg, 0.2 mg/kg, 0.22 mg/kg, 0.25 mg/kg, 0.27 mg/kg, 0.3 mg/kg, 0.35 mg/kg, 0.37 mg/kg, 0.4 mg/kg, 0.44 mg/kg. In preferred embodiments the LMWH composition is administered intravenously at a dose of about 0.1 to 0.3 mg/kg, e.g., 0.1 mg/kg, 0.15 mg/kg, 0.20 mg/kg, 0.22 mg/kg, 0.25 mg/kg, 0.27 mg/kg or 0.30 mg/kg. In another embodiment, the LMWH composition is administered to the subject subcutaneously, e.g., at a dose of about 0.1 mg/kg, 0.15 mg/kg, 0.2 mg/kg, 0.25 mg/kg, 0.3 mg/kg, 0.35 mg/kg, 0.4 mg/kg, 0.44 mg/kg, 0.47 mg/kg, 0.5 mg/kg, 0.55 mg/kg, 0.60 mg/kg, 0.7 mg/kg, 0.8 mg/kg, 0.9 mg/kg, 1.0 mg/kg. In preferred embodiments, the LMWH composition is administered subcutaneously at a dose of about 0.15 to 1.0 mg/kg, 0.20 to 0.9 mg/kg, 0.25 to 0.9 mg/kg, 0.30 to 0.50 mg/kg, e.g., 0.30 mg/kg, 0.35 mg/kg, 0.40 mg/kg, 0.42 mg/kg, 0.44 mg/kg, 0.47 mg/kg or 0.50 mg/kg.

In one embodiment, the method further includes monitoring the activity of the LMWH composition in the subject using a coagulation assay, e.g., using ACT and/or aPTT. In one embodiment, anti-Xa activity and/or anti-IIa activity is monitored, e.g., with ACT and/or aPTT, prior to, during, or after surgical intervention, e.g., angioplasty, PCI, stent placement. In one embodiment, anti-Xa activity and/or anti-IIa activity is monitored, e.g., with ACT and/or aPTT, prior to, during, and/or after administration of the LMWH composition. In some embodiments, anti-Xa activity and/or anti-IIa activity is monitored by ACT, and the dose of LMWH is administered to achieve an ACT of about 200 to 350 seconds.

In one embodiment, the method further includes administering protamine sulfate after administration of the LMWH composition to neutralize some or all of the activity, e.g., anti-Xa activity and/or anti-IIa activity, of the LMWH composition. In one embodiment, at least about 50%, 60%, 70%, 80%, 90%, 95% or all of the anti-IIa activity of the LMWH composition is neutralized, e.g., at least about 50%, 60%, 70%, 80%, 90%, 95% or all of the anti-IIa activity of the LMWH composition is neutralized within 5, 10, 15, 20, 25, 30, 40 minutes after protamine administration. In one embodiment, at least about 50%, 60%, 70%, 80%, 90%, 95% or all of the anti-IIa activity of the LMWH composition is neutralized, e.g., at least about 50%, 60%, 70%, 80%, 90%, 95% or all of the anti-IIa activity of the LMWH composition is neutralized within 5, 10, 15, 20, 25, 30, 40 minutes after protamine administration. In one embodiment, protamine sulfate is administered at a dose of about 1-5 mg, e.g., 1 mg, 2 mg, 3 mg, 5 mg of the LMWH composition per 100 anti-Xa IU of plasma. Neutralization of anti-Xa activity and/or anti-IIa activity can be determined, e.g., by ACT and/or aPTT. In one embodiment, anti-Xa activity and/or anti-IIa activity can be determined, e.g., by ACT and/or aPTT, prior to, during and/or after administration of protamine sulfate. In one embodiment, anti-Xa activity and/or anti-IIa activity is neutralized prior to, during or after surgical intervention. For example, in one embodiment, anti-Xa activity and/or anti-IIa activity can be neutralized during or after a surgical intervention such as angioplasty or PCI. In another embodiment, the LMWH composition is neutralized prior to surgical intervention such as CABG.

In one embodiment, the method further includes monitoring the patient for a negative reaction, e.g., epidural or spinal hematoma, hemorrhage or bleeding.

In one embodiment, the LMWH composition is administered intravenously or subcutaneously.

In one embodiment, the LMWH composition is administered in combination with another therapeutic agent, e.g., an anticoagulant or antithrombotic agent, e.g., bivalirudin Angiomax), ASA, a GPIIbIIIa inhibitor (e.g., eptifibatide or abciximab), an ADP inhibitor (e.g., Plavix), rPA, TNKase, aspirin, a P2Y12 inhibitor, a platelet inhibitor, warfarin, and combinations thereof.

The reversible (neutralizable) and monitorable LMWH compositions disclosed herein allow for improved flexibility in treating patients, e.g., patients admitted to the hospital and undergoing evaluation for possible cardiovascular treatment, e.g., surgery. Accordingly, in another aspect, the invention features, a method of treating (e.g., therapeutic or prophylactic treatment) a disorder, e.g., a thrombotic or cardiovascular disorder, in a patient. The method includes:

optionally, administering a reversible and monitorable LMWH composition described herein to the patient;

classifying the patient (to whom the LMWH composition has been or will be administered) as not in need of surgical intervention (e.g., classifying the patient as not in need of surgical intervention prior to release from the hospital) or as a candidate for surgical intervention prior to release from the hospital;

optionally, if the patient is classified as a candidate for surgical intervention then performing one or both of monitoring (e.g., as described herein, e.g., with a coagulation assay, e.g., using ACT and/or aPTT) the reversible and monitorable LMWH composition and neutralizing (e.g., as described herein, e.g., by administering protamine sulfate) the reversible and monitorable LMWH composition.

In one embodiment, the LMWH composition is administered to the subject intravenously, e.g., at a dose of about 0.03 mg/kg to 0.45 mg/kg, e.g., 0.03 mg/kg, 0.05 mg/kg, 0.1 mg/kg, 0.15 mg/kg, 0.2 mg/kg, 0.22 mg/kg, 0.25 mg/kg, 0.27 mg/kg, 0.3 mg/kg, 0.35 mg/kg, 0.37 mg/kg, 0.4 mg/kg, 0.44 mg/kg. In preferred embodiments the LMWH composition is administered intravenously at a dose of about 0.1 to 0.3 mg/kg, e.g., 0.1 mg/kg, 0.15 mg/kg, 0.20 mg/kg, 0.22 mg/kg, 0.25 mg/kg, 0.27 mg/kg or 0.30 mg/kg. In another embodiment, the LMWH composition is administered to the subject subcutaneously, e.g., at a dose of about 0.1 mg/kg, 0.15 mg/kg, 0.2 mg/kg, 0.25 mg/kg, 0.3 mg/kg, 0.35 mg/kg, 0.4 mg/kg, 0.44 mg/kg, 0.47 mg/kg, 0.5 mg/kg, 0.55 mg/kg, 0.60 mg/kg, 0.7 mg/kg, 0.8 mg/kg, 0.9 mg/kg, 1.0 mg/kg. In preferred embodiments, the LMWH composition is administered subcutaneously at a dose of about 0.15 to 1.0 mg/kg, 0.20 to 0.8 mg/kg, 0.25 to 0.90 mg/kg, 0.30 to 0.50 mg/kg, e.g., 0.30 mg/kg, 0.35 mg/kg, 0.40 mg/kg, 0.42 mg/kg, 0.44 mg/kg, 0.47 mg/kg or 0.50 mg/kg.

In a preferred embodiment, the patient is classified as a candidate for surgical intervention, e.g., PCI, stent placement or angioplasty, and the effect of the reversible and monitorable LMWH composition is monitored. In a preferred embodiment, the surgical intervention is performed and the reversible and monitorable LMWH composition is monitored at one or more, or all, of before, during and after the surgery. In one embodiment, the patient is monitored for an ACT of about 200 to 350 before and/or during a surgical intervention such as PCI.

In a preferred embodiment, the patient is classified as a candidate for surgical intervention, e.g., CABG and the effect of the reversible and monitorable LMWH composition is one or both of monitored and neutralized. In a preferred embodiment, the surgical intervention is performed and the reversible and monitorable LMWH composition monitored one or more, or all of before, during and after the surgery. In one embodiment, the patient is monitored for an ACT of about 400 to 600, e.g., 400 to 500 prior to surgical intervention such as CABG.

In a preferred embodiment, the subject is being treated for a thrombotic disorder.

In one embodiment, the disorder is one or more of ACS, myocardial infarction, e.g., NSTEMI OR STEMI, stable angina and unstable angina. Preferably, the thrombotic disorder is arterial thrombosis, e.g., including ST elevation (STEMI).

In another aspect, the invention features, a method of monitoring a subject treated with a monitorable LMWH composition described herein. The method includes, optionally, administering a monitorable LMWH composition described herein to the subject; and evaluating aPTT and/or ACT in the subject (who has been administered the monitorable LMWH composition).

In one embodiment, a baseline aPTT and/or ACT is determined prior to treating the subject with the LMWH. In one embodiment, the method includes comparing aPTT and/or ACT of a subject that has received the LMWH to the baseline aPTT and/or ACT.

In one embodiment, the subject is monitored at one or more, or all, of the following stages: prior to, during and after receiving a LMWH composition. In one embodiment, the subject is monitored prior to, during and/or after surgical intervention, e.g., PCI, stent placement or angioplasty. In one embodiment, the LMWH composition is monitored for an ACT of about 200 to 350 prior to and/or during a surgical intervention such as PCI. In another embodiment, the LMWH composition is monitored for an ACT of about 400 to 600, e.g., about 400 to 500, prior to CABG.

In another aspect, the invention features, a method of treating a subject who has been administered a reversible LMWH composition described herein. The method includes:

optionally, administering a reversible LMWH composition described herein to the subject; and neutralizing (e.g., as described herein, e.g., by administering protamine sulfate) the reversible LMWH composition.

In one embodiment, the subject is monitored at one or more, or all, of the following stages: prior to, during and after administration of protamine sulfate.

In another aspect, the invention features, a method of advising on, or providing instructions (e.g., written, oral, or computer generated instructions) for, the use of a LMWH having high anti-IIa activity, e.g., a LMWH composition described herein. The method includes providing instruction regarding use, e.g., with: patients having abnormal renal function or diabetes or clot bound thrombin; patients who are candidates for PCI, stent placement, CABG, angioplasty, etc.; interventional cardiology patients; patients in need of neutralization of previously administered LMWH, e.g., neutralizing with protamine sulfate; patients at risk of epidural or spinal hematoma, hemorrhage and/or bleeding. In one embodiment, the instruction pertains to administration of the LMWH composition for ACS, myocardial infarction, e.g., NSTEMI OR STEMI, stable angina and unstable angina, e.g., administration in a sub population of patients such as patients having abnormal renal function, or elderly patients (e.g., patients over 60 years of age). In one embodiment, the instruction pertains to administration of the LMWH composition for thrombotic disorders, e.g., thrombotic disorders associated with surgical intervention, e.g., PCI, stent replacement or angioplasty.

In another aspect, the invention features, a method of advising on the use of a LMWH composition described herein, that includes providing instruction regarding monitoring anti-Xa activity and/or anti-IIa activity using ACT and/or aPTT.

In another aspect, the invention features, a method of manufacturing a LMWH composition, e.g., a LMWH composition described herein. The method includes one or more of the following steps:

(1) subjecting a glycosaminoglycan (GAG) containing sample, e.g., UFH, to a first a precipitation, e.g., with a polar organic solvent (e.g., an alcohol, e.g., ethanol), a polar non-organic solvent (e.g., water), and a salt (e.g., a sodium salt, e.g., sodium acetate, or calcium salt, e.g., calcium acetate), to yield a first supernatant;

(2) subjecting the first supernatant to a second precipitation, e.g., with a polar organic solvent (e.g., an alcohol, e.g., ethanol), and a polar non-organic solvent (e.g., water), to yield a precipitate (this can be used to provide a fast moving fraction as discussed elsewhere herein);

(3) solubilizing the precipitate, preferably in water, and cleaving the solubilized precipitate with an agent that cleaves glycosidic linkages of unsulfated uronic acids, e.g., adjacent to an N-acetyl glucosamine residue. An example is a heparinase III enzyme described herein, preferably MO11, preferably in the presence of sodium acetate, and preferably to completion, e.g., as indicated by a UV plateau, to provide a cleaved preparation;

(4) precipitating the cleaved preparation, e.g., with a salt, e.g., a sodium salt, preferably sodium chloride, and a polar organic solvent, e.g., an alcohol, e.g., methanol, to form solids, having saccharides with e.g., an average chain length of 8-14, e.g., 8-12 dissaccharides;

(5) subjecting material from the solids to a purification step, e.g., a chromatographic purification step, e.g., size selection step, e.g., exclusion chromatography, ion exchange chromatography, or filtration, to provide a preparation with a higher average molecular weight than in step (4). In a preferred embodiment the higher average molecular weight preparation has an average chain length of 9 to 16 dissacharides or an average molecular weight of 5000 to 9000 Da.

In another aspect, the invention features, methods of making a LMWH composition having an average chain length of about 9 to 16 disaccharides. The method includes:

providing a precursor LMWH composition (e.g., a intermediate composition from a method described herein) having an average chain length of less than 9 to 16 disaccharides, preferably about 8 to 14 disaccharides, e.g., 8 to 12 disaccharides; and processing the precursor LMWH composition to obtain a LMWH having an average chain length of about 9 to 16 disaccharides.

Preferably, the processing includes size-based selection, e.g., a size-dependent separation, e.g., by one or more of size exclusion chromatography, ion exchange chromatography or filtration.

In one embodiment, the precursor LMWH composition is a preparation having an average chain length of about 8 to 14 disaccharides, e.g., 8 to 12 disaccharides. In a preferred embodiment it was obtained by a method including salt precipitation and enzymatic digestion of a higher molecular weight preparation, e.g., UFH. In one embodiment, the salt is a salt of a monovalent or divalent cation. Examples of monovalent and divalent cations that can be used include, e.g., sodium, potassium, rubidium, cesium, barium, calcium, magnesium, strontium, and combinations thereof. In one embodiment, the salt of monovalent or divalent cation is an acetate of a monovalent or divalent cation.

In one embodiment, the enzyme (or enzymes) used for digestion cleaves at one or more glycosidic linkages of unsulfated uronic acids, e.g., adjacent to an N-acetyl glucosamine residue. Examples of enzymes that can be used include, e.g., heparinase III, mutants of heparinase III, e.g., a heparinase III mutant described in U.S. Pat. No. 5,896,789 (e.g., a mutant of heparinase III having one or more histidine residue selected from the group consisting of His 36, His105, His110, His139, His152, His225, His234, His 241, His424, His469, and His539 has been substituted with an alanine), and heparin sulfate glycosaminoglycan lyase III from *Bacteroides thetaiotaomicron*. In a preferred embodiment, the enzyme used for digestion is a mutated heparinase III having an alanine at residue 225 of the amino acid sequence substituted with an alanine.

In a preferred embodiment, the precursor composition can be obtained by:

(1) subjecting a glycosaminoglycan (GAG) containing sample, e.g., UFH, to a first a precipitation, e.g., with a polar organic solvent (e.g., an alcohol, e.g., ethanol), a polar non-organic solvent (e.g., water), and a salt (e.g., a sodium salt, e.g., sodium acetate, or a calcium salt, e.g., calcium acetate), to yield a first supernatant;

(2) subjecting the first supernatant to a second precipitation, e.g., with a polar organic solvent (e.g., an alcohol, e.g., ethanol), and a polar non-organic solvent (e.g., water), to yield a precipitate (this can be used to provide a fast moving fraction as discussed elsewhere herein);

(3) solublizing the precipitate and cleaving the solubilized precipitate with a heparinase III enzyme, preferably M011, preferably in the presence of sodium acetate, and preferably to completion as, e.g., indicated by UV absorption of greater than 9.8, to provide a cleaved preparation.

In one aspect, the invention features a method of making a LMWH composition, e.g., a LMWH composition described herein. The method includes:

(1) subjecting a glycosaminoglycan (GAG) containing sample, e.g., UFH, to a first a precipitation, e.g., with a polar organic solvent (e.g., an alcohol, e.g., ethanol), a polar non-organic solvent (e.g., water), and a sodium salt (e.g., sodium acetate), to yield a first supernatant;

(2) subjecting the first supernatant to a second precipitation, e.g., with a polar organic solvent (e.g., an alcohol, e.g., ethanol), and a polar non-organic solvent (e.g., water), to yield a precipitate (this can be used to provide a fast moving fraction as discussed elsewhere herein);

(3) optionally solublizing the precipitate and cleaving the solubilized precipitate with a enzyme described herein, preferably in the presence of sodium acetate, and preferably to completion as, e.g., indicated by UV absorption of greater than 9.8, to provide a cleaved preparation; and (4) optionally processing the fraction to produce a LMWH preparation.

In one embodiment, the enzyme (or enzymes) used for digestion cleaves at one or more glycosidic linkages of unsulfated uronic acids, e.g., adjacent to an N-acetyl glucosamine residue. Examples of enzymes that can be used include, e.g., heparinase III, mutants of heparinase III, e.g., a heparinase III mutant described in U.S. Pat. No. 5,896,789 (e.g., a mutant of heparinase III having one or more histidine residue selected from the group consisting of His 36, His105, His110, His139, His152, His225, His234, His241, His424, His469, and His539 has been substituted with an alanine), and heparin sulfate glycosaminoglycan lyase III from *Bacteroides thetaiotaomicron*. In a preferred embodiment, the enzyme used for digestion is a mutated heparinase III having an alanine at residue 225 of the amino acid sequence substituted with an alanine.

In one embodiment, the digested fraction is the final product. In other embodiments, the method can include one or more additional processing steps to obtain a final product. In one embodiment, the method includes processing the digested fraction to obtain a LMWH composition having an average chain length of 9 to 16 disaccharides. In one embodiment, size exclusion chromatography, ion exchange chromatography and/or filtration can be used to obtain a LMWH composition having an average chain length of 9 to 16 disaccharides.

In another aspect, the invention features, methods of evaluating or processing a GAG such as UFH to determine suitability of the GAG for processing into a LMWH composition, e.g., a LMWH composition described herein. The method includes determining the quantity of N-acetyl present in a GAG preparation, comparing the quantity to a preselected criterion and making a decision about the GAG preparation based upon the whether the preselected criterion is met. In a preferred embodiment, a decision or step is taken, e.g., the GAG preparation is classified, accepted or discarded, processed into a drug substance or drug product, or a record made or altered to reflect the determination, depending upon whether the preselected criterion is met. In some embodiments, when the preselected criterion is not met, a decision can be made about altering one or more steps in manufacturing of a LMWH composition.

In one embodiment, the preselected criterion is N-acetyl present in the GAG preparation at an amount of about 11% or higher, e.g., as determined by mole %, relative to total glucosamine content. A GAG preparation having N-acetyl content within this range is indicative of a GAG preparation suitable for processing into a LMWH composition, e.g., a LMWH composition described herein. In such embodiments, when this preselected criterion is met, the GAG preparation is accepted and processed into intermediates, drug substance or drug product.

In one embodiment, the amount of N-acetyl present in a GAG preparation can be determined using, e.g., nuclear magnetic resonance (NMR).

In preferred embodiments, methods disclosed herein are useful from a process standpoint, e.g., to monitor or ensure batch-to-batch consistency or quality, or to evaluate a sample with regard to a preselected criterion.

In one aspect, the invention features, a method of evaluating or processing an intermediate LMWH preparation, e.g., produced by a method described herein, to determine suitability of the intermediate preparation for processing into a LMWH composition. The intermediate LMWH preparation is a fast moving fraction obtained, e.g., by salt precipitation with sodium or sodium acetate of a glycosaminoglycan (GAG) containing sample in a solvent as described herein. The method includes comparing the quantity of one or more of structural moieties, e.g., one or more of sulfated iduronic acid, N-sulfated hexosamine linked to uronic acid, epoxide and 6-O sulfated hexosamine, in the intermediate LMWH preparation to the quantity of the same structural moiety in unfractionated heparin starting material, and making a decision about the intermediate LMWH preparation based upon whether a preselected criterion between the starting material and intermediate LMWH preparation is met. In a preferred embodiment, a decision or step is taken, e.g., the intermediate LMWH preparation is classified, accepted or discarded, processed into a drug substance or drug product, or a record made or altered to reflect the determination, depending upon whether the a preselected relationship is met. In some embodiments, when the preselected criterion is not met, a decision can be made about altering one or more steps in manufacturing of a LMWH composition.

In one embodiment, the preselected criterion is a decrease in sulfated iduronic acid in the intermediate preparation as compared to the starting material. An intermediate preparation having a decreased sulfated iduronic acid content is indicative of an intermediate preparation suitable for further processing into a LMWH composition, e.g., a LMWH composition described herein. In such embodiments, when this preselected criterion is met, the intermediate preparation is accepted and processed into further intermediates, drug substance or drug product.

In one embodiment, the preselected criterion is an increase in N-sulfated hexosamine linked to uronic acid (e.g., iduronic and/or glucuronic acid) in the intermediate preparation as compared to the starting material. An intermediate preparation having an increased N-sulfated hexosamine linked to uronic acid is indicative of an intermediate preparation suitable for further processing into a LMWH composition, e.g., a LMWH composition described herein. In such embodiments, when this preselected criterion is met, the intermediate preparation is accepted and processed into further intermediates, drug substance or drug product.

In one embodiment, the preselected criterion is a decrease in epoxide in the intermediate preparation as compared to the starting material. An intermediate preparation having a decreased epoxide content is indicative of an intermediate preparation suitable for further processing into a LMWH composition, e.g., a LMWH composition described herein. In such embodiments, when this preselected criterion is met, the intermediate preparation is accepted and processed into further intermediates, drug substance or drug product.

In one embodiment, the preselected criterion is an increase in 6-O sulfated hexosamine in the intermediate preparation as compared to the starting material. An intermediate preparation having increased 6-O sulfated hexosamine is indicative of an intermediate preparation suitable for further processing into a LMWH composition, e.g., a LMWH composition described herein. In such embodiments, when this preselected criterion is met, the intermediate preparation is accepted and processed into further intermediates, drug substance or drug product.

In one embodiment, the amount of a structural moiety in the starting material and/or intermediate preparation is determined using one or more of nuclear magnetic resonance (NMR), capillary electrophoresis (CE) and high performance liquid chromatography (HPLC).

In preferred embodiments, methods disclosed herein are useful from a process standpoint, e.g., to monitor or ensure batch-to-batch consistency or quality, or to evaluate a sample with regard to a preselected criterion.

Certain characteristics can make a UFH sample a more preferred starting material for making a LMWH of the inventions. Accordingly, in another aspect, the invention provides a method of evaluating a UFH preparation as a starting material to make a LMWH composition described herein.

The method includes providing an evaluation of the UFH preparation for a parameter related to suitability of the UFH sample for use in the making of a LMWH described herein; and optionally, providing a determination of whether a value (e.g., a value correlated to presence, amount, distribution, or absence) determined for the parameter meets a preselected criterion, e.g., is present, or is present within a preselected range, thereby evaluating the UFH sample.

In a preferred embodiment, the criterion is satisfied and the UFH sample is selected and processed into the LMWH.

In a preferred embodiment, the parameter is the presence or amount of a structure listed in Table 2, preferably one related to the efficacy of a step in the method of making the LMWH, e.g., a structure which promotes or is positively correlated with cleavage by a heparinase, e.g., $H_{NAc\ (internal)}$.

In a preferred embodiment, the method includes determining if the amount of $H_{NAc\ (internal)}$ in the UFH sample has a predetermined relationship with a reference, e.g., it is equal to or greater than a preselected reference value.

In a preferred embodiment, a value for the parameter in an intermediate used in making the LMWH is also determined and optionally, that value must also meet a predetermined criterion to select the UFH for use in making the LMWH.

In one aspect, the invention provides a method of evaluating a UFH preparation, as a starting material to make a LMWH composition described herein.

The method includes optionally, performing an operation, e.g., a precipitation, on the UFH sample to provide an intermediate (preferably the steps used to produce this intermediate and the intermediate are the same as the steps and an intermediate of the method used to make the LMWH); providing an evaluation of the intermediate preparation for a parameter related to suitability of the UFH sample for use in the making of a LMWH described herein; and optionally, providing a determination of whether a value (e.g., a value correlated to presence, amount, distribution, or absence) determined for the parameter meets a preselected criterion, e.g., is present, or is present within a preselected range, thereby evaluating the UFH preparation.

In a preferred embodiment, the criterion is satisfied and the UFH sample is selected and processed into the LMWH.

In a preferred embodiment, the parameter is the presence or amount of a structure listed in Table 2, preferably one related to the efficacy of a step in the method of making the LMWH, e.g., a structure which promotes or is positively correlated with cleavage by a heparinase, e.g., $H_{NAc\ (internal)}$.

In a preferred embodiment, the method includes determining if the amount of $H_{NAc\ (internal)}$ in the intermediate sample has a predetermined relationship with a reference, e.g., it is equal to or greater than a preselected reference.

In a preferred embodiment, a value for the parameter in the UFH is also determined and optionally, that value must also meet a predetermined criterion to select the UFH for use in making the LMWH.

In preferred embodiments of either of these methods, a decision or step is taken, e.g., the sample is classified, selected, accepted or discarded, released or withheld, processed into a drug product, shipped, moved to a different location, formulated, labeled, packaged, released into commerce, or sold or offered for sale, or a record made or altered to reflect the determination, depending on whether the preselected criterion is met. E.g., based on the result of the determination or whether one or more subject entities is present, or upon comparison to a reference standard, the batch from which the sample is taken can be processed, e.g., as just described.

In either method, a preferred embodiment includes analyzing the sample with NMR.

In a preferred embodiment, either method can include providing a comparison of the value determined for a parameter with a reference value or values, to thereby evaluate the sample. In preferred embodiments, the comparison includes determining if the test value has a preselected relationship with the reference value, e.g., determining if it meets the reference value. The value need not be a numerical value but, e.g., can be merely an indication of whether the subject entity is present.

A preferred embodiment of either method can include determining if a test value is equal to or greater than a reference value, if it is less than or equal to a reference value, or if it falls within a range (either inclusive or exclusive of one or both endpoints).

In preferred embodiments of either method, the test value, or an indication of whether the preselected criterion is met, can be memorialized, e.g., in a computer readable record.

In preferred embodiments of either method, the intermediate is prepared by one or more or all of the following steps:

(1) subjecting a UFH sample to a first a precipitation, e.g., with a polar organic solvent (e.g., an alcohol, e.g., ethanol), a polar non-organic solvent (e.g., water), and a salt (e.g., a sodium salt, e.g., sodium acetate), to yield a first supernatant;

(2) subjecting the first supernatant to a second precipitation, e.g., with a polar organic solvent (e.g., an alcohol, e.g., ethanol), and a polar non-organic solvent (e.g., water), to yield a precipitate (this can be used to provide a fast moving fraction as discussed elsewhere herein);

(3a) solublizing the precipitate, preferably in water;

(3b) cleaving the solubilized precipitate with an enzyme (or enzymes) that cleaves glycosidic linkages of unsulfated uronic acid, e.g., adjacent to an N-acetyl glucosamine residue, e.g., heparinase III enzyme, preferably MO11, preferably in the presence of sodium acetate, and preferably to completion as, e.g., indicated by UV absorption of greater than 9.8, to provide a cleaved preparation The preferred intermediate is that produced in step (2) or (3a), though the method can use others.

In another aspect, the invention features, a method of evaluating a LMWH preparation described herein. The method includes: providing a LMWH preparation described herein; determining if a structure, activity or function described herein is present in or possessed by the preparation, thereby evaluating a LMWH preparation described herein. In a preferred embodiment, the determining includes determining if the structure, activity or function is present at a preselected level or in a preselected range, e.g., a level or range disclosed herein.

Accordingly, in one aspect, the invention provides a method of evaluating or processing a LMWH composition described herein. The method includes: providing an evaluation of a parameter related to a peak listed in Table 10A. Such parameters can include, or be a function of, the presence, relative distribution, or amount of a peak, and, optionally, providing a determination of whether a value (e.g., a value correlated to presence, amount, distribution, or absence) determined for the parameter meets a preselected criterion, e.g., is present, or is present within a preselected range, thereby evaluating or processing the mixture.

In a preferred embodiment, the method includes analyzing, e.g., separating, a digest of the sample by digestion with heparinase I, heparinase II, heparinase III by electrophoresis, e.g., capillary electrophoresis.

In a preferred embodiment, the method includes evaluating a sample to determine if one or more of the peaks listed in Table 10A is present.

In a preferred embodiment, the method includes providing a comparison of the value determined for a parameter with a reference value or values, to thereby evaluate the sample. In preferred embodiments, the comparison includes determining if the test value has a preselected relationship with the reference value, e.g., determining if it meets the reference value. The value need not be a numerical value but, e.g., can be merely an indication of whether the subject entity is present.

In a preferred embodiment, the method includes determining if a test value is equal to or greater than a reference value, if it is less than or equal to a reference value, or if it falls within a range (either inclusive or exclusive of one or both endpoints). By way of example, the amount of a peak listed in Table 10A can be determined and, optionally shown to fall within a preselected range, e.g., a range which corresponds to a range from Table 10A. In a preferred embodiment: the amount of each peak is about that found in Table 10A, the amount of each peak is within a range provided in Table 10A; the amount of peaks 10 and 11 are with a range provided in Table 10A.

In preferred embodiments, the test value, or an indication of whether the preselected criterion is met, can be memorialized, e.g., in a computer readable record.

In preferred embodiments, a decision or step is taken, e.g., the sample is classified, selected, accepted or discarded, released or withheld, processed into a drug product, shipped, moved to a different location, formulated, labeled, packaged, released into commerce, or sold or offered for sale, or a record made or altered to reflect the determination, depending on whether the preselected criterion is met. E.g., based on the result of the determination or whether one or more subject entities is present, or upon comparison to a reference standard, the batch from which the sample is taken can be processed, e.g., as just described.

The structures in Table 10A can be determined using CE, and when necessary, by other analytical methods.

In another aspect, the invention features, a method of evaluating or processing a LMWH preparation described herein. The method includes:

providing a LMWH preparation which has been digested with heparinase 1, heparinase II, heparinase III and separated by a separation technique such as CE;

determining if one or more of the peaks listed in Table 10A is present.

In a preferred embodiment, the method includes determining if a peak listed in Table 10A falls within a preselected range from Table 10A. In a preferred embodiment: the amount of each peak is about that found in Table 10A, the amount of each peak is within a range provided in Table 10A; the amount of peaks 10 and 11 are with a range provided in Table 10A.

In another aspect, the invention provides a method of evaluating or processing a LMWH composition described herein.

The method includes providing an evaluation of a parameter related to the structure or structures of Table 11A. Such parameters can include, or be a function of, the presence, relative distribution, or amount of a structure, and, optionally, providing a determination of whether a value (e.g., a value correlated to presence, amount, distribution, or absence) determined for the parameter meets a preselected criterion, e.g., is present, or is present within a preselected range, thereby evaluating or processing the mixture.

In a preferred embodiment, the method includes analyzing the composition using 2D-NMR.

In a preferred embodiment, the method includes evaluating a sample to determine if one or more of the structures provided in Table 11A is present.

In a preferred embodiment, the method includes providing a comparison of the value determined for a parameter with a reference value or values, to thereby evaluate the sample. In preferred embodiments, the comparison includes determining if the test value has a preselected relationship with the reference value, e.g., determining if it meets the reference value. The value need not be a numerical value but, e.g., can be merely an indication of whether the structure is present.

In a preferred embodiment, the method includes determining if a test value is equal to or greater than a reference value, if it is less than or equal to a reference value, or if it falls within a range (either inclusive or exclusive of one or both endpoints). By way of example, the amount of a structure provided in Table 11A can be determined and, optionally shown to fall within a preselected range, e.g., a range which corresponds to a range from Table 11A. In a preferred embodiment: the amount of each structure is about that found in Table 11A, the amount of each structure is within a range provided in Table 11A.

In preferred embodiments, the test value, or an indication of whether the preselected criterion is met, can be memorialized, e.g., in a computer readable record.

In preferred embodiments, a decision or step is taken, e.g., the sample is classified, selected, accepted or discarded, released or withheld, processed into a drug product, shipped, moved to a different location, formulated, labeled, packaged, released into commerce, or sold or offered for sale, or a record made or altered to reflect the determination, depending on whether the preselected criterion is met. E.g., based on the result of the determination or whether one or more structures is present, or upon comparison to a reference standard, the batch from which the sample is taken can be processed, e.g., as just described.

The structures in Table 11A can be determined using 2D NMR, and when necessary, by other analytical methods.

In another aspect, the invention features, a method of evaluating or processing a LMWH preparation described herein. The method includes providing a LMWH preparation which has been analyzed using 2D NMR; determining if one or more of the structure listed in Table 11A is present.

In a preferred embodiment, the method includes determining if a structure listed in Table 11A falls within a preselected range, e.g., a range which corresponds to a range 1 from Table 11A. In a preferred embodiment: the amount of each structure is about that found in Table 11A, the amount of each structure is within a range provided in Table 11A.

Some methods described herein include making a determination of whether a subject entity is present at a preselected level or within a preselected range and that level or range is expressed in specific units of measurement, e.g., mole %, e.g., present in a range of X-Y mole %. One can perform the method by determining the amount of subject entity in terms of mole % and then compare that with a reference expressed in mole %, in this example, X-Y mole %. One need not, however, make the measurement in terms of mole % and compare it with reference values expressed in mole %. The sample has an actual level of subject entity, which can be expressed as X-Y when described in units of mole %. That actual level can also be expressed in other units, e.g., weight %. That actual level is the same regardless of the units in which it is expressed. The specification of mole % in the method is merely to indicate the actual prevalence of the subject entity. The level of subject entity can be measured in terms of other units and the reference value can be expressed in terms of other units, as long as the reference value as expressed in terms of alternative units corresponds to the same amount of subject entity as the reference value expressed in mole %, e.g., X-Y mole % in this example. Thus, a method which requires showing the subject entity is present at X-Y mole % can be performed by showing that the subject entity is present in a range expressed in an alternative unit of measure, e.g., weight %, chain number, or % AUC, wherein the range, as described in the alternative unit of measure, corresponds to the same amount of subject entity which would give the mole % referred to, in this example X-Y mole %.

One can establish a functionally equivalent range for an alternative unit of measure by applying art known methods in conjunction with this specification. E.g., one can provide samples in the range of X-Y mole %, and then establish the corresponding range for those samples for in terms of an alternative unit of measure.

Other features and advantages of the invention will be apparent from the following detailed description, and from the claims.

DESCRIPTION OF THE DRAWINGS

The drawings are first briefly described.

DETAILED DESCRIPTION

Optimized LMWHs

Figure 1:
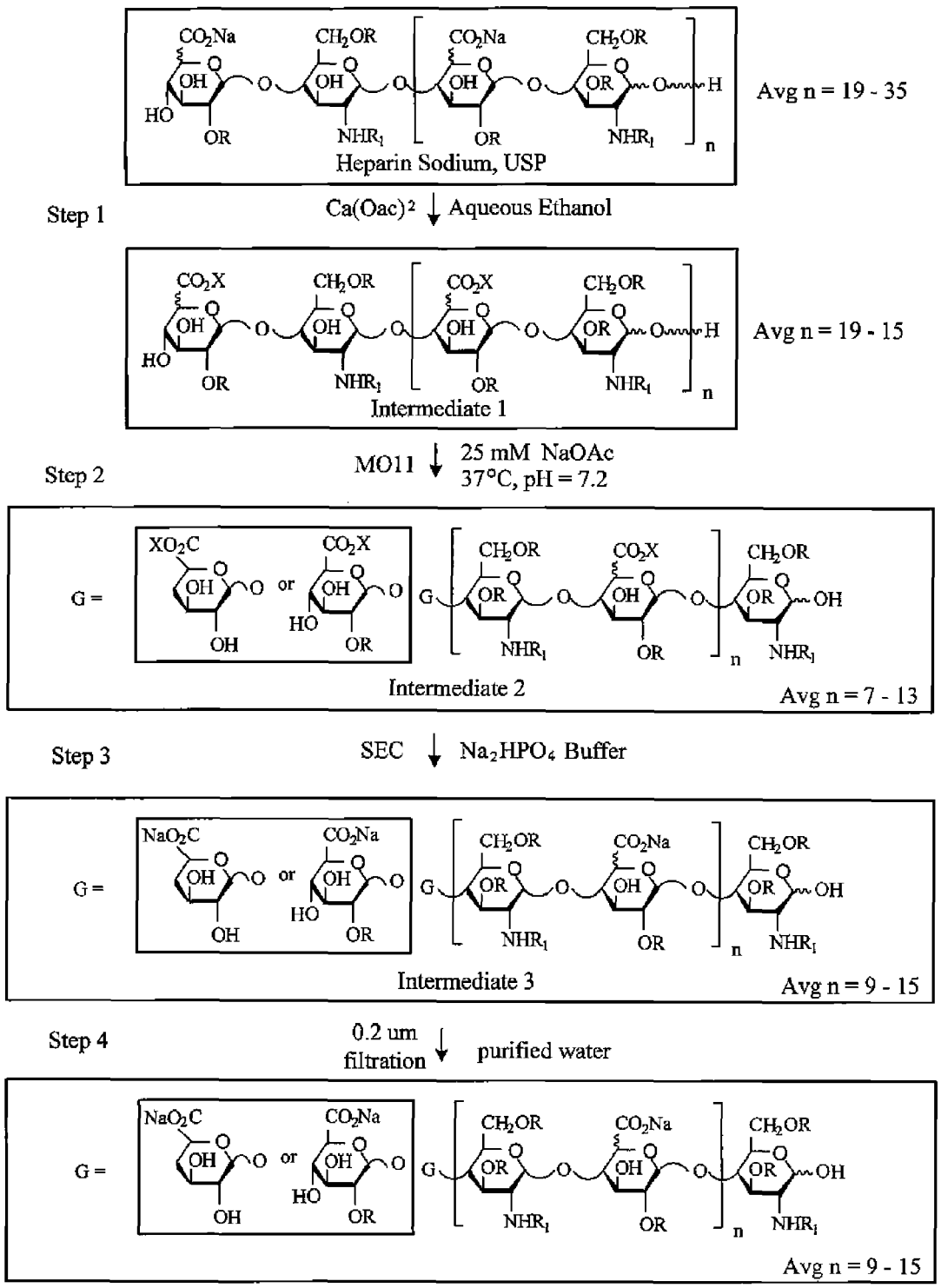
FIG. 1 is a flow chart depicting the four steps of manufacturing process of M118-REH.

In many clinical settings, commercially available LMWH preparations are preferred over UFH preparations because LMWHs have more predictable pharmacokinetics and can be administered subcutaneously. However, currently available LMWH preparations lack many of the desirable properties of UFH such as substantial anti-IIa activity, reversibility (or neutralizability) with protamine sulfate and monitorability. Thus, there are clinical settings where LMWHs are not an optimal or practical treatment choice. The invention features LMWH preparations designed to have properties that are clinically advantageous, e.g., over other commercially available LMWH preparations and UFH preparations. Such properties include, e.g., one or more of: reversibility with proteomine sulfate; predictable pharmacokinetics, anti-IIa activity; substantially constant anti-Xa activity to anti-IIa activity ratio; monitorable activity levels by standard tests such as, e.g., ACT or aPTT; subcutaneous bioavailability; and reduced occurrence of HIT.

Anti-IIa Activity

LMWH preparations are disclosed herein that include a significant number of chains of sufficient length (which can be described, e.g., in terms of average chain length of the preparation and/or weight average molecular weight of the preparation) to provide anti-IIa activity, e.g., anti-IIa activity of about 50 to 300 IU/mg, about 70 to 280 IU/mg, about 90 to 250 IU/mg, about 100 to 140 IU/mg, about 100 to 140 IU/mg, about 150 to about 200 IU/mg, about 130 to 190 IU/mg, about 155 to 195 IU/mg. Anti-IIa activity is calculated in International Units of anti-IIa activity per milligram using the statistical methods for parallel line assays. The anti-IIa activity levels described herein are measured using the following principle.

M118+ATIII→[M118·ATIII]

IIa

M118·ATIII→[M118·ATIII·IIa]+IIa (Excess)

IIa (Excess)+Substrate→Peptide+pNA (measured spectrophotometrically)

Anti-factor IIa activity is determined by the sample potentiating effect on antithrombin (ATIII) in the inhibition of thrombin. Thrombin excess can be indirectly spectrophotometrically measured. The anti-factor IIa activity can be measured, e.g., on a Diagnostica Stago analyzer or on an ACL Futura™ Coagulation system, with reagents from Chromogenix (S-2238 substrate, Thrombin (53nkat/vial), and Antithrombin), or on any equivalent system. Analyzer response is calibrated using the 2nd International Standard for Low Molecular Weight Heparin.

Chain Length/Molecular Weight

A determination of whether a LMWH preparation includes chains of sufficient chain length can be made, for example, by determining the average chain length of the chains in the LMWH preparation and/or by determining the weight average molecular weight of chains within the LMWH preparation. When average chain length is determined, an average chain length of about 5 to 20, e.g., 7 to 18, preferably about 9 to 16 or 8 to 14 disaccharide repeats, indicates that a significant number of chains in the LMWH preparation are of sufficient chain length.

"Average chain length" as used herein refers to the average chain length of uronic acid/hexosamine disaccharide repeats that occur within a chain. The presence of non-uronic acid and/or non-hexosamine building blocks (e.g., attached PEG moieties) are not included in determining the average chain length. Average chain length is determined by dividing the number average molecular weight (Mn) by the number average molecular weight for a disaccharide (500 Da). Methods of determining number average molecular weight are described below using SEC MALS.

Examples of such LMWH preparations include the following:

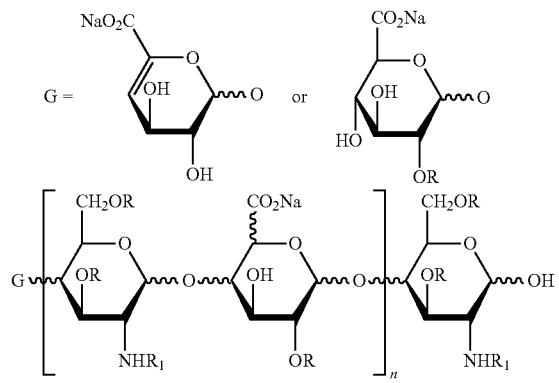

wherein R is H or $SO_3X$;
R1 is $SO_3X$ or $COCH_3$ and X is a monovalent or divalent cation (e.g., Na or Ca);
and average n is about 9 to 16 or 8 to 15;

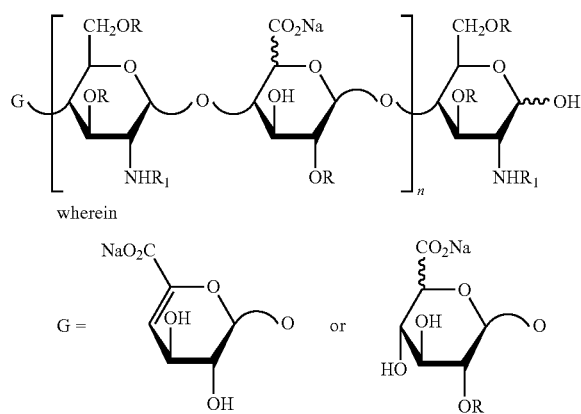

wherein

R is H or $SO_3X$;
R1 is $SO_3X$ or $COCH_3$, X is a monovalent or divalent cation (e.g., Na or Ca);
and average n is about 9 to 16 or 8 to 15;

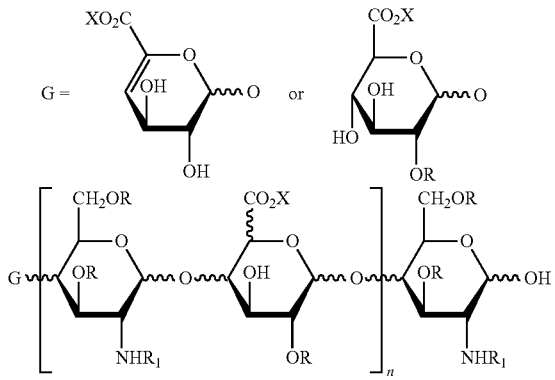

wherein,
X is a monovalent or divalent cation (e.g., Na or Ca);
R is H or $SO_3X$;
R1 is $SO_3X$ or $COCH_3$; and
average n is about 8 to 12 or 7 to 11; and

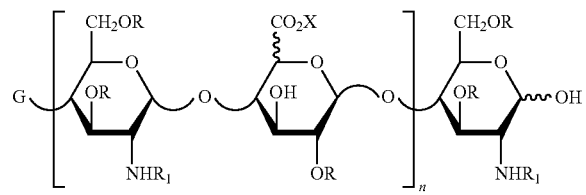

wherein,
X is a monovalent or divalent cation (e.g., Na or Ca);
R is H or $SO_3X$;
R1 is $SO_3X$ or $COCH_3$;
average n is 8 to 12 or 7 to 11, and

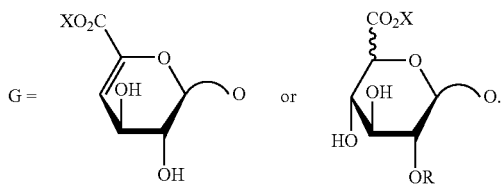

When weight average molecular weight of a preparation is determined, a weight average molecular weight of about 5000 to 9000 Da, about 5000 to 8300 Da, preferably about 5500 to 8000 Da, about 5700 to 7900, or about 5800 to 6800 Da, indicates that a significant number of chains in the LMWH preparation are of sufficient chain length.

"Weight average molecular weight" as used herein refers to the weight average in daltons of chains of uronic acid/hexosamine disaccharide repeats. The presence of non-uronic acid and/or non-hexosamine building blocks are not included in determining the weight average molecular weight. Thus, the molecular weight of non-uronic acid and non-hexosamine building blocks within a chain or chains in the preparation should not be included in determining the weight average molecular weight. The weight average molecular weight ($M_w$) is calculated from the following equation: $M_w = \Sigma(c_i m_i)/\Sigma c_i$. The variable ci is the concentration of the polymer in slice i and Mi is the molecular weight of the polymer in slice i. The summations are taken over a chromatographic peak, which contains many slices of data. A slice of data can be pictured as a vertical line on a plot of chromatographic peak versus time. The elution peak can therefore be divided into many slices. The weight average molecular weight calculation is average dependant on the summation of all slices of the concentration and molecular weight. The weight average molar weight can be measured, e.g., using the Wyatt Astra software or any appropriate software. The weight average molecular weights described herein are determined by high liquid chromatography with two columns in series, for example a TSK G3000 SWXL and a G2000 SWXL, coupled with a multi angle light scattering (MALS) detector and a refractometric detector in series. The eluent used is a 0.2 sodium sulfate, pH 5.0, and a flow rate of 0.5 mL/min.

Non-Reducing End Structure

In addition to chain length about 5 to 15 mole %, 7 to 14 mole %, or 9 to 12 mole % of the chains in a preparation can have $\Delta UH_{NAc,6S}GH_{NS,3S,6S}$ at, or within about two, four or six monosaccharides from the non-reducing end of the chain. Methods that can be used to quantify this structure include, e.g., capillary electrophoresis (CE) and high performance liquid chromatography (HPLC), e.g., reverse phase high performance liquid chromatography (RPHPLC). To quantify the mole % of $\Delta UH_{NAc,6S}GH_{NS,3S,6S}$ in a LMWH preparation, a response factor (RF) for $\Delta UH_{NAc,6S}GH_{NS,3S,6S}$ can be determined. The determination can also include determining the RF for all species obtained, e.g., using CE or HPLC, e.g., a CE method described herein. To obtain the RF for a species or all species obtained by CE, e.g., a CE method described herein, known concentrations of a standard for the specie or one or more of the species can be injected on the CE and used to determine a RF for each. The RF can then be used to determine the mole %. As described herein, the sample has an actual level of a structure, which can be expressed, e.g., as 5 to 15 when described in units of mole %. That actual level can also be expressed in other units, e.g., weight %. That actual level is the same regardless of the units in which it is expressed. The specification of mole % in the method is merely to indicate the actual prevalence of the structure. The level of structure can be measured in terms of other units and the reference value can be expressed in terms of other units, as long as the reference value as expressed in terms of alternative units corresponds to the same amount of structure as the reference value expressed in mole %, 5 to 15 mole % in this example. Thus, a method which requires showing the structure is present at 5 to 15 mole % can be performed by showing that the structure is present in a range expressed in an alternative unit of measure, e.g., weight %, chain number, or % AUC, wherein the range, as described in the alternative unit of measure, corresponds to the same amount of the structure which would give the mole % referred to, in this example 5 to 15 mole %.

A LMWH preparation described herein can have a mixture of $\Delta U$ and iduronic acid (I)/glucuronic acid (G) at the non-reducing end of the chains in the preparation. The nomenclature "$\Delta U$" refers to an unsaturated uronic acid (iduronic acid (I), glucuronic acid (G) or galacturonic acid) that has a double bond introduced at the 4-5 position as a result, e.g., of the lyase action of a heparinase, a HSGAG lyase, or other enzyme having similar substrate specificity. Preferably, about 15% to 35%, 20 to 30% (e.g., 15%, 20%, 25%, 30%, 35%) of the total number of chains in the preparation have a $\Delta U$ at the non-reducing end of the chain. The quantity of ΔU and/or I/G at the non-reducing end of chains within the sample can be determined using, e.g., 2D-NMR. In such methods, the total number of chains having an acetylated hexosamine ($H_{NAc}$) at the reducing end and/or the number of open ring confirmations at the reducing end can be used to determine the total number of chains within the preparation. The total percentage of chains having a ΔU and/or I/G at the non-reducing end can be compared to the total number of chains in the preparation. Preferably, in the LMWH preparations described herein, less than 90%, 95%, 98%, 99% or none of the chains in the preparation have a sulfated ΔU at the non-reducing end.

Reducing End Structures

In some instances, a LMWH preparation provided herein has substantially no modified reducing end structures. In preferred embodiments at least 85%, 90%, 95%, 98%, 99% or all of the chains in the LMWH preparation have a non-modified reducing end structure.

A "modified reducing end structure" refers to a structure that arises at the reducing end of chains in the preparation due to the process of isolating or preparing the preparation from natural sources. For example, many commercially available LMWH preparations are derived from unfractionated heparin primarily through chemical or enzymatic depolymerization of the polysaccharide chains. A process used to make a LMWH can cause one or more unique structural modifications to the reducing end of polysaccharide chains of starting material from a natural source. For example, nitrous acid depolymerization of heparin results in the formation of a 2,5-anhydromannose at the reducing end, which can be reduced to form an alcohol, and depolymerization through esterification of the carboxylate functional group on the uronic acid followed by β-elimination results in the formation of a 1,6-anhydro structures at the reducing end of some chains. Thus, 2,5-anhydromannose and 1,6 anhydro structures are examples of modified reduce end structures that can be found on some chains of LMWHs. The chains in a LMWH preparation provided herein can include, e.g., at least about 60%, 70%, 80%, 85%, 90%, 95%, 98%, 99% or all of the chains having an acetylated hexosamine at the reducing end.

Anti-Xa Activity

Anti-Xa activity of a LMWH preparation plays a role in biological activity of LMWH preparations. Preferably, a LMWH preparation provided herein has an anti-Xa activity of about 100 to 400 IU/mg, e.g., about 120 to 380 IU/mg, e.g., about 150 to 350 IU/mg, e.g., about 170 to 330 IU/mg, e.g., about 180 to 300 IU/mg, e.g., about 150 to 200 IU/mg, 200 to 300 IU/mg. Anti-Xa activity of a LMWH preparation is calculated in International Units of anti-factor Xa activity per milligram using the statistical methods for parallel line assays. The anti-factor Xa activity of LMWH preparations described herein is measured using the following principle:

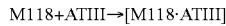

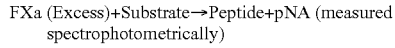

The anti-factor Xa activity is determined by the sample potentiating effect on antithrombin (ATIII) in the inhibition of activated Factor Xa (FXa). Factor Xa excess can be indirectly spectrophotometrically measured. Anti-factor Xa activity can be measured, e.g., on a Diagnostica Stago analyzer with the Stachrom® Heparin Test kit, on an ACL Futura™ Coagulation system with the Coatest® Heparin Kit from Chromogenix, or on any equivalent system. Analyzer response can be calibrated using the NIBSC International Standard for Low Molecular Weight Heparin.

Anti-Xa/IIa Ratio

In some aspects, LMWH preparations provided herein have an anti-Xa activity to anti-IIa activity ratio of 3:1 or less, e.g., 2.1, 1.6:1, 1.5:1, 1.4:1, 1.3:1, 1.2:1, 1.1:1, 1:1. Methods of determining anti-factor Xa activity and the anti-factor IIa activity have been described above. The ratio of anti-factor Xa activity to anti-factor IIa activity is calculated by dividing anti-factor Xa activity (dry basis) by the anti-factor IIa activity (dry basis).

Both anti-Xa activity and anti-IIa activity of heparin and LMWH preparations involve binding of antithrombin III (ATIII) to a specific sequence, represented by the structure $\Delta UH_{NAc,6S}GH_{NS,3S,6S}$, within chains present in the preparation. Binding of ATIII to this sequence mediates anti-Xa activity. In addition, thrombin (factor IIa) binds heparins at a site proximate to the ATIII binding site. Unlike anti-Xa activity that requires only the ATIII binding site, anti-IIa activity requires the presence of an ATIII binding site as well as a chain of sufficient length distal to the ATIII binding site. The anti-IIa activity of LMWH preparations provided herein can be attributed, at least in part, to the presence of $\Delta UH_{NAc,6S}GH_{NS,3S,6S}$ at or near the non-reducing end of chains within the LMWH preparations as well as the length of many of the chains present in the preparation. This combination may result in chains within the preparation that contribute to both anti-Xa activity and anti-IIa activity. When both anti-Xa activity and anti-IIa activity are provided by the same chain or chains, the clearance of that chain or chains can result in both a decrease in anti-Xa activity and anti-IIa activity. As such, the anti-Xa activity and anti-IIa activity can remain relatively constant over the course of administration. Therefore, in some aspects, the LMWH preparations provided herein have an anti-Xa activity to anti-IIa activity remains relatively constant over the course of an administration of LMWH, e.g., the anti-Xa activity to anti-IIa activity ratio varies about ±1.5, ±1, ±0.5, or ±0.2, over a period of about 30, 60, 120, 180, 240, 300 minutes. For example, if an initial ratio of anti-Xa activity t anti-IIa activity is 2, then the ratio measured at a second time (e.g., 30, 60, 120, 180, 240, 300 minutes) after the initial administration will preferably be less than 3, and preferably at or around 2.

Neutralization

LMWH preparations provided herein can be neutralized by protamine sulfate. For example, anti-IIa activity and/or anti-Xa activity can be neutralized by at least 50%, 60%, 70%, 80%, 85%, 90%, 95%, 99% or 100% by administration of protamine. Protamine sulfate is commercially available, e.g., from Eli Lilly and Company. Neutralization of anti-Xa activity and anti-IIa activity can be measured, e.g., by standard coagulation assays such as ACT and aPTT, both of which are described further herein. Protamine sulfate can be administered intravenously, e.g., at a dose of about 1, 2, 3 mg per 100 anti-Xa IU of the LMWH preparation in plasma. Preferably, protamine neutralization of anti-Xa activity and/or anti-IIa activity occurs within 5, 10, 15, 20, 25, or minutes after administration of the protamine sulfate.

Polydispersity

The polydispersity of LMWH preparations provided herein is about 1.6 or less, e.g., about 1.6 or 1.5 to 1.1, and numbers in between.

The term "polydisperse" or "polydispersity" refers to the weight average molecular weight of a composition (Mw) divided by the number average molecular weight (Mn). The number average molecular weight (Mn) is calculated from the following equation: $Mn=\Sigma ci/(\Sigma ci/ml)$. The variable ci is the concentration of the polysaccharide in slice i and Mi is the molecular weight of the polysaccharide in slice i. The summations are taken over a chromatographic peak, which contains many slices of data. A slice of data can be pictured as a vertical line on a plot of chromatographic peak versus time. The elution peak can therefore be divided into many slices. The number average molecular weight is a calculation dependent on the molecular weight and concentration at each slice of data. Methods of determining weight average molecular weight are described above, and were used to determine polydispersity as well.

For any of the ranges described herein, e.g., for a given structure or activity, the ranges can be those ranges disclosed as well as other ranges. For example, a range constructed from a lower endpoint of one range, e.g., for a given building block or activity, can be combined with the upper endpoint of another range, e.g., for the given building block or activity, to give a range.

An "isolated" or "purified" LMWH preparation is substantially free of cellular material or other contaminating proteins from the cell or tissue source from which the LMWH is derived, or substantially free from chemical precursors or other chemicals when chemically synthesized. "Substantially free" means that a preparation of LMWH is at least 50% pure (wt/wt). In a preferred embodiment, the preparation of LMWH has less than about 30%, 20%, 10% and more preferably 5% (by dry weight), of non-heparin polysaccharides, proteins or chemical precursors or other chemicals, e.g., from manufacture. These also referred to herein as "contaminants". Examples of contaminants that can be present in a LMWH preparation provided herein include, but are not limited to, calcium, sodium, heparinase enzyme (or other enzyme having similar substrate specificity), methanol, ethanol, chloride, sulfate, dermatan sulfate, and chondrotin sulfate.

Methods of Monitoring Activity of a LMWH Preparation

The activity of a LMWH preparation provided herein can be monitored by standard anti-coagulation assays. Such assays include, e.g., ACT and aPTT, both of which are routinely practiced in hospitals and specifically hospital operating rooms.

ACT is a test that is used to monitor the effectiveness of heparin therapy. The ACT can be done at the bedside, e.g., for patients experiencing pulmonary embolus, extracorporeal membrane oxygenation (ECMO) and hemodialysis. ACT is most often used before, during and after surgical intervention such as, e.g., cardiopulmonary bypass (CPB) surgery, PCI and stent placement. Reference value for the ACT can range from between 70-180 seconds. However, for certain procedures such as CPB the desired range can exceed 400-500 seconds. ACT utilizes negatively charged particles for a determination of time to clot formation. Examples of various particles that can be used include celite, which has a normal length of ACT being about 100 to 170 seconds; kaolin, which has a normal length of ACT being about 90 to 150 seconds; and glass particles, which have a normal length of ACT being about 190 to 300 seconds. Suitable machines for measuring ACT include, e.g., Hemochron and Medtronic HemoTec.

In the aPTT (also referred to as "partial thromboplastin time" or "PTT") test, a contact activator is used to stimulate the production of Factor XIIa by providing a surface for the function of high molecular weight kininogen, kallikrein and Factor XIIa. This contact activation is allowed to proceed for a specific period of time. Calcium is then added to trigger further reactions and the time required for clot formation is measured. Phospholipids are required to form complexes, which activate Factor X and Prothrombin. APTT can be measured by the IL Test™ APTT-SP(liquid). Reference values for aPTT is about 25 to 35 seconds. A prolonged aPTT indicates that clotting is taking longer than expected, e.g., due to a heparin or LMWH treatment.

Methods of Making LMWH Preparations.

Various methods of making LMWH preparations, e.g., a LMWH preparation described herein are also contemplated. For example, such methods include a method of making a LMWH preparation having an average chain length of about 8 to 16 or 9 to 16 disaccharides. The method includes providing a precursor LMWH preparation having a chain length of less than 8 to 16 or 9 to 16 disaccharides, and processing the precursor LMWH preparation to obtain a LMWH preparation having an average chain length of about 8 to 16 or 9 to 16 disaccharides. Preferably, the precursor has an average chain length of about 8 to 14, e.g., 8 to 12, disaccharides. For example, the precursor LMWH preparation can have the following structure:

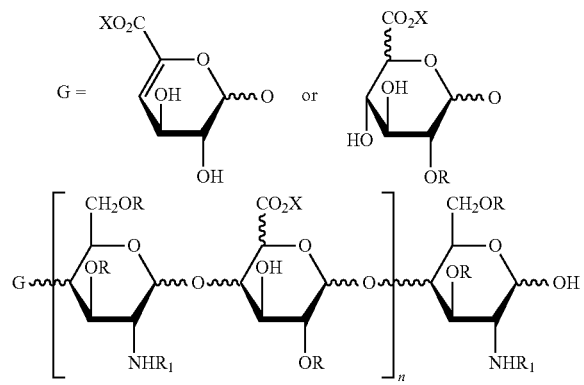

wherein X is a monovalent or divalent cation (e.g., Na or Ca), R is H or $SO_3X$;
R1 is $SO_3X$ or $COCH_3$;
n=2-45, e.g., 2-35;
and the composition preferably has an average value for n of 7 to 13, e.g., 7 to 11, or 8 to 12.

A precursor LMWH preparation used in this method can be obtained by a method that includes salt precipitation followed by (and) enzymatic digestion. A salt of a monovalent or divalent cation can be used in the method of obtaining the precursor LMWH preparation. Examples of monovalent and divalent cations that can be used include, e.g., sodium, potassium, rubidium, cesium, barium, calcium, magnesium, strontium, and combinations thereof. The salt can be, e.g., an acetate of a monovalent or divalent cation. Enzymatic digestion to obtain the LMWH precursor can include the use of one or more enzymes that cleaves at one or more glycosidic linkages of unsulfated uronic acids. Exemplary enzymes include heparinase III, mutants of heparinase III and HSGAG lyase III from *Bacteroides thetaiotaomicron*. Heparinase III is described, for example, in U.S. Pat. Nos. 5,681,733 and 5,919,693. Mutants of heparinase III are described in U.S. Pat. No. 5,896,789. Preferred heparinase III mutants are those mutants having one or more histidine at His36, His105, His110, His139, His152, His225, His234, His424, His469 and His539 substituted with an alanine.

The precursor LMWH preparation can be processed by size dependent separation such as, e.g., size exclusion chromatography, ion exchange chromatography and filtration.

Further processing steps can be used prior to or after the size dependant separation, e.g., to obtain drug product.

The term "drug product" refers to a LMWH preparation having the purity required for and being formulated for pharmaceutical use.

The term "drug substance" refers to a LMWH preparation having the polysaccharide constituents for pharmaceutical use but is not necessarily in its final formulation and/or comprises one or more non-product contaminant (e.g., one or more inorganic product such as sulfate, chloride, protein contaminant, process by-product such as heparinase, calcium, sodium).

Other methods of making a LMWH preparation as provided herein includes providing a "fast moving fraction" from a glycosaminoglycan (GAG) containing sample, e.g., UFH. The fast moving fraction can be made as follows:

(1) subjecting a GAG containing sample, e.g., UFH, to a first a precipitation, e.g., with a polar organic solvent (e.g., an alcohol, e.g., ethanol), a polar non-organic solvent (e.g., water), and a salt (preferably, a sodium salt, e.g., sodium acetate), to yield a first supernatant;

(2) subjecting the first supernatant to a second precipitation, e.g., with a polar organic solvent (e.g., an alcohol, e.g., ethanol), and a polar non-organic solvent (e.g., water), to yield a precipitate (this precipitate contains the fast moving fraction);

(3) and preferably solublizing the precipitate.

Fractions of (GAG) containing sample, e.g., UFH made by other methods, but which produce a substantially equivalent fraction, e.g., one having an average chain length of 9-16 disaccharides can also be used as a fast moving fraction.

In some embodiments, the fast moving fraction has the following structure:

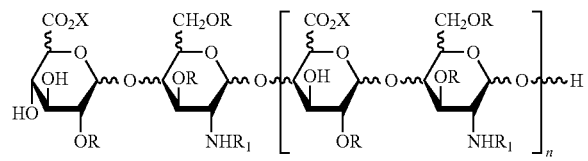

wherein,
X is Na or Ca;
R is H or $SO_3Na$;
R1 is $SO_3Na$ or $COCH_3$;
n=2-50, e.g., 2-40;
and the composition preferably has an average value for n of 9 to 16 or 8 to 15.

This composition can occur as an intermediate in the production of a LMWH, e.g., as the product of precipitations to provide a fast moving fraction (as discussed herein).

The fast moving fraction can be processed further to provide a LMWH of the invention. Processing of the fast moving fraction can include digesting the fast moving fraction with a chemical or enzyme that cleaves one or more glycosidic linkages of unsulfated uronic acid, e.g., one or more glycosidic linkages of unsulfated uronic acid adjacent to an N-acetyl glucosamine residue, e.g., to give rise to a preparation with the qualities and characteristics described herein. Enzymes can be evaluated for substrate specificity by the following steps: 1) functional screening of enzyme activity against two HSGAG substrates having different sulfation densities, e.g., heparin and heparan sulfate, whereby enzymes having a preference for heparan sulfate over heparin are selected; 2) fragment mapping of cleaved substrates from step 1 to assess substrate specificity; 3) cleavage of a LMWH such as M118-REH step 1 intermediate or dalteparin using the enzyme, followed by; 4) assessment of anti-Xa activity and anti-IIa activity of the cleaved substrate using an in vitro assay; and 5) assessment of molecular weight distribution (or average chain length) of cleaved substrate using gel permeation chromatography (GPC) and/or size exclusion chromatography interfaced with multi-angle light scattering (SEC-MALS).

Step 1 assesses an enzyme's ability to act as an HSGAG lyase identified by the ability to generate an unsaturated C4-C5 bond at non-reducing ends of cleavage products as well as the enzymes preference for undersulfated substrates such as heparan sulfate. Enzyme activity can be followed spectrophotometrically by monitoring UV absorbance at 232 nm. An absorbance at this wavelength indicates formation of unsaturated uronic acids at the non-reducing ends of the cleavage product. Enzyme activity is monitored both kinetically (initial rate of product formation) and in terms of total product formation following exhaustive digestion (about 12 to 15 hours). Preferred enzymes have about a two fold preference for heparan sulfate over heparin and greater than a two fold (e.g., a 3 to 5 fold) difference in total activity.

The second step assesses the cleavage specificity of the enzyme. Enzymes suitable for making the LMWH compositions described herein preferentially cleave undersulfated regions of heparin or heparan sulfate. If UFH is the substrate used, this preference is demonstrated by an obvious underdigestion of substrate (as indicated by the presence of longer oligosaccharides) with any disaccharides being produced having a low sulfate density. In contrast when the substrate is heparan sulfate, digestion results in a greater number of disaccharides which indicates a higher cutting frequency.

The remaining steps 3-5 can be performed as described elsewhere herein.

Examples of enzymes include heparinase III, mutants of heparinase III and HSGAG lyase from *Bacteroides thetaiotaomicron*. In some embodiments, the fast moving fraction is processed, at least in part, with a mutated heparinase III having an alanine at residue 225 of the amino acid sequence of heparinase III instead of a histidine. This enzyme is also referred to herein as "MO11".

The digested LMWH preparation can be the final product, e.g., the drug substance or drug product, or can be further processed to obtain the final product, e.g., drug substance or drug product. The concentrated LMWH preparation can be further processed, e.g., by one or more of size dependant separation (e.g., by size exclusion chromatography, ion exchange chromatography and filtration), and filtration. Preferably, the concentrated LMWH preparation is further processed by a size dependant separation, and the LMWH preparation obtained from this step has an average chain length of about 9 to 16 disaccharides.

Methods of Evaluating or Processing LMWH Preparations
Capillary Electrophoresis
Enzymes Analysis of a LMWH preparation such as an M118-REH preparation using CE includes, e.g., digesting the preparation with one or more heparin degrading enzymes. The heparin degrading enzyme(s) can be, e.g., one or more heparinase, heparin lyase, HSGAG lyase, a lyase described as a GAG lyase that can also degrade heparin, and/or any polypeptide described as a hydrolase, sulfatase/sulfohyrdolase, or glycosyl hydrolase/glycosidase. For example, the LMWH preparation can be digested with one or more of: an unsaturated glucuronyl hydrolase (e.g., *F. heparinum* Δ4,5 glycuronidase, *B. thetaiotaomicron* Δ4,5 glycuronidase); a glucuronyl hydrolase (e.g., mammalian α-iduronidase, β-glucuronidase); a sulfohydrolase (e.g., *F. heparinum* 2-O-sulfatase, 6-O-sulfatase, 3-O-sulfatase, *B. thetaiotaomicron* 6-O-sulfatase, a mucin desulfating enzyme, mammalian N-acetylglucosamine-6-sulfatase, mammalian iduronic acid-2-sulfatase); a N-sulfamidase (e.g., *F. heparinum* N-sulfamidase, mammalian heparan-N-sulfatase); an arylsulfatase; a hexosaminidase; a glycosyl hydrolase (e.g., endo-N-acetyl glucosaminidase); a heparinase (e.g., *Flavobacterum heparinum* heparinase I, *Flavobacterum heparinum* heparinase II, *Flavobacterum heparinum* heparinase III, *Flavobacterum heparinum* heparinase IV); an endoglucoronidase (e.g., mammalian heparanase); a heparin/heparan sulfate lyase (e.g., *Bacteroides thetaiotaomicron* HSGAG lyase I, *Bacteroides thetaiotaomicron* HSGAG lyase II, *Bacteroides thetaiotaomicron* HSGAG lyase III, *Bacteroides thetaiotaomicron* GAG lyase IV); and functional fragments and variants thereof. It can also include a polypeptide described as above (e.g., a heparinase or a heparin/heparin sulfate lyase) derived from microorganisms other than *Flavobacterium heparinum* (a.k.a. *Pedobacter heparinus*) or *Bacteroides thetaiotaomicron*. For example, *Haloarcula marismortui*, *Agrobacterium tumefaciens*, *Streptococcus pneumoniae*, *Streptococcus pneumoniae*, *Streptococcus pyogenes*, *Streptococcus agalactiae*, *Streptococcus intermedius*, *Streptococcus suis*, *Enterococcus faecalis*, *Rhodopseudomonas palustris*, *Nitrobacter winogradskyi*, *Nitrobacter hamburgensis*, *Bradyrhizobium japonicum*, *Rhizobium meloliti*, *Mesorhizobium loti*, *Spinghobacterium* sp., *Brucella abortus biovar*, *Brucella melitensis*, *Solibacter usitatus*, *Acidobacterium capsulatum*, *Microbulbifer degradans*, *Pseudomonas aeruginosa*, *Burkholderia pseudomonascepacia*, *Geobacter metallireducens*, *Prevotella* sp., *Serrata marcescens*, *Cornybacterium* sp., *Anaeromyxobacter dehalogenans*, *Rhodopirellula baltica*, *Pirellula marina*, and/or *Gemmata obscuriglobus*.

Preferably, at least one enzyme used in the digestion is selected because it cleaves at specific linkages within heparins. For example, the enzyme can be heparinase I and/or HSGAG lyase I. In one embodiment, the LMWH preparation is digested with *Flavobacterium heparinum* heparinase I. In other embodiments, the heparin preparation is digested with *Bacteroides thetaiotaomicron* HSGAG lyase I.

Other enzymes can be selected for use in the digestion which resolve structures which could not be resolved solely with the use of heparinase I, II, and III. Any of the enzymes described herein can be replaced with an enzyme with functionally equivalent activity.

In a preferred embodiment, the digestion is run to completion or at least sufficiently to provide a digest having all of the products found in Table 10A and preferably substantially free of undigested material.

Prior to digestion, the sample can be lyophilized. For example, the sample can be dried in a vacuum oven, e.g., at about 20° C., 25° C., 30° C., 35° C., 40° C., 43° C., 46° C., 49° C., 52° C., or 55° C., for about 2, 4, 6, 8, 10, 12, 14, 16, 18, 20, 22, or 24 hours. For example, the sample can be lyophilized and/or dried under one of the following conditions: For example, the sample can be lyophilized and/or dried under one of the following conditions: 40° C. for 12 hours; 46° C. for 8 hours; 49° C. for 6 hours; 52° C. for 4 hours. A sample can be suspended in water or a suitable buffer (e.g., 1 mM calcium acetate, 25 mM sodium acetate, pH 7.0, and 5% glycine) at a concentration of about 1, 2, 5, 10, 20, 50, 100, 200, or 500 mg/mL. One or more heparin degrading enzyme can be added to the sample. In some embodiments, heparinase I or HSGAG lyase I (or combinations of these enzymes), heparinase II or HSGAG lyase II (or combinations of these enzymes), and heparinase III or HSGAG lyase III (or a combination of these enzymes) are added to the sample. The sample is digested at a temperature of about 18° C., 25° C., 30° C., 37° C., or 45° C. for about 6, 12, 16, 18, 20 or 24 hours, e.g., at about 25° C. for 24 hours; at 30° C. for about 18 hours; at about 37° C. for 12 hours.

Following digestion, the enzyme or enzymes are removed from the sample mixture, e.g., using a $Ni^{2+}$ column, a size-exclusion column, dialysis, ultrafiltration, or the like. The enzyme or enzyme can be inactivated by heating (e.g., at 65° C. for 20 minutes) following digestion. The sample can be stored, e.g., at −85° C., −70° C., −20° C., 4° C., 18° C., or 25° C. for a period of time prior to analysis.

Species separated by the methods described herein can be detected by numerous means, e.g., by ultraviolet absorbance (e.g., at a wavelength of about 232 nm), evaporative light scattering, fluorescence, pulsed amperometric detection, and mass spectrometry. In some embodiments, two or more means of detection can be utilized on the same sample, e.g., in series or in parallel.

Additional enzyme digestions can be used to digest the sample. For example, a combination of heparinase I or HSGAG lyase I (or combinations of these enzymes), heparinase II or HSGAG lyase II (or combinations of these enzymes), heparinase III or HSGAG lyase III (or a combination of these enzymes), and 2-O sulfatase, Δ4,5 glycuronidase, and/or heparinase I or HSGAG lyase I (or combinations of these enzymes), heparinase II or HSGAG lyase II (or combinations of these enzymes), heparinase III or HSGAG lyase III (or a combination of these enzymes), can be used for digestion, and, e.g., detected by the methods described above.

The digestion products are analyzed using an Agilent 3D Capillary Electrophoresis instrument. The capillary is an extended light path bare fused-silica capillary 75 μm ID, effective length 72 cm. Tris (50 mM), 10 μM dextran sulfate at pH 2.5 is used as CE buffer. Samples are injected at a pressure of 30 mbar for 20 seconds. Separation is performed at negative polarity and the analyte is monitored at 232 nm with 310 nm as the reference wavelength. New capillaries are pre-treated with a sequence of water, 1N sodium hydroxide, water, and separation buffer. For each sample analysis, the capillary is preconditioned with buffer for 5 minutes.

Additional information useful for the methods described herein can be found in, e.g., Linhardt et al. (1988) Biochem. J., 254:781-787; Chuang et al. (2001) J. Chromatogr. A, 932: 65-74; and Yates et al. (2004) J. Med. Chem., 47:277-280, and Rhomberg et al. (1988) Proc Natl Acad Sci USA. 95(8):4176-81.

Capillary Electrophoresis

CE, using e.g., an uncoated fused silica capillary, can be used to analyze LMWH, e.g., LMWH preparations described herein. Under conditions of low pH, separation is dictated by analyte electrophoretic mobility almost exclusively. Due to the fact that all LMWH related saccharides have a net negative charge due to the carboxylate and sulfate moieties, separation is conducted under reverse polarity. In addition, supplementation of the low pH (pH2.5) buffer with dextran sulfate prevents non-specific absorption of anionic heparin-like material, enabling symmetrical peaks shapes and accurate quantification.

The species in LMWH preparation can be resolved with a series of five digests (discussed in detail elsewhere herein); each digest is subjected to capillary electrophoresis after addition of an internal standard naphthalene monosulfonate.

14 individual components (see, e.g., Table 10, herein) are resolved in the CE.

Mass recovery in the compositional analysis methodology was evaluated as follows. This analysis occurred at two levels: (1) mass recovery after enzymatic digestion and (2) mass recovery after separation with capillary electrophoresis.

NMR

Two dimensional nuclear magnetic resonance spectroscopy (2D NMR) can be used as a means of partially resolving and identifying signals with minimum signal overlap. Integration of the 2D NMR signals followed by simple calculations can facilitate a quantitative monosaccharide compositional analysis of a polysaccharide mixture such as analysis of a LMWH preparation such as those provided herein.

Moreover, 2D NMR can provide information on linkage environments of a disaccharide constituent, for example an H-U disaccharide, providing analysis of disaccharide linkages, including both qualitative and quantitative analysis. In some embodiments, 2D NMR analysis can provide information about the epimerization state of a H-U linkage, for example, providing information as to whether the epimerization state is an iduronic acid residue or an glucuronic acid residue (i.e., I or U).

In some embodiments, a 2D proton-carbon correlation spectroscopy (HSQC) experiment can provide quantitative compositional analysis on one or more glycosaminoglycan. For example, in some embodiments 2D NMR analysis can provide information about the nearest neighbor at the reducing end of a monosaccharide. This information can provide, for example, the sequence context in which a particular monosaccharide is present in a polysaccharide mixture, e.g., a LMWH such as a LMWH preparation described herein.

In some embodiments, 2D NMR method allows to discriminate between internal and reducing end residues. In particular, identification of measurable amounts of reducing N-acetyl glucosamine is peculiar of those LMWH described herein.

In some embodiments, 2D NMR analysis can provide information about the non-reducing end of LMWH chains, i.e. the amount of ΔUAp2-OH generated by the enzymatic digestion.

In some embodiments, 2D NMR can be used to evaluate a polysaccharide mixture for the presence of one or more impurities such as dermatan sulfate. For example, the absence of a signal in the proton NMR at 2.06-2.09 ppm can be used to confirm that dermatan sulfate is not present at levels greater than the level of detection of the instrument (e.g., at a level greater than about 1%).

In a preferred embodiment saccharide structure is evaluated using, 2D NMR, e.g., e.g., sample of a polysaccharide mixture exchanged with D2O, lyophilized over night, and redissolved in D2O. The sample is then placed in an NMR tube for analysis and run at 303 K with a Bruker Avance 600 MHz spectrometer equipped with a 5-mm TXI probe. Gradient-enhanced HSQC spectra is recorded with carbon decoupling during acquision. The data is then acquired with 16 scans for each of 256 increments in the indirect 13C dimension. The polarization transfer delay is set to 2.941 ms for an optimal transfer with 1JCH scalar couplings of 155 Hz.

The data is generally then processed, e.g. the matrix size 1K×256 is zero filled to 2K×1K by application of a squared-cosine function prior to Fourier transformation. Cross peaks are integrated, for example, using MestreC 4.5 software and only positive peaks are used for integration. Integrals are normalized to the H2/C2 peak of N-sulfated glucosamine (3.26/60.5 ppm). Peaks are generally assigned using published chemical shifts and experimental assignments via COSY and TOCSY experiments.

Percent composition is calculated using the anomeric cross peak volumes, for which all uronic acid residues have similar 1JCH couplings as do all glucosamine residues. For glucosamine anomeric peaks where overlapping prevents precise quantification, H2/C2 signals are integrated instead. The amount of every monosaccharide is expressed as percentage of the total glucosamine or uronic acid content. The ratio of 6-O-sulfation versus 6-O-desulfation is calculated from H6/C6 signal integration.

The percent composition data is provided in Table 11A.

Additional information useful for the methods found herein can be found in, e.g. Guerrini et al. (2005) Anal. Biochem., 337: 35-47.

Pharmaceutical Compositions

Compositions, e.g., pharmaceutically acceptable compositions, which include a LMWH preparation described herein, formulated together with a pharmaceutically acceptable carrier, are provided.

As used herein, "pharmaceutically acceptable carrier" includes any and all solvents, dispersion media, isotonic and absorption delaying agents, and the like that are physiologically compatible. The carrier can be suitable for intravenous, intramuscular, subcutaneous, parenteral, rectal, spinal or epidermal administration (e.g., by injection or infusion).

The compositions of this invention may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Typical preferred compositions are in the form of injectable or infusible solutions. The preferred mode of administration is parenteral (e.g., intravenous, subcutaneous, intraperitoneal, intramuscular). In a preferred embodiment, the LMWH preparation is administered by intravenous infusion or injection. In another preferred embodiment, the LMWH preparation is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intravitreous, intracardiac, intradermal, intraperitoneal, transtracheal, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high concentration. Sterile injectable solutions can be prepared by incorporating the active compound (i.e., LMWH in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, various polymers, monostearate salts and gelatin.

The LMWH preparations can be administered by a variety of methods known in the art, although for many therapeutic applications, the preferred route/mode of administration is intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Formulations for injection may be presented in unit dosage form, e.g., in ampoules or in multi-dose containers, e.g., with an added preservative. The compositions may take such forms as suspensions, solutions or emulsions in oily or aqueous vehicles, and may contain formulatory agents such as suspending, stabilizing and/or dispersing agents.

In certain embodiments, a LMWH preparation provided herein can be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the LMWH preparation may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. In addition, dry powder formations for inhalation therapy are within the scope of the invention. Such dry powder formulations may be prepared as disclosed in WO 02/32406.

The composition may also be formulated in rectal or vaginal compositions such as suppositories or retention enemas, e.g., containing conventional suppository bases such as cocoa butter or other glycerides.

In addition to the compositions described previously, the compounds may also be formulated as a depot preparation. Such long-acting formulations may be formulated with suitable polymeric or hydrophobic materials (for example, as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Examples of compositions which can be used for non-parental delivery (e.g., non-invasive delivery) include: metered amounts of a composition to be administered from an inhaler for pulmonary delivery; tablets having a prescribed dosage unit for oral administration; transdermal patches to deliver a dosage unit across the skin; and suppositories to deliver a desired dosage unit rectally or vaginally. The compositions can be included in a container, pack, or dispenser together with instructions for administration.

The LMWH preparation can also be administered with short or long term implantation devices. The preparation can be implanted subcutaneously, can be implanted into tissues or organs (e.g., the coronary artery, carotid artery, renal artery and other peripheral arteries, veins, kidney, heart cornea, vitreous, cerebrum, etc.), or can be implanted in physiological spaces around tissues and organs (e.g., kidney capsule, pericardium, thoracic or peritoneal space).

The LMWH preparation can also be used to coat various medical devices. For example, the LMWH preparation can be used to coat a stent or extracorporeal circuit. Such formulations of the LMWH preparations may include using, e.g., controlled release beads, gel or microspheres as well as various polymers such as PLGA, cellulose, alginate or other polysaccharides.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions.

The pharmaceutical compositions of the invention may include a "therapeutically effective amount" or a "prophylactically effective amount" of a LMWH preparation. A "therapeutically effective amount" refers to an amount effective, at dosages and for periods of time necessary, to achieve a desired therapeutic result. A therapeutically effective amount of the LMWH preparation may vary according to factors such as the disease state, age, sex, and weight of the individual, and the LMWH preparation to elicit a desired response in the individual. A therapeutically effective amount is also one in which any toxic or detrimental effects of the LMWH preparation is outweighed by the therapeutically beneficial effects. A "therapeutically effective dosage" preferably inhibits a measurable parameter, e.g., coagulation or thrombosis, e.g., as measured by ACT and aPTT, by at least about 20%, more preferably by at least about 40%, even more preferably by at least about 60%, and still more preferably by at least about 80% relative to untreated subjects. The ability of a compound to inhibit a measurable parameter, e.g., coagulation or thrombosis, can be evaluated in an animal model system predictive of efficacy in humans. Alternatively, this property of a composition can be evaluated by examining the ability of the compound in an in vitro assay. Exemplary doses for intravenous administration of the LMWH preparation are about IU/kg to 200 IU/kg, e.g., 1 IU/kg; 2 IU/kg; 3 IU/kg, 4 IU/kg, 5 IU/kg, 6 IU/kg, 7 IU/kg, 8 IU/kg, 9 IU/kg, 10 IU/kg, 11 IU/kg, 12 IU/kg, 13 IU/kg, 14 IU/kg, 15 IU/kg, 16 IU/kg, 17 IU/kg, 18 IU/kg, 19 IU/kg, 20 IU/kg, 21 IU/kg, 22 IU/kg, 25 IU/mg, 30 IU/kg, 40 IU/kg, 50 IU/kg, 70 IU/kg, 100 IU/kg, 125 IU/kg, 150 IU/kg, 175 IU/kg, 200 IU/kg. Other exemplary doses for intravenous administration of the LMWH preparation are about 0.03 mg/kg to 0.45 mg/kg, e.g., 0.03 mg/kg, 0.05 mg/kg, 0.1 mg/kg, 0.15 mg/kg, 0.2 mg/kg, 0.22 mg/kg, 0.25 mg/kg, 0.27 mg/kg, 0.3 mg/kg, 0.35 mg/kg, 0.37 mg/kg, 0.4 mg/kg, 0.44 mg/kg, preferably about 0.1 mg/kg, 0.15 mg/kg, 0.2 mg/kg, 0.25 mg/kg, 0.3 mg/kg, 0.35 mg/kg, 0.4 mg/kg, 0.44 mg/kg, 0.47 mg/kg, 0.5 mg/kg, 0.55 mg/kg, 0.60 mg/kg, 0.7 mg/kg, preferably about 0.30 to 0.50 mg/kg, e.g., 0.30 mg/kg, 0.35 mg/kg, 0.40 mg/kg, 0.42 mg/kg, 0.44 mg/kg, 0.47 mg/kg or 0.50 mg/kg.

A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Also within the scope of the invention are kits comprising a LMWH preparation provided herein. The kit can include one or more other elements including: instructions for use; other reagents, e.g., a therapeutic agent or protamine sulfate; devices or other materials for preparing the LMWH preparation for administration; pharmaceutically acceptable carriers; and devices or other materials for administration to a subject. Instructions for use can include instructions for monitoring anti-Xa activity and/or anti-IIa activity using coagulation assays such as ACT and aPTT. The instructions can include instructions for therapeutic application including suggested dosages and/or modes of administration, e.g., in a patient having a disorder, e.g., a disorder described herein. Other instructions can include instructions on reversing anti-Xa activity and/or anti-IIa activity using protamine sulfate. The kit can further contain at least one additional reagent, such as a diagnostic or therapeutic agent, e.g., a diagnostic or therapeutic agent as described herein, formulated as appropriate, in one or more separate pharmaceutical preparations.

Prophylactic and Therapeutic Uses

The LMWH preparations can be used to treat a subject. As used herein, the term "treat" or "treatment" is defined as the application or administration of a LMWH preparation to a subject, e.g., a patient, or application or administration to an isolated tissue or cell from a subject, e.g., a patient, which is returned to the patient. The subject can be a patient having a disorder (e.g., a disorder as described herein), a symptom of a disorder or a predisposition toward a disorder. The treatment can be to cure, heal, alleviate, relieve, alter, remedy, ameliorate, palliate, improve or affect the disorder, the symptoms of the disorder or the predisposition toward the disorder. As used herein, a subject is a vertebrate such as a human, non-human primate, cow, horse, pig, sheep, goat, dog, cat, or rodent. The subject can be, e.g., an experimental animal, a veterinary animal, or a human subject. A treatment can be therapeutic, e.g., a treatment which cures, heals, alleviates, relieves, alters, remedies, ameliorates, palliates, improves or affects the disorder or a symptom of the disorder, e.g., lessens, mitigates or ameliorates an existing unwanted condition or symptom thereof, or prophylactic, e.g., a treatment which delays, e.g., prevents, the onset of an unwanted condition or symptom thereof.

Heparins and LMWHs have many therapeutic utilities. The LMWH preparations provided herein can be used for the treatment of any type of condition in which heparin or LMWH therapy is useful. Thus, the preparations and methods are useful in a variety of in vitro, in vivo and ex vivo methods. For instance, it is known that heparins and LMWHs are useful for preventing and treating dementia, such as Alzheimer's disease, disorders associated with coagulation (e.g., DVT and PE), fibrotic disorders (e.g., major organ fibrosis, fibroproliferative disorders and scarring associated with trauma), thrombotic disorders (e.g., ACS, stable or unstable angina, MI (e.g., STEMI and NSTEMI)) or cardiovascular disease (atherosclerosis), vascular conditions or arterial fibrillation, allergy or respiratory disorders (e.g., asthma, emphysema, adult respiratory distress syndrome (ARDS), cystic fibrosis, and lung reperfusion injury), circulatory shock and related disorders, angiogenic disorders, cancer and metastatic disorders, sepsis, stenosis and restenosis, and osteoporosis. The LMWH preparations provided herein can also be used on subjects having a fracture (e.g., a hip fracture) or to a subject prior to, during or after a surgical intervention (e.g., organ transplant, orthopedic surgery, hip replacement, knee replacement, PCI, stent placement, angioplasty and CABG). Each of these disorders is well-known in the art and is described, for instance, in Harrison's Principles of Internal Medicine (McGraw Hill, Inc., New York), which is incorporated by reference. The use of HLGAG compositions in various therapeutic methods is described and summarized in Huang, J. and Shimamura, A., Coagulation Disorders, 12, 1251-1281 (1998).

Thus, the LMWH preparations are useful for treating or preventing disorders associated with coagulation. When an imbalance in the coagulation pathway shifts towards excessive coagulation, the result is the development of thrombotic tendencies, which are often manifested as heart attacks, strokes, DVT, ACS, stable and unstable angina, and myocardial infarcts. A "disease associated with coagulation" as used herein refers to a condition characterized by local inflammation which can result from an interruption or reduction in the blood supply to a tissue which may occur, for instance, as a result of blockage of a blood vessel responsible for supplying blood to the tissue such as is seen for myocardial or cerebral infarction or peripheral vascular disease, or as a result of emboli formation associated with conditions such as arterial fibrillation, DVT or PE. Persons undergoing surgery, anesthesia and extended periods of bed rest or other inactivity are often susceptible to a condition known as deep venous thrombosis, or DVT, which is a clotting of venous blood in the lower extremities and/or pelvis. This clotting occurs due to the absence of muscular activity in the lower extremities required to pump the venous blood (stasis), local vascular injury or a hypercoaguble state. The condition can be life-threatening if a blood clot migrates to the lung, resulting in a "pulmonary embolus" or otherwise interferes with cardiovascular circulation. One method of treatment involves administration of an anti-coagulant.

The methods are useful for treating thrombotic disorders and cardiovascular disease. Cardiovascular disease includes, but are not limited to, atherosclerosis and arterial fibrillation. Atrial fibrillation is a common form of arrhythmia generally arising as a result of emotional stress or following surgery, exercise, or acute alcoholic intoxication. Arterial fibrillation is characterized by disorganized arterial activity without discrete P waves on the surface ECG. This disorganized activity can lead to improper blood flow in the atrium and thrombus formation. These thrombi can embolize, resulting in cerebral ischemia and other disorders.

Thrombotic disorders include, but are not limited to, ACS, e.g., MI, stable and unstable angina. Myocardial infarction is a disease state which sometimes occurs with an abrupt decrease in coronary blood flow that follows a thrombotic occlusion of a coronary artery previously narrowed by atherosclerosis. Such injury may be produced or facilitated by factors such as cigarette smoking, hypertension, and lipid accumulation. Angina is due to transient myocardial ischemia. This disorder is usually associated with a heaviness, pressure, squeezing, smothering, or choking feeling below the sternum. Episodes are usually caused by exertion or emotion, but can occur at rest. STEMI, also referred to as "Q wave myocardial infarction", refers to MI with an abnormal echocardiogram. NSTEMI, or "non-Q wave myocardial infarction", is not associated an echocardiogram abnormality. Stable angina occurs at predictable times with a specific amount of exertion or activity. Unstable angina may occur as a change in the usual pattern of stable angina. It my include chest pain that occurs at rest or with less and less exertion, that may be more severe and last longer, or that is less responsive to nitroglycerin. Unstable angina means that blood flow has gotten worse potentially by an increased narrowing or small blood clots that form in the coronary arteries. Unstable angina is a warning sign that myocardial infarction may soon occur.

The LMWH preparation can be used for the treatment of thrombotic and cardiovascular disorders alone or in combination with other therapeutic agents for reducing the risk of a cardiovascular disease or for treating the cardiovascular disease. For example, the combination therapy can include a LMWH preparation coformulated with, and/or coadministered with, one or more additional therapeutic agents, e.g., one or more therapeutic agent described herein. Administered "in combination", as used herein, means that two (or more) different treatments are delivered to the subject during the course of the subject's affliction with the disorder, e.g., the two or more treatments are delivered after the subject has been diagnosed with the disorder or identified as at risk for the disorder and before the disorder has been prevented, cured or eliminated. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. The delivery can be such that an effect of the first treatment delivered is still detectable when the second is delivered. Other therapeutic agents include, but are not limited to, anti-inflammatory agents, anti-thrombotic agents, anti-platelet agents, fibrinolytic agents, thrombolytics, lipid reducing agents, direct thrombin inhibitors, anti-Xa inhibitors, anti-IIa inhibitors, glycoprotein IIb/IIIa receptor inhibitors and direct thrombin inhibitors. Examples of agents that can be administered in combination with the LMWH preparations provided herein include bivalirudin, hirudin, hirugen, Angiomax, agatroban, PPACK, thrombin aptamers, aspirin, GPIIb/IIIa inhibitors (e.g., Integrelin), P2Y12 inhibitors, thienopyridine, ticlopidine, and clopidogrel.

The monitorability by standard anticoagulation assays such as ACT and aPTT as well as the reversibility of the LMWH preparations provided herein provided improved flexibility in treating patients such as those patients admitted to the hospital and undergoing evaluation for possible cardiovascular surgery. Such benefits are highlighted by the following scenario. A patient goes the hospital complaining of symptoms that can be associated with various thrombotic disorders such as ACS including stable angina, unstable angina and MI. The monitorability and reversibility of the LMWH preparations provided herein allow use of such preparations while the patient is being evaluated for potential cardiovascular surgery. If it is determined that the patient will receive surgical intervention such as PCI or stent placement, the monitorability of the LMWH preparations, the anti-Xa activity and anti-IIa activity of the LMWH preparation can be monitored during the procedure, and, if necessary, one or more additional doses of the LMWH preparation can be given during or after the procedure to maintain these activities. If it is determined that a patient will receive a surgical intervention such as CABG, the anti-Xa activity and anti-IIa activity of the LMWH preparation can be neutralized with protamine sulfate prior to surgical intervention. In addition, anti-Xa activity and anti-IIa activity can be monitored in the patient to ensure the activity is sufficiently decreased prior to the surgery.

The LMWH preparations provided herein are also useful for treating vascular conditions. Vascular conditions include, but are not limited to, disorders such as DVT, peripheral vascular disease, cerebral ischemia, including stroke, and PE. A cerebral ischemic attack or cerebral ischemia is a form of ischemic condition in which the blood supply to the brain is blocked. This interruption or reduction in the blood supply to the brain may result from a variety of causes, including an intrinsic blockage or occlusion of the blood vessel itself, a remotely originated source of occlusion, decreased perfusion pressure or increased blood viscosity resulting in inadequate cerebral blood flow, or a ruptured blood vessel in the subarachnoid space or intracerebral tissue. The methods are useful for treating cerebral ischemia. Cerebral ischemia may result in either transient or permanent deficits and the seriousness of the neurological damage in a patient who has experienced cerebral ischemia depends on the intensity and duration of the ischemic event. A transient ischemic attack is one in which the blood flow to the brain is interrupted only briefly and causes temporary neurological deficits, which often are clear in less than 24 hours. Symptoms of TIA include numbness or weakness of face or limbs, loss of the ability to speak clearly and/or to understand the speech of others, a loss of vision or dimness of vision, and a feeling of dizziness. Permanent cerebral ischemic attacks, also called stroke, are caused by a longer interruption or reduction in blood flow to the brain resulting from either a thrombus or embolism. A stroke causes a loss of neurons typically resulting in a neurologic deficit that may improve but that does not entirely resolve.

Thromboembolic stroke is due to the occlusion of an extracranial or intracranial blood vessel by a thrombus or embolus. Because it is often difficult to discern whether a stroke is caused by a thrombosis or an embolism, the term "thromboembolism" is used to cover strokes caused by either of these mechanisms.

The methods are also directed to the treatment of acute thromboembolic stroke using a LMWH preparation provided herein. An acute stroke is a medical syndrome involving neurological injury resulting from an ischemic event, which is an interruption or reduction in the blood supply to the brain.

An effective amount of a LMWH preparation alone or in combination with another therapeutic for the treatment of stroke is that amount sufficient to reduce in vivo brain injury resulting from the stroke. A reduction of brain injury is any prevention of injury to the brain which otherwise would have occurred in a subject experiencing a thromboembolic stroke absent the treatment described herein. Several physiological parameters may be used to assess reduction of brain injury, including smaller infarct size, improved regional cerebral blood flow, and decreased intracranial pressure, for example, as compared to pretreatment patient parameters, untreated stroke patients or stroke patients treated with thrombolytic agents alone.

The LMWH preparation may be used alone or in combination with a therapeutic agent for treating a disease associated with coagulation. Examples of therapeutics useful in the treatment of diseases associated with coagulation include anticoagulation agents, antiplatelet agents, and thrombolytic agents.

Anticoagulation agents prevent the coagulation of blood components and thus prevent clot formation. Anticoagulants include, but are not limited to, warfarin, Coumadin, dicumarol, phenprocoumon, acenocoumarol, ethyl biscoumacetate, and indandione derivatives. "Direct thrombin inhibitors" include hirudin, hirugen, Angiomax, agatroban, PPACK, thrombin aptamers. Antiplatelet agents inhibit platelet aggregation and are often used to prevent thromboembolic stroke in patients who have experienced a transient ischemic attack or stroke. Thrombolytic agents lyse clots which cause the thromboembolic stroke. Thrombolytic agents have been used in the treatment of acute venous thromboembolism and pulmonary emboli and are well known in the art (e.g. see Hennekens et al, J Am Coll Cardiol; v. 25 (7 supp), p. 18S-22S (1995); Holmes, et al, J Am Coll Cardiol; v.25 (7 suppl), p. 10S-17S(1995)).

Pulmonary embolism as used herein refers to a disorder associated with the entrapment of a blood clot in the lumen of a pulmonary artery, causing severe respiratory dysfunction. Pulmonary emboli often originate in the veins of the lower extremities where clots form in the deep leg veins and then travel to lungs via the venous circulation. Thus, pulmonary embolism often arises as a complication of deep venous thrombosis in the lower extremity veins. Symptoms of pulmonary embolism include acute onset of shortness of breath, chest pain (worse with breathing), and rapid heart rate and respiratory rate. Some individuals may experience haemoptysis.

The preparations and methods are also useful for treating or preventing atherosclerosis. Heparin has been shown to be beneficial in prevention of atherosclerosis in various experimental models. Atherosclerosis is one form of arteriosclerosis that is believed to be the cause of most coronary artery disease, aortic aneurysm and atrial disease of the lower extremities, as well as contributing to cerebrovascular disease.

The LMWH preparations are also useful before, during or after surgical and dialysis procedures. Surgical patients, especially those over the age of 40 years have an increased risk of developing DVT. Thus, the use of the LMWH preparations provided herein for preventing the development of thrombosis associated with surgical procedures is contemplated. In addition to general surgical procedures such as percutaneous intervention (e.g., percutaneous coronary intervention (PCI)), PCTA, stents and other similar approaches, hip or knee replacement, cardiac-pulmonary by-pass surgery, coronary revascularization surgery, orthopedic surgery, and prosthesis replacement surgery, the methods are also useful in subjects undergoing a tissue or organ transplantation procedure or treatment for fractures such as hip fractures.

In addition, the LMWH preparations provided herein are useful for treatment of respiratory diseases such as cystic fibrosis, asthma, allergy, emphysema, adult respiratory distress syndrome (ARDS), lung reperfusion injury, and ischemia-reperfusion injury of the lung.

Cystic fibrosis is a chronic progressive disease affecting the respiratory system. One serious consequence of cystic fibrosis is *Pseudomonas aeruginosa* lung infection, which by itself accounts for almost 90% of the morbidity and mortality in cystic fibrosis. Therapeutics for treating cystic fibrosis include antimicrobials for treating the pathogenic infection.

Asthma is a disorder of the respiratory system characterized by inflammation, narrowing of the airways and increased reactivity of the airways to inhaled agents. Asthma is frequently, although not exclusively, associated with atopic or allergic symptoms. Asthma may also include exercise induced asthma, bronchoconstrictive response to bronchostimulants, delayed-type hypersensitivity, auto immune encephalomyelitis and related disorders. Allergies are generally caused by IgE antibody generation against allergens. Emphysema is a distention of the air spaces distal to the terminal bronchiole with destruction of alveolar septa. Emphysema arises out of elastase induced lung injury. Adult respiratory distress syndrome is a term which encompasses many acute defuse infiltrative lung lesions of diverse ideologies which are accompanied by severe atrial hypoxemia. One of the most frequent causes of ARDS is sepsis.

Inflammatory diseases include but are not limited to autoimmune diseases and atopic disorders. Other types of inflammatory diseases which are treatable with the LMWH preparations provided herein are refractory ulcerative colitis, Crohn's disease, multiple sclerosis, autoimmune disease, non-specific ulcerative colitis, sepsis and interstitial cystitis.

The LMWH preparations can be used to treat fibrotic disorders such as major organ fibrosis, fibroproliferative disorders and scarring associated with trauma. Major organ fibrosis includes, but is not limited to, interstitial lung disease (ILD), liver cirrhosis, kidney disease (e.g., diabetes and untreated hypertensive disease), heart disease and disorders of the eye (e.g., macular degeneration, retinal or vitreous retinopathy). Examples of Fibroproliferative disorders include systemic and local scleroderma, keliods and hypertrophic scars, atherosclerosis, restenosis, fibrosarcoma and rheumatoid arthritis. Examples of scarring associated with trauma include scarring due to surgery, chemotherapeutic-induced fibrosis, radiation-induced fibrosis, scarring associated with injury or burns.

In one embodiment, the LMWH preparations are used for inhibiting angiogenesis. Angiogenesis as used herein is the inappropriate formation of new blood vessels. "Angiogenesis" often occurs in tumors when endothelial cells secrete a group of growth factors that are mitogenic for endothelium causing the elongation and proliferation of endothelial cells which results in the generation of new blood vessels. Several of the angiogenic mitogens are heparin binding peptides which are related to endothelial cell growth factors. The inhibition of angiogenesis can cause tumor regression in animal models, suggesting a use as a therapeutic anticancer agent. Angiogenic disorders include, but are not limited to, neovascular disorders of the eye, osteoporosis, psoriasis, arthritis, cancer and cardiovascular disorders.

The LMWH preparations, may also be used inhibit cancer cell growth and metastasis. Thus the methods are useful for treating and/or preventing tumor cell proliferation or metastasis in a subject. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; leukemias, lymphomas; liver cancer; lung cancer (e.g. small cell and non small cell); melanoma; neuroblastomas; oral cancer; ovarian cancer; pancreatic cancer; prostate cancer; rectal cancer; sarcomas; skin cancer; testicular cancer; thyroid cancer; and renal cancer, as well as other carcinomas and sarcomas.

A subject in need of cancer treatment may be a subject who has a high probability of developing cancer. These subjects include, for instance, subjects having a genetic abnormality, the presence of which has been demonstrated to have a correlative relation to a higher likelihood of developing a cancer and subjects exposed to cancer-causing agents such as tobacco, asbestos, or other chemical toxins, or a subject who has previously been treated for cancer and is in apparent remission.

When administered to a patient undergoing cancer treatment, the LMWH preparation may be administered in cocktails containing other anti-cancer agents. The LMWH preparation may also be administered in cocktails containing agents that treat the side-effects of radiation therapy, such as anti-emetics, radiation protectants, etc.

The treatments provided herein can further include administering protamine sulfate to neutralize the anti-Xa activity and/or anti-IIa activity of the LMWH preparation, e.g., once anti-coagulation or anti-thrombotic activity is no longer necessary. Protamine sulfate can be administered, e.g., by intravenous administration, at a dose of about 1, 2, 3 mg of protamine sulfate per 100 IU of anti-Xa activity. The IUs of anti-Xa activity can be determined using, e.g., the coagulation assays described herein.

Other Embodiments

This invention is further illustrated by the following examples that should not be construed as limiting. The contents of all references, patents and published patent applications cited throughout this application are incorporated herein by reference.

EXAMPLES

Methods of Manufacturing M118-REH

Manufacturing Process

The depiction of the process used to produce M118-REH is shown in FIG. 1. Briefly, in Step 1 of the process, commercially available Unfractionated Heparin, USP (UFH) was subjected to a step-wise series of aqueous ethanol precipitations with calcium acetate in a 3:1 mass to mass ratio of calcium acetate to UFH to extract the portion of the UFH that is of lower molecular weight (also referred as the portion that is substantially the fast moving fraction). The resulting product of Step 1 fractionation was designated Intermediate 1.

Step 2 involved the digestion of Intermediate 1 using a modified heparinase III enzyme having a substitution of an alanine for histidine at amino acid residue 225 (MO11) in aqueous sodium acetate buffer, pH 7.2 at 37° C. to produce Intermediate 2. MO11 cleaved by β-elimination between N-acetylglucosamine residues and under sulfated uronic acids producing chains having a Δ4,5 uronic acid group at the non-reducing end and an N-acetyl glucosamine at the reducing end. When digestion was complete, heat was turned off and sodium chloride was added to achieve a final solution concentration of approximately 2% w/v.

In Step 3, size exclusion chromatography (SEC) was used to separate the high anti-factor Xa and IIa components of Intermediate 2 away from the lower activity materials. The product of this step was designated Intermediate 3.

In Step 4, individual or combined Intermediate 3 materials were dissolved in purified water, filtered through a 0.2 pm filter, and lyophilized to produce M118-REH drug substance. Starting Material in the Manufacture of M118-REH Specifications of Starting Materials The starting material for making M118-REH, UFH sodium (USP) is of porcine intestinal mucosa origin. In addition to the USP tests, additional controls have been put in place. These controls are listed in Table 1:

TABLE 1

UFH Assays and Specifications in Addition to DMF

| Test | Specification |
|---|---|
| Certificate of Analysis Potency | NLT 160 U/mg on a dried basis |
| Agarose Gel Electrophoresis | Report Fast-Moving and Slow-Moving heparin Report Dermatan sulfate and Chondroitin sulfate |

The Agarose Gel Electrophoresis (AGE) semi-quantitatively separates the various components of heparin-based materials, as dermatan sulfate and chondroitan sulfate on the basis of their electrophoretic mobility. A horizontal separation in 0.5% agarose gel was conducted in barium acetate buffer pH 5.8, followed by 1,3-diaminopropane acetate pH 9 buffer. A special electrophoresis tank was employed, whereby the electrode chambers containing liquid buffer were overlaid with a water-immiscible, low density organic solvent (e.g., petroleum ether or heptane). This design provided efficient heat transfer between the agarose gel plate and a metal cooling tray filled with ice.

Low molecular weight heparins traditionally are prepared from USP grade UFH. To achieve a higher potency low molecular weight heparin drug substance, the UFH starting material for the M118-REH process was restricted to those with potencies in excess of 160 IU/mg. To control the levels of dermatan sulfate and chondroitin sulfate, these were measured in the UFH starting material and controlled in Step 1 of the M118-REH manufacturing process.

Structural Analysis of Intermediates

The steps in the M118-REH manufacturing process are outlined above and shown in FIG. 1. Characterization technology for studying sugar structure provides an understanding of the structural attributes that change when UFH is subjected to this process at each step. This information allows control and reproducibility from the process, including selection of starting material.

Analysis of different Step 2 materials (or Intermediate 1 samples) and the starting UFH samples used to prepare them was carried out using 2D-NMR (HSQC) analysis, and capillary electrophoresis.

The building blocks that constitute the starting material as well as the intermediate were identified and quantified. Some of the Step 2 materials studied were not ideal substrates for the next step (enzymatic digestion) and attributes were identified that indicate preferred step 2 material.

Shown in Table 2 and Table 3 below are data from 2D NMR analysis that illustrate the differences between the starting UFH and step 2 material. This analysis allows determination of the overall differences in structural attributes when going through Step 1 of the M118-REH manufacturing process. Based on all the data obtained from the different analyses certain conclusions about the starting material, intermediates and manufacturing process were made.

TABLE 2

2D NMR analysis of UFH and the step 2 materials obtained from them. These materials represent the preferred step 2 material.

| Monosaccharide | UFH #1 | Step 2 #1 | Step 2 #2 | UFH #2 | Step 2 #3 |
|---|---|---|---|---|---|
| Glucosamine | | | | | |
| $H_{NS}$-($I_{2S}$) | 63.7 | 57 | 57.1 | 65.6 | 56.3 |
| $H_{NS}$-(I) | 9 | 11.1 | 12.3 | 7.4 | 12.3 |
| $H_{NS}$-(G) | 7.7 | 12.7 | 11.2 | 8.9 | 11.8 |
| $H_{NAc\ (internal)}$ | 12.1 | 13.9 | 14.6 | 11.1 | 13.3 |
| $H_{NS,3S}$ | 6.1 | 4.4 | 4.8 | 7 | 5.5 |
| $H_{6S}$ | 78.2 | 85.3 | 85.8 | 82.5 | 86.7 |
| Linkage Region (L.R.) | 4.2 | 3.6 | 3.8 | 2.1 | 1.8 |
| ΔU | 0 | 0 | 0 | 0 | 0 |
| $I_{2S}$ | 73 | 66.8 | 70.9 | 75.9 | 70.2 |
| I-($H_{NS/Ac,6S}$) | 8.1 | 11.8 | 9.4 | 7.2 | 8.5 |
| I-($H_{NS/Ac}$) | 1.4 | 2 | 1.4 | 0.8 | 1.1 |
| G-($H_{NS}$) | 8.1 | 11.2 | 8.4 | 8 | 9.6 |
| G-($H_{NS,3S}$) | 2.8 | 2.8 | 3.2 | 2.7 | 3.7 |
| G-($H_{NAc}$) | 6.5 | 5.3 | 6.6 | 5.3 | 4.6 |
| Epoxide | 0 | 0 | 0 | 0 | 0.6 |

The step 2 materials had lower relative $I_{2S}$ content when compared to starting material and this was also reflected by the decrease in $H_{NS}$-($I_{2S}$) structure as shown in the table. This was accompanied by a concomitant increase in the $H_{NS}$-(I) and $H_{NS}$-(G) structures as expected. Interestingly, there was also a relative increase in the amount of 6-O-sulfated hexosamine ($H_{6S}$).

TABLE 3

2D NMR analysis of UFH and the step 2 materials obtained from them. These materials represent the less preferred step 2 material.

| Monosaccharide | UFH #1 | Step 2 #1 | UFH #2 | Step 2 #2 |
|---|---|---|---|---|
| Glucosamine | | | | |
| $H_{NS}$-($I_{2S}$) | 68.1 | 63 | 66.6 | 61.8 |
| $H_{NS}$-(I) | 6.3 | 10.7 | 8.6 | 11.9 |
| $H_{NS}$-(G) | 8.5 | 12.7 | 9.5 | 11.1 |
| $H_{NAc\ (internal)}$ | 11.2 | 8.3 | 9.8 | 8.1 |
| $H_{NS,3S}$ | 5.9 | 5.3 | 5.4 | 6.8 |
| $H_{6S}$ | 82.2 | 89.2 | 84.7 | 88.4 |
| Linkage Region (L.R.) | 2.1 | 1.5 | 1.8 | 1.1 |
| ΔU | 0 | 0 | 0 | 0 |
| $I_{2S}$ | 76.8 | 71.3 | 76.1 | 69.8 |
| I-($H_{NS/Ac,6S}$) | 6.7 | 6.3 | 6.2 | 7.1 |
| I-($H_{NS/Ac}$) | 0.6 | 0.8 | 2 | 1.6 |
| G-($H_{NS}$) | 7.2 | 10 | 6.6 | 10.3 |
| G-($H_{NS,3S}$) | 1.6 | 2.3 | 3.7 | 3 |
| G-($H_{NAc}$) | 4.3 | 2.4 | 3.6 | 2.1 |
| Epoxide | 2.8 | 3.6 | 1.8 | 2.4 |

"Preferred" step 2 materials are those that are good substrates for the next step in the process i.e. enzymatic digestion by MO11, whereas "less preferred" step 2 materials are poorer substrates. When comparing the relative amounts of the $H_{NAc}$ (internal) it was observed that in "preferred" step 2 materials the $H_{NAc}$ content actually goes up after step 1 whereas in "less preferred" step 2 materials it is reduced (see Table 2 and 3). Another observation was that the relative amount of the G-$H_{NAc}$ unit was reduced to a much larger extent in "less preferred" step 2 as compared to "preferred" step 2 material. These observations were justified in the context of substrate specificity of MO11 which prefers to act on the linkage adjacent to non-sulfated glucuronic acid (i.e. $H_{NAc}$-G).

Through the analysis, structural attributes that change during the first step (precipitation) of the manufacturing process going from UFH to step 2 material were identified. Since the N-acetyl content in the step 2 material appears to be important for the subsequent enzymatic digestion step, it is desirable to use a starting UFH with a higher N-acetyl content which may allow better production of step 2 material after precipitation. Therefore, based on this analysis, a preselected criterion for starting UFH has been identified that allows better control and evaluation of the M118-REH manufacturing process.

Other assays and specifications for process intermediates are shown in Table 4, and described in detail below.

TABLE 4

Assays and Specifications for Intermediates

| Intermediate | Assay | Specifications |
|---|---|---|
| 1 | Agarose Gel Electrophoresis: Dermatan and Chondroitin Sulfate below detection limit | Dermatan and Chondroitin Sulfate below detection limit |
| 2 | Automated Chromogenic Assay | |
| 2 | SEC-MALS | |
| 3 | Automated Chromogenic Assay | Anti-Factor Xa NLT 130 IU/mg |
| | Automated Chromogenic Assay SEC-MALS | Molar Mass: 5000-9000 Dalton Polydispersity (PD): NMT 1.5 |

The Agarose Gel Electrophoresis process has been described above.

The anti-factor Xa activity was measured as described herein. The anti-factor Xa activity was measured on either a Diagnostica Stago analyzer with the Stachrom® Heparin Test kit, or on an ACL Futura™ Coagulation system with the Coatest® Heparin Kit from Chromogenix. The Analyzer response was calibrated using the NIBSC International Standard for Low Molecular Weight Heparin, lot 01/608 or current lot. The potency of M118-REH Drug Substance was calculated in International Units of anti-factor Xa activity per milligram using the statistical methods for parallel line assays.

The anti-factor IIa activity was measured as described herein. using the following principle. The anti-factor IIa activity was measured on either a Diagnostica Stago analyzer or on an ACL Futura™ Coagulation system, with reagents from Chromogenix (S-2238 substrate, thrombin (53nkat/vial), and antithrombin). The Analyzer response was calibrated using the 2nd International Standard for Low Molecular Weight Heparin, lot 01/608 or equivalent. The potency of M118-REH Drug Substance was calculated in International Units of anti-factor IIa activity per milligram using the statistical methods for parallel line assays.

The weight average molar mass, the polydispersity and the molar mass distribution of M118-REH Intermediates were measured using a Size Exclusion Chromatography (SEC) system attached to a Wyatt miniDAWN Multi Angle Light Scattering (MALS) detector or any other suitable MALS detector, and an Optilab rEX interferometric refractometer (RID) or other suitable RID in accordance with the USP <621>, current version. The SEC columns set consisted in columns packed with a high resolution L20 packing, for example a Tosoh SWXL guard column coupled with a Tosoh TSKgel G3000SWXL and a Tosoh TSKgel G2000SWXL in series. The system was equilibrated at 0.5 mL/min with a 0.2M sodium sulfate mobile phase whose pH was adjusted to 5.0 with sulfuric acid. Sodium azide was added at 0.05% in the mobile phase. The M118-REH Intermediate was dissolved in the mobile phase to obtain a 10 mg/mL solution prior to injection. The weight average molar mass, the polydispersity and the distribution parameters were measured using the Wyatt Astra software or any appropriate software. The distribution was characterized by the percentage of chains with a molar mass lower than 5,500 Da ($M_{5500}$), and the percentage of chains with a molar mass higher than 8,000 Da ($M_{8000}$) or by the percentage of chains with a molar mass lower than 5,000 Da ($M_{5500}$), and the percentage of chains with a molar mass higher than 7,500 Da ($M_{8000}$).

In Step 2 of the M118-REH process, Intermediate 1 was digested with the MO11 enzyme. As the enzyme digested the Intermediate 1 substrate, it generated Intermediate 2 containing Δ4,5 uronic acid residues possessing a characteristic $UV_{232}$ absorbance. To monitor the progress of the digestion, the reaction solution was sampled periodically and the absorbance at 232 nm was measured. The Step 2 digestion was considered complete when the absorbance at 232 nm has not changed more than 2 AU in 1 hour.

Table 5 shows the weight average molecular weight and distribution of various preparations of M118-REH. Table 6 shows a comparison of M118-REH, LMW and UFH products.

TABLE 5

Molecular weight, polydispersity and chain length characteristics of 5 different lots of M118-REH

| LOT # | Mw (Da) | PD | M5500 | M8000 | n |
|---|---|---|---|---|---|
| 1 | 7250 | 1.1 | 24.6% | 31.9% | 13 |
| 2 | 7300 | 1.1 | 26.4% | 33.0% | 13 |
| 3 | 7500 | 1.1 | 24.6% | 35.0% | 13 |
| 4 | 6350 | 1.1 | 38.6% | 17.7% | 12 |
| 5 | 6450 | 1.1 | 40.6% | 20.7% | 12 |

* MW calculated with dn/dc measured on M118-REH material.

TABLE 6

Comparison of M118, LMWH and UFH Products

| Attribute | M118-REH[1] | Lovenox[2] | UFH[3] |
|---|---|---|---|
| Anti-Xa Activity (IU/mg) | 228 | 100 | 150 |
| Anti-IIa Activity (IU/mg) | 155 | 25 | 150 |
| Anti-Xa/Anti IIa Ratio | 1.5:1 | 4:1 | 1:1 |
| Average Molecular Weight | 6350 | 4,500 | 12,000 |
| Polydispersity | 1.1 | 1.3 | 1.6 |
| Subcutaneous bioavailability | Yes | Yes | No |
| Reversibility w/protamine | Full | Partial | Full |
| Monitorable with ACT/APTT | Yes | No | Yes |

[1],*Values for lot used in M118-REH Drug Product formulation; average MW processed with dn/dc estimated from literature data on UFH
[2]Lovenox package insert
[3]USP heparin monograph Structural Characterization of M118-REH: Identification of Structural Characteristics of M118-REH An approach towards the characterization of M118-REH has been developed that involves several different analytical techniques that provide complementary sets of data.

This provides characterization of M118-REH, and it allows for an understanding of what makes M118-REH unique when compared to other LMWHs. The summaries of findings from these characterization techniques that help define M118-REH as a unique mixture.

A characterization of unfractionated heparin (UFH) and LMWH products was completed using a series of analytical techniques that has led to the identification of chemical structures unique to a given LMWH, structures that are present in several different LMWHs but at varying amounts, and structures that are responsible for the biological properties of heparins.

Analysis of a complex LMWH mixture like M118-REH needs to account for not only the inherent structural variability that arises from the biosynthesis of heparin, but also for the structures that arise from the enzymatic cleavage and manufacturing processes. This can be addressed by resolving the natural as well as modified (if any) reducing and non-reducing end signatures present in the mixture. At the same time, it also needs to be confirmed that the relative "order" of the disaccharide units, as defined by the parent UFH molecule, is not affected by the manufacturing process. Therefore, it is necessary to provide a sequence context in which these modified or natural building blocks are present in the chains of M118-REH. To account for these factors, an approach towards the characterization of M118-REH has been developed that involves using data obtained from different analytical techniques that provide unique and complementary sets of data.

The composition analysis was performed with CE to identify and quantify individual building blocks that comprise the M118-REH chains. These methods also identify the building block structure that is responsible for anti-Xa activity, referred to as "Anti-Xa Building Block".

Building Block Analysis/Compositional Analysis

Compositional Analysis by Capillary Electrophoresis (CE)

Briefly, this method involves the enzymatic digestion of M118-REH into its constituent building blocks followed by separation using CE (FIGS. 2A and 2B).

CE is a high resolution separation technique and has been used extensively in the analysis of UFH and other glycosaminoglycans. The current method used capillary zone electrophoresis in an uncoated fused silica capillary. With capillary electrophoresis, the most highly sulfated species migrated through the capillary the fastest and are detected first.

Representative Data

Figure 2:
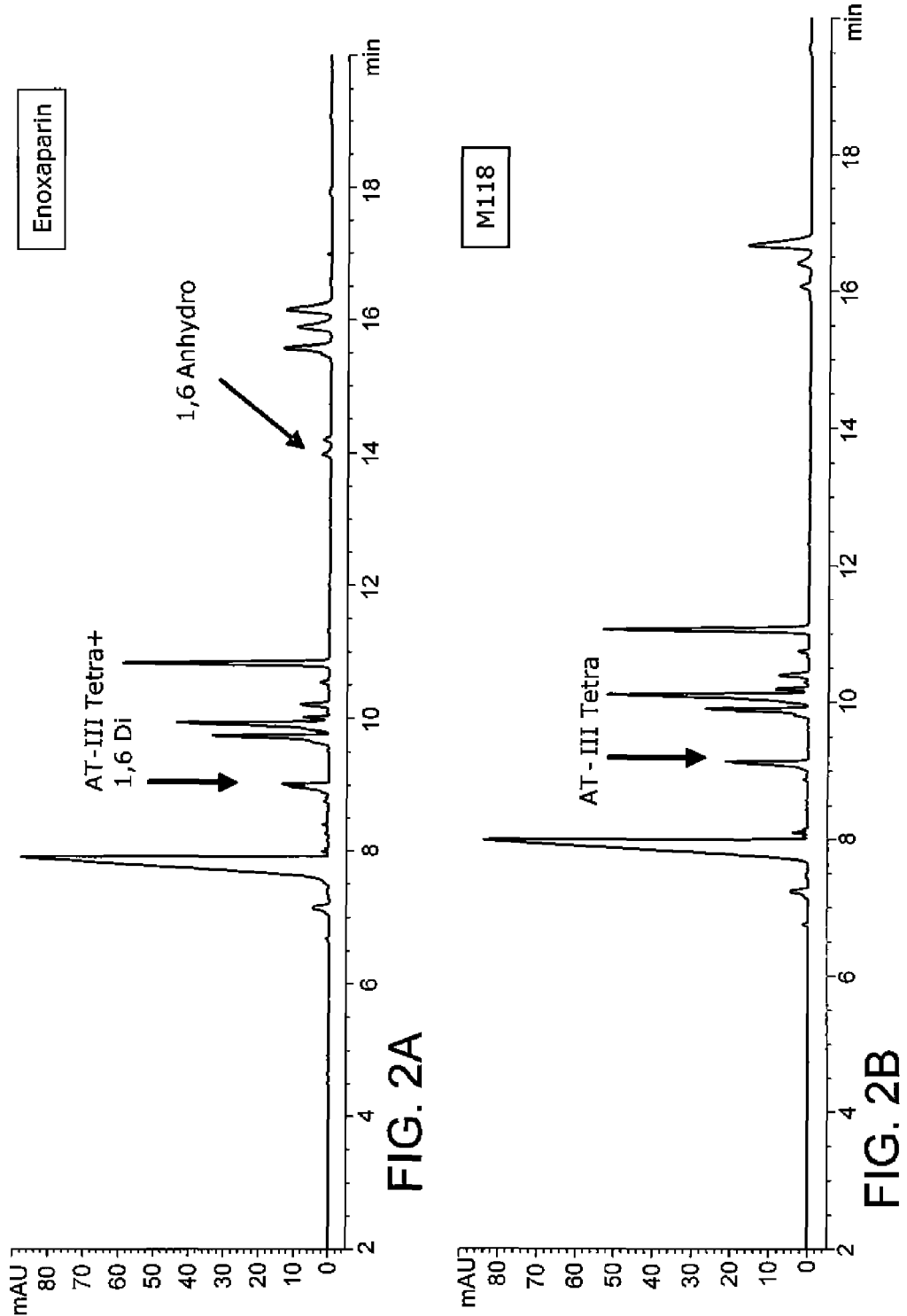
FIG. 2A is a graph depicting capillary electrophoresis profile of enoxaparin digested with heparinase I, heparinase II and heparinase III.
FIG. 2B is a graph depicting capillary electrophoresis profile of M118-REH digested with heparinase I, heparinase II and heparinase III.
Figure 3:
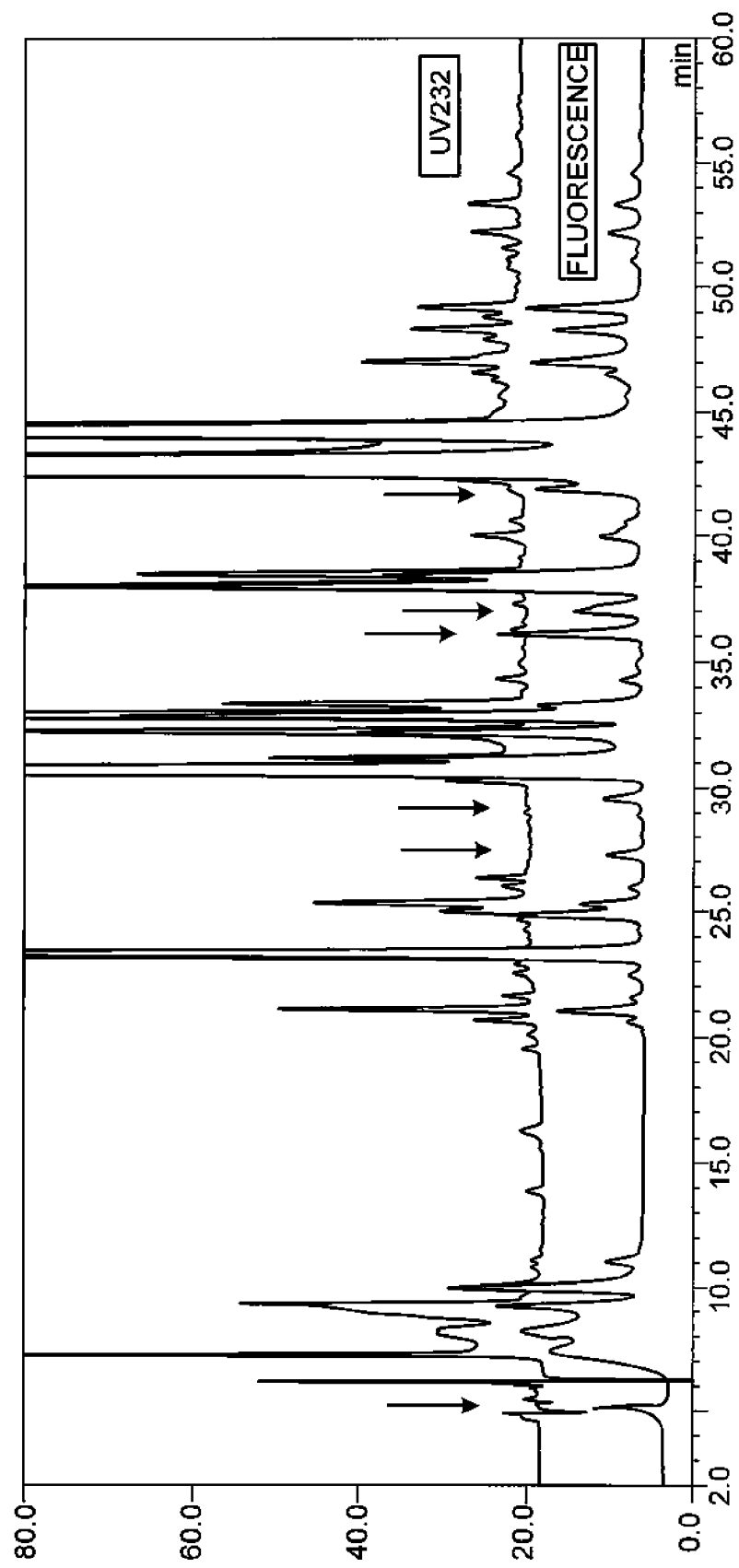
FIG. 3 is a graph depicting a comparison of the UV and fluorescence profiles generated by post-column labeling for a digest of M118-REH analyzed by Ion-pairing RP HPLC. The top trace reflects UV 232 nm detection, and the bottom trace reflects fluorescence detection at 410 nm. The species labeled by arrows show up mainly in the fluorescence profile and are not observed in the UV profile; they represent non-reducing end saccharides of M118-REH chains that arise from the starting UFH.

The profile enzyme digest for M118-REH as observed by CE is shown in FIG. 2. Notably, no modifying building blocks beyond those already present in UFH were observed in M118-REH (indicated by the 1,6 structures observed for enoxaparin). Another interesting observation was that the amount of 3-O-sulfated species was almost doubled in R-REH as compared to enoxaparin (indicated by the AT-III tetra peak). This correlated well with the higher anti-Xa activity observed for this mixture and was consistent with the methodology for production of M118-REH. The extent of overall sulfation was also shown to be slightly higher for M118-REH than enoxaparin based on this technique.

This technique was also used to determine the presence and quantity of each of the building block saccharide components of M118-REH (Table 12).

TABLE 7

Building block saccharides observed in CE analysis of M118-REH

| Peak | Structure |
|---|---|
| 1 | $\Delta U_{2S}H_{NS,6S}$ |
| 2 | $\Delta U_{2S}H_{NS}$ |
| 3 | $\Delta UH_{NS,6S}$ |
| 4 | $\Delta U_{2S}H_{NAc,6S}$ |
| 5 | $\Delta UH_{NS}$ |
| 6 | $\Delta U_{2S}H_{NAc}$ |
| 7 | $\Delta UH_{NAc,6S}$ |
| 8 | $\Delta UH_{NAc}$ |
| 9 | $\Delta UH_{NAc,6S}GH_{NS,3S}$ |
| 10 | $\Delta UH_{NAc,6S}GH_{NS,3S,6S}$ |
| 11 | $\Delta U_{2S}H_{NS,6S}I_{2S}$ |
| 12 | $\Delta U_{2S}H_{NS,6S}GH_{NS,3S,6S}$ |
| 13 | $\Delta U_{gal}H_{NS,6S}$ |
| 14 | $\Delta U_{gal}H_{NS}$ |

Qualitatively, no 1,6-anhydro building blocks (observed in enoxaparin) or 2,5-anhydro structure (seen in dalteparin) were observed in the M118-REH profile. Some interesting observations arise from the quantitative analysis of these structures. When comparing the relative mole % of peak 10 ($\Delta UH_{NAc,6S}GH_{NS,3S,6S}$) between enoxaparin and M118-REH, a higher amount of the peak was present in M118-REH (Table 6), confirming that the M118-REH manufacturing process enriched for the active anticoagulant sequences in heparin. The amount of trisaccharide ($\Delta U_{2S}H_{NS,6S}I_{2S}$) was relatively low in M118-REH as compared to enoxaparin. This is a reflection of the process for manufacture. The chemical process used to make enoxaparin results in "peeling" from the reducing end of oligosaccharides, thereby increasing the number of odd numbered chains. This is not the case for M118-REH and so the level of trisaccharide was direct consequence of what was observed in the starting UFH. This analysis indicates that the CE methodology was sensitive enough to actually pick up these changes that are indicative of different processes used for manufacturing LMWHs and so it can be very discriminatory.

TABLE 8

Quantitative comparison of selected structures:
M118-REH and enoxaparin

| Structure | M118 | Enoxaparin |
|---|---|---|
| $\Delta UH_{NAc,6S}GH_{NS,3S,6S}$ | 8.6 | 4.7 |
| $\Delta U_{2S}H_{NS,6S}I_{2S}$ | 0.6 | 1.9 |

Compositional Analysis by 2D NMR

NMR spectroscopy has been successfully used for detecting and quantifying signals associated with major or minor structural features in polysaccharides. NMR spectroscopy is also one of the only techniques that allow an effective determination of the iduronic and glucuronic acid components in the mixture. Two dimensional (2D)NMR spectroscopy has been used as a means of resolving and identifying distinct signals that correspond to a certain population of monosaccharide residues. This approach enables one to not only quantify the basic monosaccharide constituents of the mixture, but to also assess their linkage environments in a quantitative manner.

Two dimensional NMR provides a complementary technique to the compositional analysis of M118-REH by CE. 2D NMR provides information on H-U linked disaccharides, thereby providing complementary analysis of disaccharide linkages. Recent methodology using 2D proton-carbon correlation spectroscopy (HSQC) experiments has demonstrated the ability to obtain this quantitative compositional analysis on glycosaminoglycans.

Figure 4:
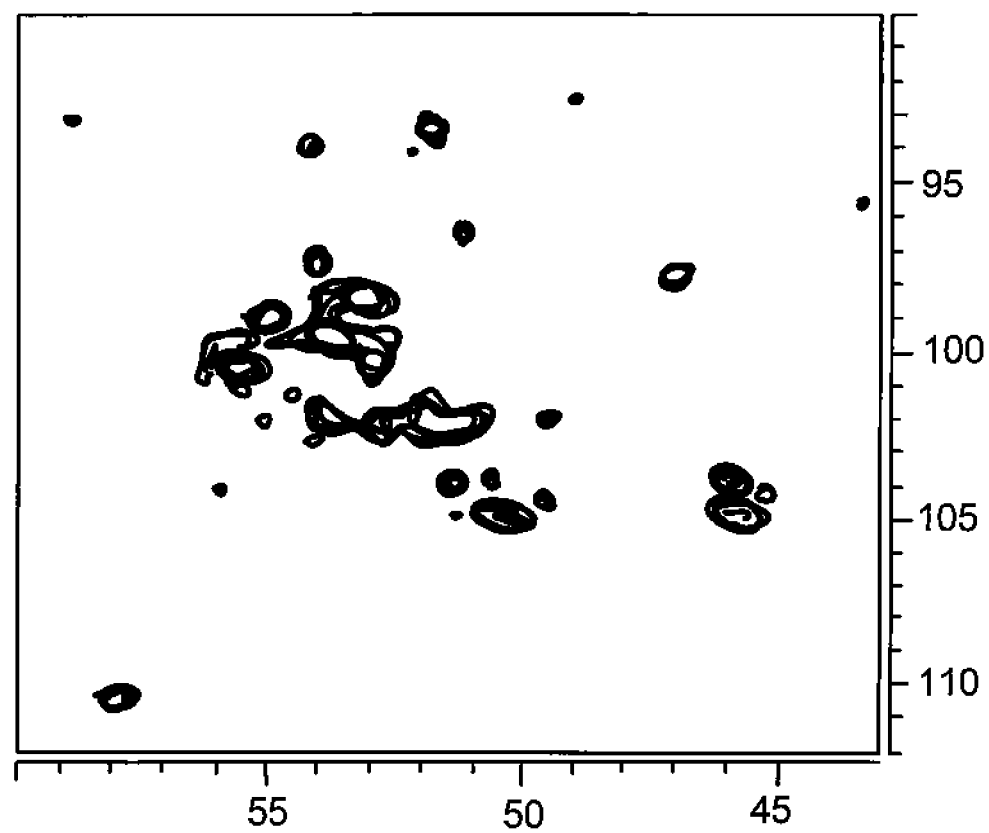
FIG. 4 is graph depicting a two-dimensional NMR HSQC analysis of M118-REH.

Spectra of the anomeric region of M118-REH, as measured using 2D proton-carbon correlation spectroscopy (HSQC) are presented in FIG. 4. The cross peaks in the anomeric region are shown in the Figure.

An analysis of the anomeric region of M118-REH provided some very interesting information regarding what makes M118-REH unique compared to other LMWHs. First, the anomeric region is much simpler when compared to other LMWHs, like enoxaparin. Second, when analyzing the reducing end residues of the chains, it was observed that a majority of the chains end in N-acetylglucosamine, and only a minor amount of the chains end in N-sulfoglucosamine. This arises as a result of the specificity of the enzyme used to prepare M118-REH. Third, the NMR data indicate that ~30% of the chains have a $\Delta U$ residue at the non-reducing end, which is, again, a result of the enzyme specificity. Fourth, no G-$H_{NAc}$ disaccharide was observed in M118-REH. Finally, no linkage region saccharide was observed in the NMR spectrum. The percentage composition of monosaccharides in M118-REH and their linkage environments are reported in Table 7. NMR analysis also enables determination of the iduronic acid/glucuronic acid ratio for M118-REH.

TABLE 9

Percentage composition of glucosamine and uronic acid residues in M-118 (results of two experiments)

| | M118-REH |
|---|---|
| Glucosamine | |
| $H_{NS}$-($I_{2S}$) | 57.6/57.0 |
| $H_{NS}$-(I) | 9.8/12.0 |

TABLE 9-continued

Percentage composition of glucosamine and uronic acid residues in M-118 (results of two experiments)

| | M118-REH |
|---|---|
| $H_{NS}$-(G) | 11.0/11.1 |
| $H_{NAc\ (internal)}$ | 6.1/3.1 |
| $H_{NS,3S}$ | 7.3/7.2 |
| $H_{NS}$red | 1.6/1.5 |
| $H_{NAc}\alpha$redox | 4.6/5.1 |
| $H_{NAc}\beta$redox | 2.0/3.0 |
| $H_{6S}$ | 90.4/90.5 |
| L.R. | 0/<0.1 |
| Uronates | |
| $\Delta U$ | 1.9/2.4 |
| $I_{2S}$ | 68.7/70.2 |
| I-($H_{NS/Ac,6S}$) | 9.9/9.5 |
| I-($H_{NS/Ac}$) | 1.4/0.9 |
| G-($H_{NS}$) | 8.7/7.7 |
| G-($H_{NS,3S}$) | 5.9/4.8 |
| G-($H_{NAc}$) | 0/0 |
| GalA | 2.7 |
| Epox | 0.8 |

Conclusions

The following were identified as structural attributes of M118-REH:

Enrichment of 3-O-sulfate containing saccharide chains (AT-III binding tetrasaccharide) based on relative mole % as compared to existing LMWHs and the UFH starting material;

Generation of a predominant reducing end structure ($H_{NAc}$);

The only modified non-reducing end structure observed is $\Delta U$;

Maintenance of the natural disaccharide backbone structure of UFH with limited introduction of process-related changes that are observed in other LMWHs;

Removal of UFH components from the mixture that are not required for anti-Xa or anti-IIa (thrombin) binding, thereby creating a more defined heparin;

The specificity of the M118-REH depolymerization process retains the required chain length and proximal separation of the binding sites in order to retain anti-IIa activity.

Figure 5:
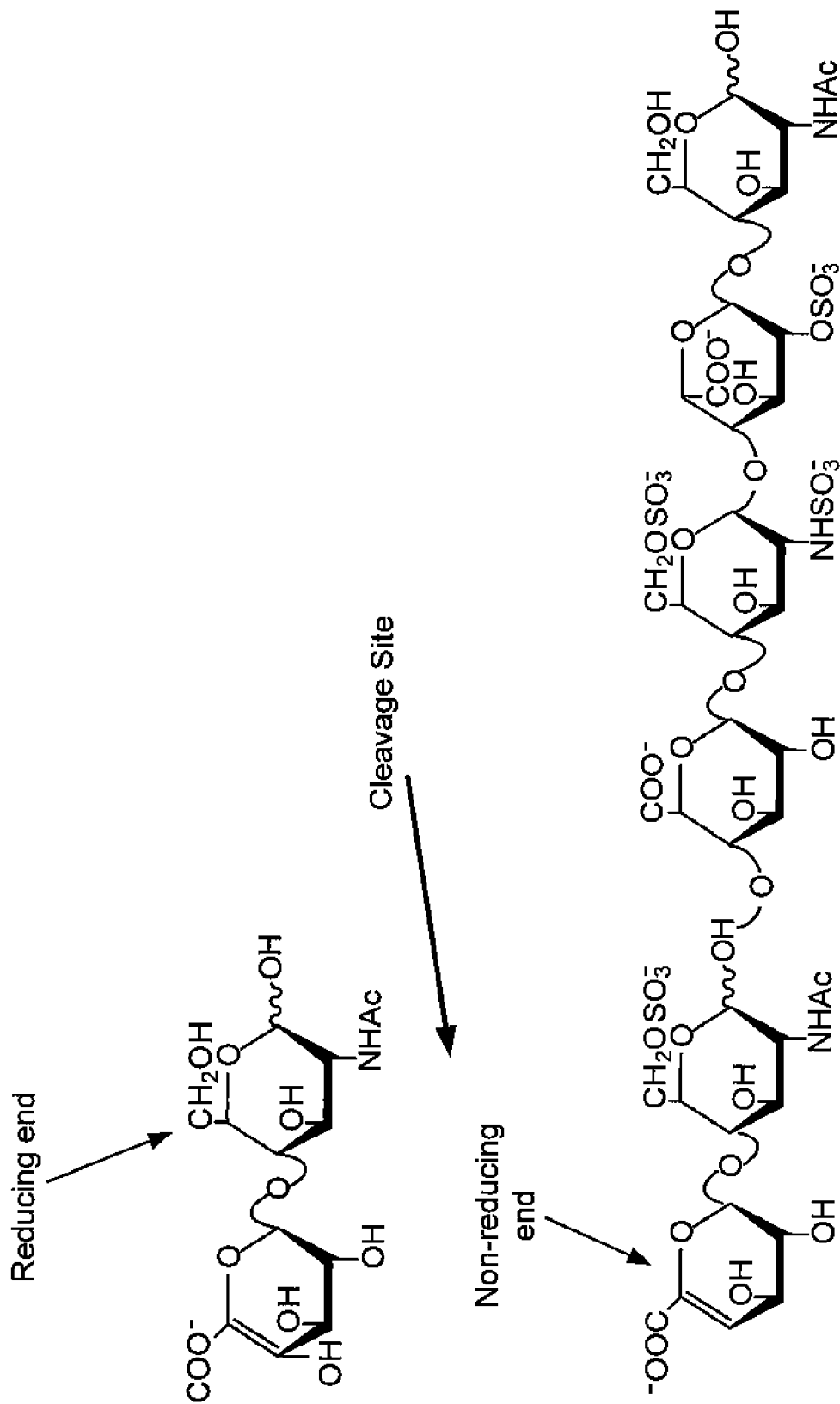
FIG. 5 is a diagram depicting formation of reducing and non-reducing ends.

A key attribute of all LMWH products is that longer polysaccharide chains are cleaved into smaller fragments via a variety of depolymerization methods, as depicted in FIG. 5. This cleavage event, which can be caused by either chemical or enzymatic reactions, results in characteristic signatures at both the reducing and non-reducing ends of the molecule. The characteristic end groups present is M118-REH are described below.

Structure at the Non-Reducing End

The specificity of the enzymatic cleavage that resulted in the formation of a new non-reducing end (abbreviated as $\Delta U$), enabled the positioning of the AT-III binding site within the polysaccharide chain.

Structure at the Reducing End

The glucosamine structures at the new reducing ends on the M118-REH chains were reflective of the specificity of the enzyme used in the process. As a result, the majority of the reducing end structures in M118-REH were N-acetylated hexosamine ($H_{NAc}$) residues.

Structural Differences Between M118-REH and Unfractionated Heparin

1) M118-REH has a higher mole % of the antithrombin binding saccharide sequence as compared to the starting unfractionated heparin (UFH).

2) M118-REH has negligible amount of linkage region as compared to the starting UFH.

3) M118-REH has a certain percentage on Δ4,5 glucuronic acid at the non-reducing end of chains, whereas UFH does not contain this modified residue at the non-reducing end.

In summary, M118-REH is a heparin product having unique physical and functional attributes.

Most of the structural attributes discussed above were a direct consequence of the properties of the enzyme used to prepare M118-REH. These include the predominant reducing end structure ($H_{NAc}$), the only modified non-reducing end structure ($\Delta U$) as well as the removal of linkage region. Also since the enzyme preferentially cleaves the lower or non-sulfated domains in the heparin mixture, it does not affect the AT-III binding sequence, which, as a result, is enriched in M118-REH The characterization protocol defined above was used to analyze 4 batches of M118-REH. This analysis confirms consistency in manufacture of what is defined as M118-REH.

TABLE 10

CE analysis of several batches of M118-REH

| Peak | Structure | #1 | #2 | #3 | #4 |
|---|---|---|---|---|---|
| 1 | $\Delta U_{2S}H_{NS,6S}$ | 57.1 | 59.5 | 57.0 | 57.4 |
| 2 | $\Delta U_{2S}H_{NS}$ | 6.0 | 5.6 | 5.4 | 6.1 |
| 3 | $\Delta UH_{NS,6S}$ | 13.2 | 12.3 | 12.2 | 12.7 |
| 4 | $\Delta U_{2S}H_{NAc,6S}$ | 1.8 | 1.6 | 1.7 | 1.8 |
| 5 | $\Delta UH_{NS}$ | 0.6 | 0.7 | 0.6 | 0.7 |
| 6 | $\Delta U_{2S}H_{NAc}$ | 0.5 | 0.5 | 0.4 | 0.4 |
| 7 | $\Delta UH_{NAc,6S}$ | 4.5 | 3.7 | 3.7 | 4.3 |
| 8 | $\Delta UH_{NAc}$ | 1.8 | 1.3 | 1.5 | 1.8 |
| 9 | $\Delta UH_{NAc,6S}GH_{NS,3S}$ | 1.3 | 1.0 | 1.2 | 1.2 |
| 10 | $\Delta UH_{NAc,6S}GH_{NS,3S,6S}$ | 10.4 | 9.4 | 8.9 | 8.6 |
| 11 | $\Delta U_{2S}H_{NS,6S}I_{2S}$ | 0.3 | 0.3 | 0.7 | 0.6 |
| 12 | $\Delta U_{2S}H_{NS,6S}GH_{NS,3S,6S}$ | 0.5 | 0.7 | 1.0 | 0.9 |
| 13 | $\Delta U_{gal}H_{NS,6S}$ | 1.7 | 2.9 | 4.4 | 3.0 |
| 14 | $\Delta U_{gal}H_{NS}$ | 0.2 | 0.5 | 0.9 | 0.4 |

TABLE 10A

Preferred ranges for peaks

| Peak | Structure | A |
|---|---|---|
| 1 | $\Delta U_{2S}H_{NS,6S}$ | 58 ± 5 |
| 2 | $\Delta U_{2S}H_{NS}$ | 6 ± 2.5 |
| 3 | $\Delta UH_{NS,6S}$ | 13 ± 3 |
| 4 | $\Delta U_{2S}H_{NAc,6S}$ | 1.5 ± 1.5 |
| 5 | $\Delta UH_{NS}$ | 0.6 ± 1.0 |
| 6 | $\Delta U_{2S}H_{NAc}$ | 0.5 ± 1.0 |
| 7 | $\Delta UH_{NAc,6S}$ | 4 ± 2 |
| 8 | $\Delta UH_{NAc}$ | 1.5 ± 2.0 |
| 9 | $\Delta UH_{NAc,6S}GH_{NS,3S}$ | 1.2 ± 1.5 |
| 10 | $\Delta UH_{NAc,6S}GH_{NS,3S,6S}$ | 9.5 ± 4 |
| 11 | $\Delta U_{2S}H_{NS,6S}I_{2S}$ | 0.5 ± 1.0 |
| 12 | $\Delta U_{2S}H_{NS,6S}GH_{NS,3S,6S}$ | 0.7 ± 2.0 |
| 13 | $\Delta U_{gal}H_{NS,6S}$ | 3.0 ± 3.0 |
| 14 | $\Delta U_{gal}H_{NS}$ | 0.6 ± 1.5 |

TABLE 11

Percent composition of M118-REH glucosamine and uronic acid residues

| Monosaccharide | 1 | 2 | 3 | 4 |
|---|---|---|---|---|
| Glucosamine | | | | |
| $H_{NS}$-($I_{2S}$) | 54.3 | 57.0 | 61.8 | 57.6 |
| $H_{NS}$-(I) | 12.5 | 12.0 | 11.0 | 9.8 |
| $H_{NS}$-(G) | 10.8 | 11.1 | 9.5 | 11.0 |
| $H_{NAc\ (internal)}$ | 3.4 | 3.1 | 4.2 | 6.1 |
| $H_{NS,3S}$ | 8.7 | 7.2 | 7.0 | 7.3 |
| $H_{NS}$red | 0.8 | 1.5 | 0.4 | 1.6 |
| $H_{NAc}\alpha$red | 6.0 | 5.1 | 4.1 | 4.6 |
| $H_{NAc}\beta$red | 3.6 | 3.0 | 2.0 | 2.0 |
| $H_{6S}$ | 90.0 | 90.5 | 91.3 | 90.4 |
| Linkage Region | <0.1 | <0.1 | <0.1 | <0.1 |
| Uronates | | | | |
| ΔU | 2.7 | 2.4 | 2.1 | 1.9 |
| I2S | 69.8 | 70.2 | 70.6 | 68.7 |
| I-($H_{NS/Ac,6S}$) | 11.8 | 9.5 | 9.2 | 9.9 |
| I-($H_{NS/Ac}$) | 1.4 | 0.9 | 1.2 | 1.4 |
| G-($H_{NS}$) | 8.9 | 7.7 | 8.4 | 8.7 |
| G-($H_{NS,3S}$) | 5.4 | 4.8 | 4.1 | 5.9 |
| G-($H_{NAc}$) | 0 | 0 | 0 | 0 |
| Galacturonic Acid | 0 | 2.1 | 2.4 | 2.7 |
| Epoxide | 0 | 2.4 | 2.0 | 0.8 |

TABLE 11A

Preferred ranges for structures

| Monosaccharide | A |
|---|---|
| Glucosamine | |
| $H_{NS}$-($I_{2S}$) | 57.7 ± 7 |
| $H_{NS}$-(I) | 11.3 ± 5 |
| $H_{NS}$-(G) | 10.6 ± 5 |
| $H_{NAc\ (internal)}$ | 4.2 ± 5 |
| $H_{NS,3S}$ | 7.6 ± 5 |
| $H_{NS}$red | 1.1 ± 5 |
| $H_{NAc}\alpha$red | 5.0 ± 5 |
| $H_{NAc}\beta$red | 2.7 ± 5 |
| $H_{6S}$ | 90.6 ± 6 |
| Linkage Region | <0.1-0.0 |
| Uronates | |
| ΔU | 2.3 ± 5 |
| I2S | 69.8 ± 6 |
| I-($H_{NS/Ac,6S}$) | 10.1 ± 6 |
| I-($H_{NS/Ac}$) | 1.2 ± 5 |
| G-($H_{NS}$) | 8.4 ± 5 |
| G-($H_{NS,3S}$) | 5.1 ± 5 |
| G-($H_{NAc}$) | 0 + 2 |
| Galacturonic Acid | 1.8 ± 5 |
| Epoxide | 1.3 ± 5 |

Description and Composition of the Drug Product M118-REH Injection

The drug product, M118-REH Injection, is a clear, colorless to slightly yellow solution in a 3 mL single use, Type 1 glass vial, sealed with a chlorobutyl stopper and oversealed with an aluminum crimp. Each vial nominally contains 5000 IU of anti-factor Xa activity in 2 mL.

The quantitative composition of M118-REH Injection is given in Table 11. The composition is given for the labeled volume of 2 mL. The vials were filled with 2.15 mL, consistent with the USP recommended excess volume.

TABLE 12

Composition of M118-REH Injection

| Component | Amount per unit (Vial) | Function | Quality Standard |
|---|---|---|---|
| M118-REH Drug Substance | 5000 IU anti-Xa activity[1] | Active Pharmaceutical Ingredient | N/A |
| Sodium Chloride | In-process OSmolality Adjustment[2] | Osmolality Agent | USP |
| Water for Injection | q.s. to 2 mL | Solvent | USP |

[1]The amount of M118-REH drug substance is calculated based on the anti-factor Xa activity (on a dried basis) and the Loss on Drying. Assuming anti-factor Xa activity of 200 IU/mg, the quantity of M118-REH drug substance is 25 mg per vial.
[2]The quantity of Sodium Chloride required to achieve an osmolality of 280-330 mOsm/L is approximately 8 mg/mL, or 16 mg per vial.

No diluent was required for use with M118-REH Injection.

Components of M118-REH Injection

M118-REH Injection was manufactured by dissolving M118-REH Drug Substance in Water for Injection. M118-REH Drug Substance is very soluble in aqueous solution and the particle size distribution of drug substance therefore had no effect on the performance of the drug product.

Sodium Chloride, USP was the only excipient used in M118-REH Injection (at a concentration of approximately 8 bg/mL). Sodium chloride was selected as an osmolality adjusting agent to avoid injection site discomfort and haemolysis upon administration.

Manufacturing Process Development of M118-REH Injection

The M118-REH Injection manufacturing process consisted of dissolving the M118-REH drug substance in Water for Injection, USP, and adjusting the osmolality with Sodium chloride, USP. The formulated solution was filtered through two 0.2 pm filters in series and aseptically filled into vials. Heparin sodium products are subject to degradation at very high temperatures and therefore cannot be terminally sterilized. The process flow diagram for M118-REH Injection is presented in FIG. 6 (described below).

Figure 6:
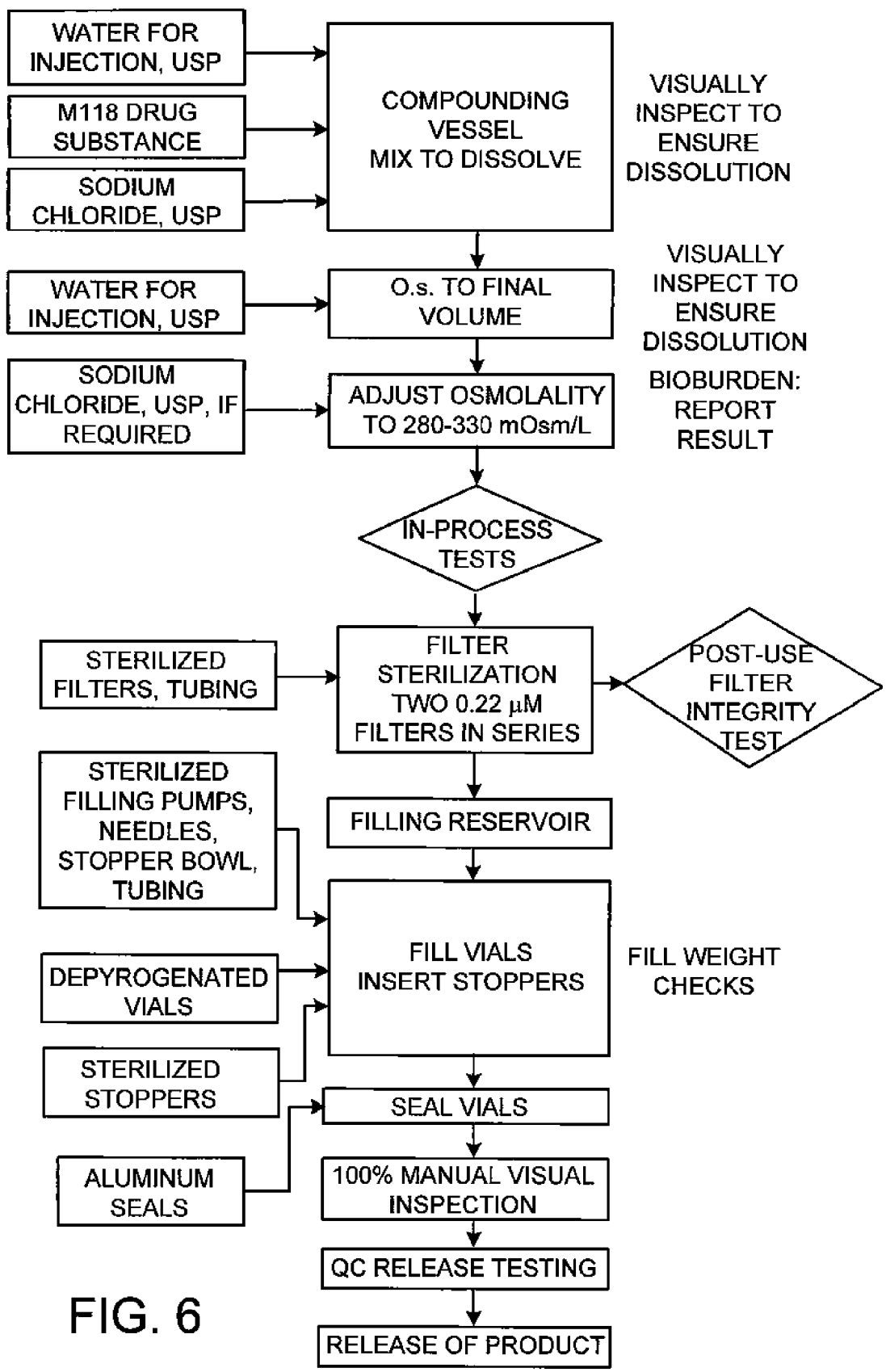
FIG. 6 is a manufacturing process flow diagram of M118-REH Injectable.

FIG. 6 shows a process flow diagram for M118-REH Injection. The amount of M118-REH drug substance to be added to each batch was calculated based on the Assay (anti-factor Xa activity) and Loss on Drying values from the Certificate of Analysis according to the following calculation:

2500 IU/mL/Assay (IU/mg)×100/(100−Loss on Drying %)×Batch size (mL)÷1000 mg/g=Quantity of Drug Substance to add (g)

Water for Injection equivalent to approximately 75% of the final batch weight was added to the formulation vessel and mixing was initiated. The calculated amount of M118-REH drug substance was slowly added to the vessel and mixed until all solid was dissolved. An initial quantity of Sodium Chloride USP was added and the solution was mixed until all solid was dissolved. Water for Injection was added to the final batch weight and the solution was mixed for an additional 5-15 minutes. The osmolality was measured, and additional Sodium Chloride USP was added, if required, to achieve an osmolality of 280-330 mOsm/L.

Two pre-sterilized Millipak 20 PVDF (polyvinylidene fluoride) 0.22 µm filters in series were used to sterilize the M118-REH bulk drug product. The product was filtered into a filling reservoir, and, at the end of filtration, the filters were integrity tested.

Biological and Pharmacological Properties of M118-REH

M118-REH is the product of an enzymatic digest that results in a depolymerized low molecular weight heparin. The depolymerized pool is enriched for active anticoagulation and antithrombotic fractions, which may be a consequence of the site specific digestion by a specific glycosaminoglycan lyase. The specific site and orientation depolymerization via this enzyme has enabled M118-REH to be a highly efficacious molecule on artery injury protection. Furthermore, M118-REH has the attribute of being reversible and easily monitored by bedside clotting assays.

Studies of M118-REH have been done to reveal the pharmacologic and biologic properties of M118-REH, and through this process, its mode of actions have been explored both in vitro and in vivo. The mechanism of anti-coagulation and anti-thrombotic function have been investigated. The preliminary Structure and Activity Relationship (SAR) has been addressed in these studies. These studies and their results are described as the following, which are initial analyses for generating the profile of M118-REH's biopharmacologic activities.

In Vitro Analysis of Coagulation Activity:

In vitro anti-Xa activity of M118-REH ranges from 180-300 IU/mg based on 2nd international low molecular weight heparin standards. M118-REH preparations higher in vitro anti-Xa/IIa activities are proportional to its fraction as $\Delta UH\text{-}Nac,6sGH_{NS,3S,6S}$ containing 3-O-sulfation moiety.

In vitro anti-IIa activity of M118-REH ranges from 100-250 IU/mg based on $2^{nd}$ international low molecular weight heparin standards.

M118-REH can prolong the aPTT in vitro from 40 sec to 80 sec. at 2.4 μg/ml and aPTT change is propositional to the anti-Xa and anti-IIa activity.

Figure 7:
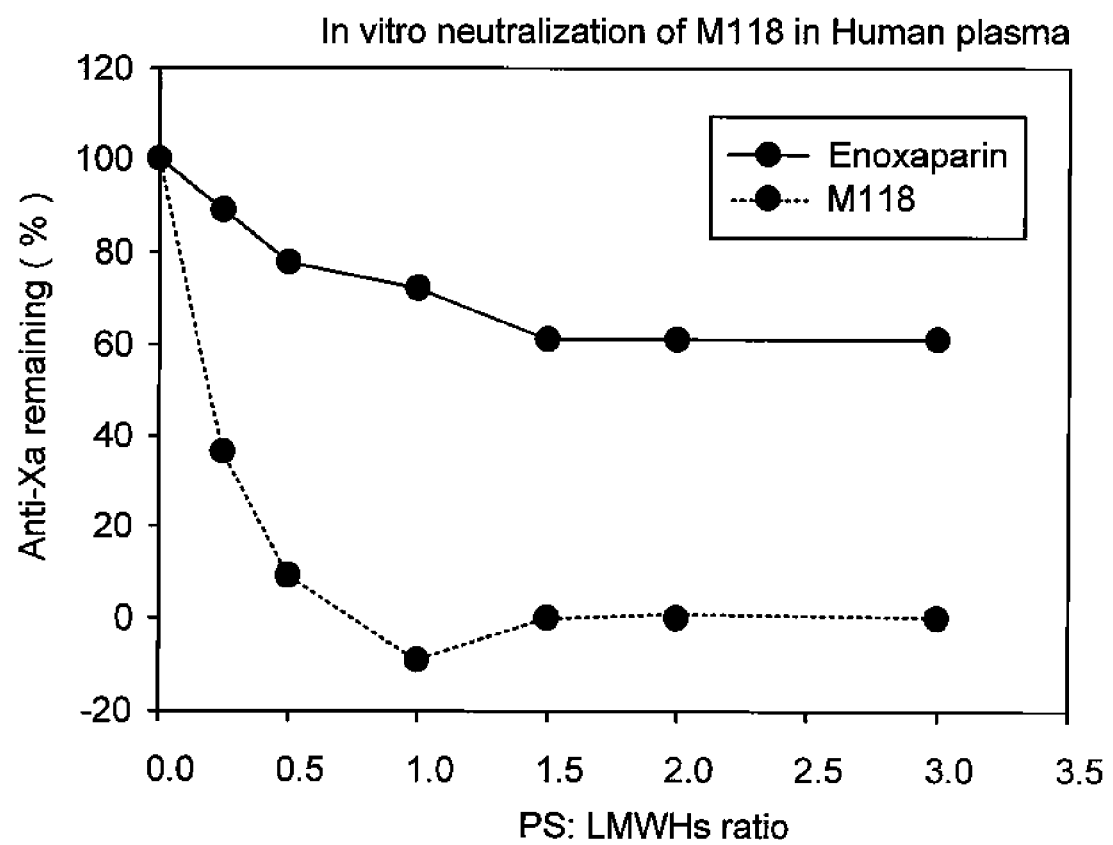
FIG. 7 is a graph depicting in vitro neutralization of LMWHs by protamine sulfate. "M118" (shorthand in this figure for M118-REH) is represented by a lighter dot; enoxaparin sodium is represented by a darker dot. Graph was plotted with percentage of remaining anti-Xa activity against the ratio of protamine to LMWHs activity.

In Vitro Neutralization by Protamine Sulfate and Measured by Anti-Xa Activity:

Protamine can fully reverse the anti-Xa activity of M118-REH at ratio of 1 mg:100 anti-Xa IU in human plasma. This can be compared to other LMWH preparations. For example, protamine can only neutralize 60% anti-Xa activity of enoxaparin at ratio of 3 mg: 100 anti-Xa IU in human plasma. These results are shown in FIG. 7.

In Vitro Human Umbilical Vein Endothelial Cells (HUVECs) Release Tissue Factor Pathway Inhibitor (TFPI):

HUVECs from ATCC were grown in 2% FBS F12K modified medium without ECGS. M118-REH, Lovenox, and UFH were prepared in the same medium with the final concentration of 0.01 mg/ml and 0.005 mg/ml. Three wells of cells for each group were incubated under 37° C., 5% $CO_2$, and 95% $O_2$ for 24 and 48 hours. The supernatant was taken out for TFPI release test using ELISA kit from ADI.

Figure 8:
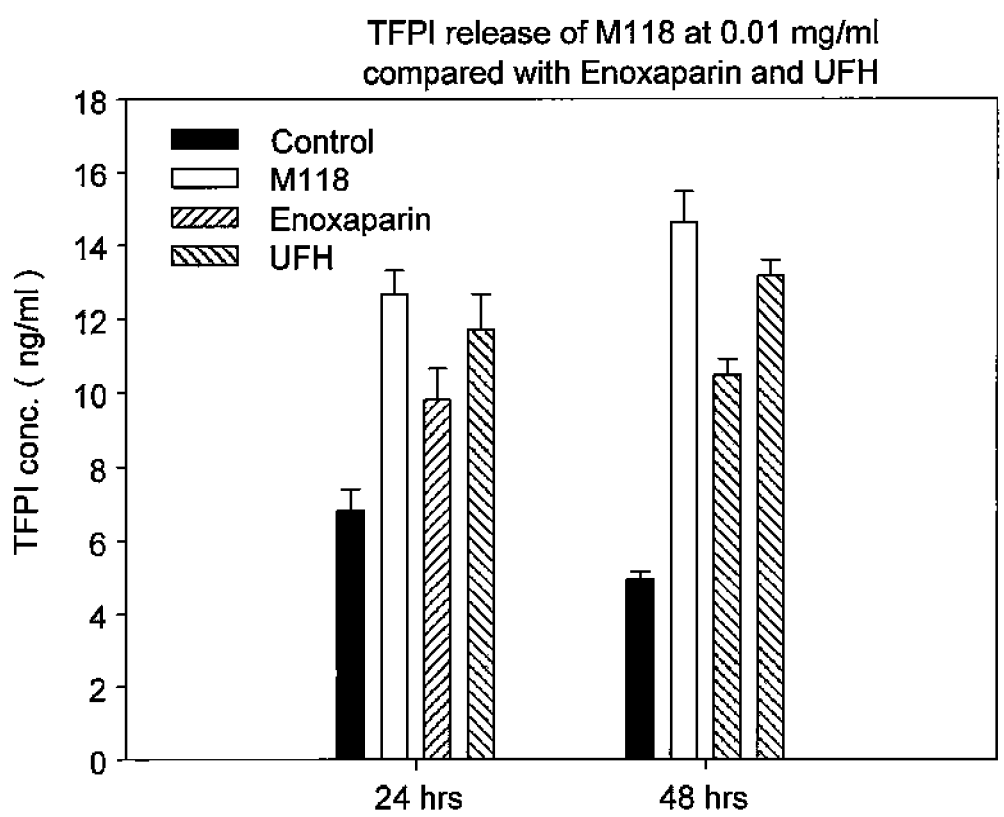
FIG. 8 is a graph depicting TFPI release from human umbilical vein endothelial cells (HUVEC) by different heparins at 0.01 mg/ml (wells n=3, mean±STDEM). There is a statistically significance between M118 (which is shorthand for M118-REH in this figure) (second bar from the left in each group) and control (first bar from the left in each group) and control groups ($p<0.01$) after both 24 and 48 hours incubation.

M118-REH at 0.005 mg/ml and 0.01 mg/ml significantly increased the TFPI release from HUVECs at 24 and 48 hours and, as shown in FIG. 8. M118-REH resulted in more release of TFPI from HUVECs into cell medium than unfractionated heparin. Lovenox did not cause a significantly higher TFPI release when compared with control.

Pharmacokinetics of M118-REH In Vivo:

In rodent models such as Sprague-Dawley rats and B16B16 mice, M118-REH has longer elimination half life than UFH and comparable to that of enoxaparin after intravenous injection. M118-REH is quickly absorbed after subcutaneous injection with $T_{max}$ ranged from 1 hour to 3 hours.

In rabbit model such New Zealand white rabbit, M118-REH subcutaneous injection yields higher bioavailability in terms of both anti-Xa and anti-IIa activity than that of UFH, the bioavailability ranged from 50% to 100% compared with intravenous injection. The pharmacokinetics of M118-REH is comparable to that of enoxaparin with elimination half life ranged from 3-5 hours and the major elimination mechanism is through renal excretion.

TABLE 13

Pharmacokinetics parameters of M118-REH, enoxaparin and UFH after intravenous injection in a rabbit and rat model.

|  |  | M118-REH | Enoxaparin | UFH |
| --- | --- | --- | --- | --- |
| T½ (hr) Rabbit i.v 1.5 mg/kg | Anti-Xa activity | 0.87 ± 0.25 | 1.93 ± 0.45 | 0.54 ± 0.03 |
|  | Anti-IIa activity | 0.85 ± 0.05 | 1.78 ± 0.63 | 0.89 ± 0.05 |
| T1/s (hr) Rat i.v 0.5 mg/kg | 1 mg/kg Anti-Xa | 0.39 ± 0.06 0.29 ± 0.12 | 0.41 ± 0.07 N/A | 0.35 ± 0.06 0.19 ± 0.04 |

In NHP, such as Cytomologus monkey, the elimination half life of M118-REH ranged from 20 minutes to 50 minutes. The anti-Xa/IIa ratio after intravenous injection was kept consistent during the PK course which ranged from 0.5 to 2 and M118-REH was distributed in the circulation system and eliminated through renal route based on the analysis of pharmacokinetic parameters. Table 14 depicts pharmacokinetics of M118-REH in NHP model.

TABLE 14

Pharmacokinetics of M118-REH in NHP.

| Test material | Group |  | Dose (IU/kg) | Rsq | t½ (hr) | Cmax (IU/mL) | AUCINF_obs (hr * IU/Ml) | Vz_obs (mL/kg) | Cl_obs (mL/hr/kg) |
| --- | --- | --- | --- | --- | --- | --- | --- | --- | --- |
| Anti-Xa | 1 | Mean | 150.0 | 0.98 | 0.50 | 4.07 | 4.07 | 27.26 | 37.24 |
|  |  | SD | 0.9 | 0.02 | 0.04 | 0.15 | 0.54 | 5.57 | 4.65 |
| Anti-IIa | 2 | Mean | 150 | 1.0 | 0.68 | 2.733 | 3.45 | 43.17 | 43.92 |
|  |  | SD | 0.0 | 0.01 | 0.05 | 0.38 | 0.45 | 3.66 | 5.38 |

The pharmacokinetics of M118-REH represents the first order of elimination.

In vivo TFPI concentration remained at high levels over 24 hours after M118-REH dosing. ACT and aPTT both correlated very well with the anti-Xa activity.

Pharmacodynamics Study of M118-REH In Vivo:

In rodent models such as Sprague-Dawley rat, M118-REH and UFH were intravenously injected at 1 or 2 mg/kg via jugular vein, while enoxaparin was dosed at 0.5 or 1 mg/kg. ACT (activated clotting time) was measured with Hemochron Jr. In this model, activated partial thromboplastin time (aPTT) and activated clotting time presented dose response to M118-REH escalating dosages. ACT increased 1.5-3 folds after M118-REH delivery at 0.5 mg/kg while 2-4 folds at 1 mg/kg after intravenous injection. The pharmacodynamic profile was similar to that of the pharmacokinetics in terms of anti-Xa/IIa measurement; the elimination half life ranges from 0.15 to 0.5 hour.

In a rabbit model such as New Zealand white rabbit, aPTT and ACT were measured after M118-REH delivery intravenously. aPTT and ACT increased proportional to M118-REH dose. The anti-Xa/IIa ratios were consistent after both intravenous and subcutaneous administration at 1.5 mg/kg. In contrast to those of M118-REH, the anti-Xa/IIa ratios of both enoxaparin and UFH after intravenous administration fluctuated significantly during the course.

Figure 9:
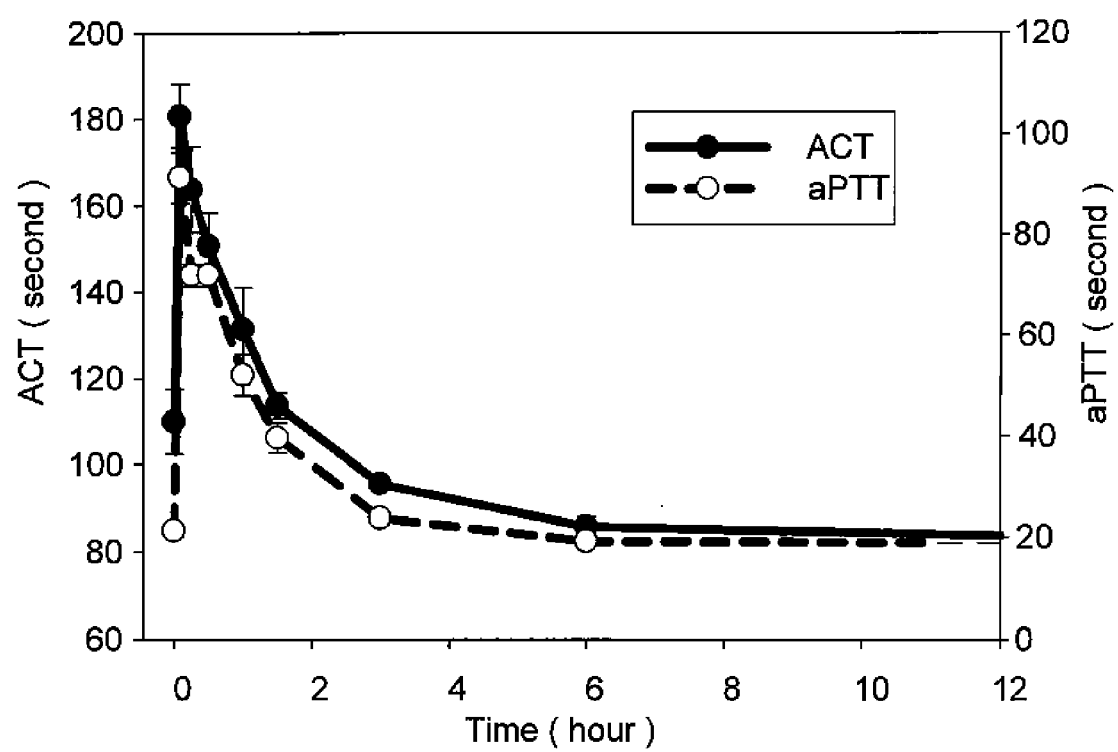
FIG. 9 is a graph depicting the pharmacodynamics of M118-REH by measuring ACT and aPTT after intravenous injection in the NHP model.

As shown in FIG. 9, in NHP models such as Cynomologus monkey, the results showed that aPTT and ACT increased significantly 2-4 folds and 1.5-3 folds after M118-REH intravenous injection at 150 anti-Xa IU/kg.

M118-REH intravenous bolus injection enhanced TFPI release into the blood stream by 2-20 folds and such effects last more than 24 hours.

The effects of M118-REH intravenous bolus injection followed by continuous infusion were also studied in a canine model of deep arterial thrombosis induced by severe electrolytic injury. More details regarding this study are provided below in the Example entitled "Beagle electrolytic-induced femoral artery injury model".

Efficacy Study of M118-REH in Preclinical Models:

Ferric Chloride-Induced Carotid Artery Injury

Figure 10:
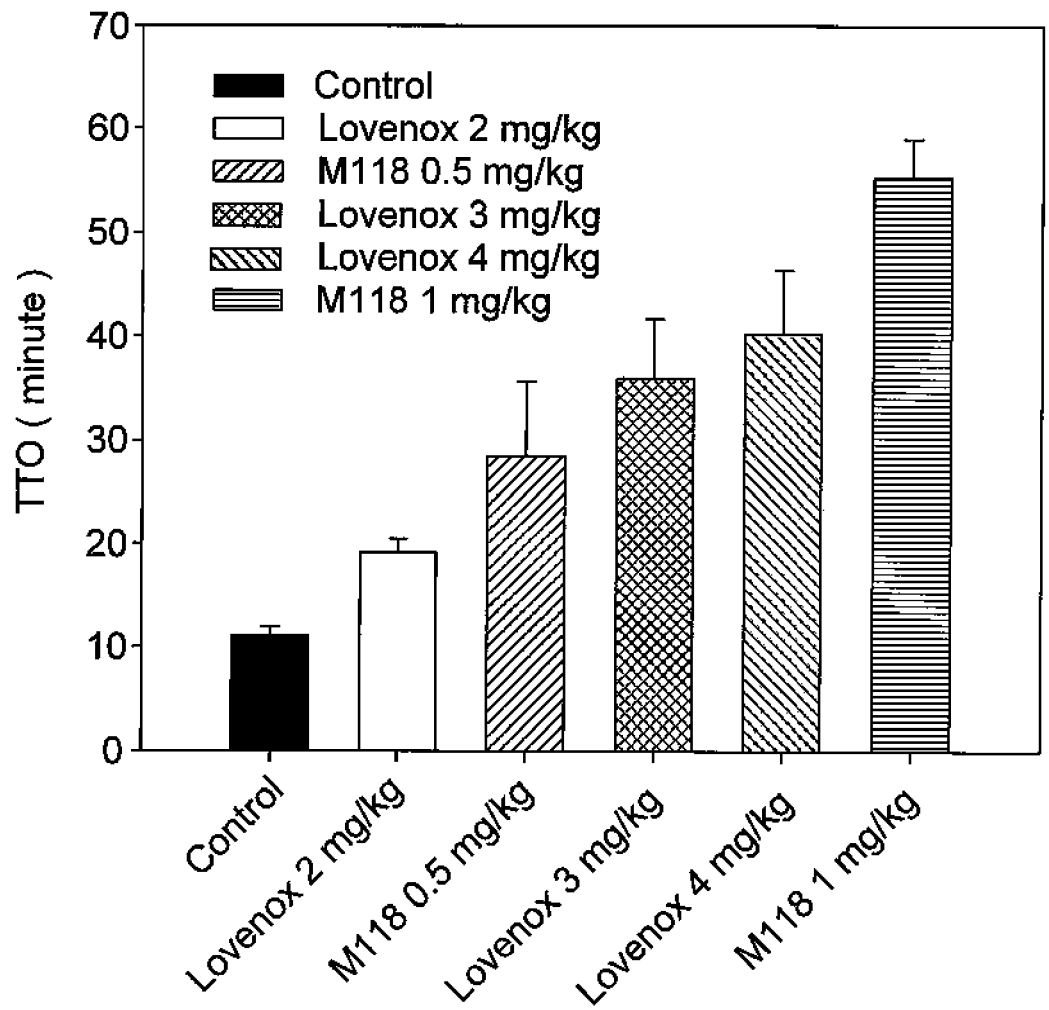
FIG. 10 is a graph depicting comparison of TTO of M118-REH 0.5 (third column) and 1 mg/kg (sixth column) with enoxaparin sodium 2, 3 and 4 mg/kg (second, fourth, and fifth, respectively) intravenously injected in ferric chloride induced thrombosis model. All treatment groups have significant longer TTO compared with Control (first column). There is a statistical significant difference between M118-REH (1 mg/kg) and enoxaparin sodium 3 mg/kg ($p<0.01$).

Comparison studies of M118-REH and enoxaparin yielded dose-dependent inhibition of occlusive thrombosis. M118-REH at a dose of 0.5 mg/kg significantly ($p<0.05$) prolonged the time to occlusion (TTO) compared to saline ($28.5 \pm 7.1$ minutes versus $11.1 \pm 0.9$ minutes, respectively). Twenty-five percent (2/8) of the injured carotid artery injected with 0.5 mg/kg M118-REH remained patent for the entire 60 minute observation period. In contrast, all (9/9) of the injured carotid arteries occluded in rats injected with saline within the 60 minute observation period. Administration of 1 mg/kg of M118-REH further increased TTO ($55.3 \pm 3.6$ minutes) with 83% (10/12) of the vessels patent at the end of the 60 minutes observation period. Rats administered 2, 3 or 4 mg/kg of enoxaparin all had significantly longer TTO than animals injected with saline ($19.1 \pm 1.4$, $36.0 \pm 5.6$ and $40.2 \pm 6.3$ minutes, respectively). All (7/7) of the carotid arteries occluded within the 60 minute observation period at the 2 mg/kg dose while 62% (7/13) and 55% (6/11) vessels occluded in rats administered with 3 and 4 mg/kg enoxaparin, respectively. M118-REH (1 mg/kg) produced the greatest degree of protection from thrombosis in spite of lower anti-Xa activity than that at the 3 and 4 mg/kg doses of enoxaparin. The results are depicted in FIG. 10 and Table 15.

TABLE 15

Statistical Analysis of the Efficacy Data (Student's t-test).

| | Control | M118-REH 0.5 mg/kg | M118-REH 1 mg/kg | Enoxaparin sodium 2 mg/kg | Enoxaparin sodium 3 mg/kg | Enoxaparin sodium 4 mg/kg |
|---|---|---|---|---|---|---|
| Mean (min) | 11.3 | 29.2** | 55.3#** | 23.2** | 36.0** | 41.8** |
| St. Dev. | 2.3 | 16.8 | 12.6 | 8.3 | 20.3 | 20.6 |

*$p < 0.05$ compared to control group;
**$p < 0.01$ compared to control group;
$p < 0.01$ compared to enoxaparin sodium 3 mg/kg Beagle Electrolytic-Induced Femoral Artery Injury Model (Lucchesi's Model):

The antithrombotic and anticoagulant effects of M118-REH were studied in a canine model of deep arterial thrombosis induced by severe electrolytic injury.

Surgical Procedures

Animals were premedicated with intramuscular (IM) atropine sulfate (0.02 mg/kg) and IM acepromazine (0.2 mg/kg, ≤3 mg per animal) at least 10-15 minutes prior to induction of anesthesia with IV propofol (4-8 mg/kg). Animals were intubated and maintained in anesthesia via isoflurane inhalant, to effect, through a volume-regulated respirator.

A longitudinal incision was made on the medio-ventral surface of the neck to gain access to the tissues overlying the carotid arteries. One carotid artery and both jugular veins (one for backup) were subsequently exposed for approximately 2 cm by blunt dissection and supported by retaining ligatures at the proximal and distal ends. Two other incisions were made that initiated on the abdomen and extended distally along the pectineus for a distance covering 66%-75% of each femur. The fascia was opened at each incision, and the underlying femoral artery was exposed for a distance of approximately 2-3 cm.

Animal Instrumentation

Twenty four anesthetized beagle dogs were instrumented with intravascular electrodes through the left and right femoral artery walls and positioned in direct contact with the intima. Each electrode was connected to a constant amperage power source, with the cathode placed at a distant subcutaneous site. A stenotic device was positioned immediately distal to the electrode, a pervascular Doppler flow probe was positioned proximal to the electrode, and a catheter was inserted into the carotid artery, all of which were connected to a Gould Ponemah Physiological Platform (Linton Instrumentation, Norfolk, UK) for continuous monitoring of arterial blood pressure, blood flow, and heart rate. A second catheter was inserted into the jugular vein for blood sample collection. Finally, an intravenous line was inserted into a peripheral vein for study treatment infusions, and limb leads were placed for electrocardiography (measured at Lead II).

Femoral Artery Electrolytic-Injury Model

After instrumentation, each animal received a continuous IV infusion of vehicle (0.9% sterile saline) for 90 minutes. Fifteen minutes after the infusion started, electrical current (300 µA) was applied to the right femoral artery (control) through the intravascular electrode and administered continuously until full thrombus formation, defined as a reduction in Doppler flow to ≤2% of baseline values, or until the end of the observation period at 180 minutes after initiation of electrolytic injury if the vessel remained patent. Following this, the vessel was ligated proximally and distally to the site of electrolytic injury, the segment was harvested, and any thrombus, if present, was weighed.

In this model, platelet-rich intravascular thrombi form in proximity to a distal arterial stenosis. Accordingly, the stenotic device was adjusted to limit hypoxia-induced reactive hyperemia to ≤80% of the baseline response to physical occlusion (baseline reactive hyperemia was determined at each femoral artery immediately prior to vehicle or active-treatment infusions). To ensure that hemodynamic properties at the site of injury approximated normal blood flow through the femoral artery, mean arterial pressure and heart rate were targeted to approximately 70 mm Hg and 100 beats per minute, respectively, via isoflurane anesthetic management.

After completing the preceding experiment to evaluate baseline thrombotic parameters in each animal at the right femoral artery, identical procedures were carried out at the left femoral artery (active-treated) in the presence of M118-REH or UFH infusions. Animals were allocated in 4 treatment groups (n=6). Three groups received IV boluses of M118-REH at 37.5, 75, and 150 anti-Xa IU/kg, respectively, followed by continuous infusions of M118-REH at 1.0 anti-Xa IU/kg/min for 90 minutes. The fourth group received an IV bolus of UFH at 75 U/kg, followed by a continuous infusion of UFH at 1.0 U/kg/min for 90 minutes. Continuous electrolytic injury was initiated 15 minutes after bolus treatment, and subsequent analyses were carried out identically to the vehicle group.

Assays for cutaneous bleeding time (CBT) and blood collections were carried out at protocol-specified time points (see below). Physiological parameters monitored throughout the procedure included pulse rate, respiration rate, direct blood pressure, rectal temperature, tidal volume, end-tidal carbon dioxide levels, and $O_2$ saturation.

Hematology and Coagulation Determinations

For hematology and coagulation determinations, whole blood samples (approximately 100 μL) were collected at 15, 30, 45, 60, 75, 90, 105, 120, 135, 150, 165, and 180 minutes for determination of ACT. ACT was assessed in a HEMOCHRON® Jr. Signature+ Microcoagulation System (ITC, Edison, N.J., USA) according to the manufacturer's instructions. Two aliquots (approximately 1.3 mL each) of whole blood were collected at 15 minutes, 60 minutes, and either 180 minutes or the time of occlusion, if applicable, for hematological and further coagulation assays. Hematologic parameters (WBC, RBC, HGB, CHT, MCV, MCH, MCHC, PLT, RTC, ARTC, and WBC differentials) were assayed using an Advia 120 Hematology System (Bayer Diagnostics Norden, Lyngby, Denmark) following the manufacturer's instructions. Coagulation assays (prothrombin time [PT], activated partial thromboplastin time [aPTT], and fibrinogen levels [FIB]) were conducted using an MLA Electra 140° C. Coagulation Analyzer (Beckman Coulter, Fullerton, Calif., USA) following the manufacturer's instructions.

To determine anti-Factor Xa and anti-Factor IIa levels, citrated whole blood samples collected at 0, 15, and 60 minutes after initiation of treatment were centrifuged at 3,000 g for approximately 10 minutes in a refrigerated centrifuge. Plasma was collected, snap frozen at −20° C., and stored at −80° C. until ready for testing by chromogenic assay. Stachrome Heparin Anti-Xa kit (Diagnostica Stago, Asnieres sur Seine, France) and a reagent set consisting of substrate S2238, bovine thrombin, and human antithrombin III (Chromogenix, Milano, Italy) were used for the anti-Factor Xa and anti-Factor IIa assays. All chromogenic assays were quantified in a STA-R Analyzer (Diagnostica Stago) following Momenta Pharmaceuticals, Inc., SOP for anti-Factor Xa and anti-Factor IIa activity measurements. CBT was determined at 15 minutes, 60 minutes, and either 180 minutes or the time occlusion, if applicable. CBT assessment were carried out at a forelimb by Mielke method using the test facility's SOP.

Statistics

Values were reported as means±standard deviation (SD) unless otherwise noted. Means were compared using the Student's t-test assuming equal variance in different treatment groups. The incidence of occlusion was compared between treatment groups by calculating the odds ratio relative to control and using a z test to derive the P-value. Significance levels for all tests were set at 0.05.

Anti-Factor Xa and Anti-Factor IIa Plasma Activity

Figure 13:
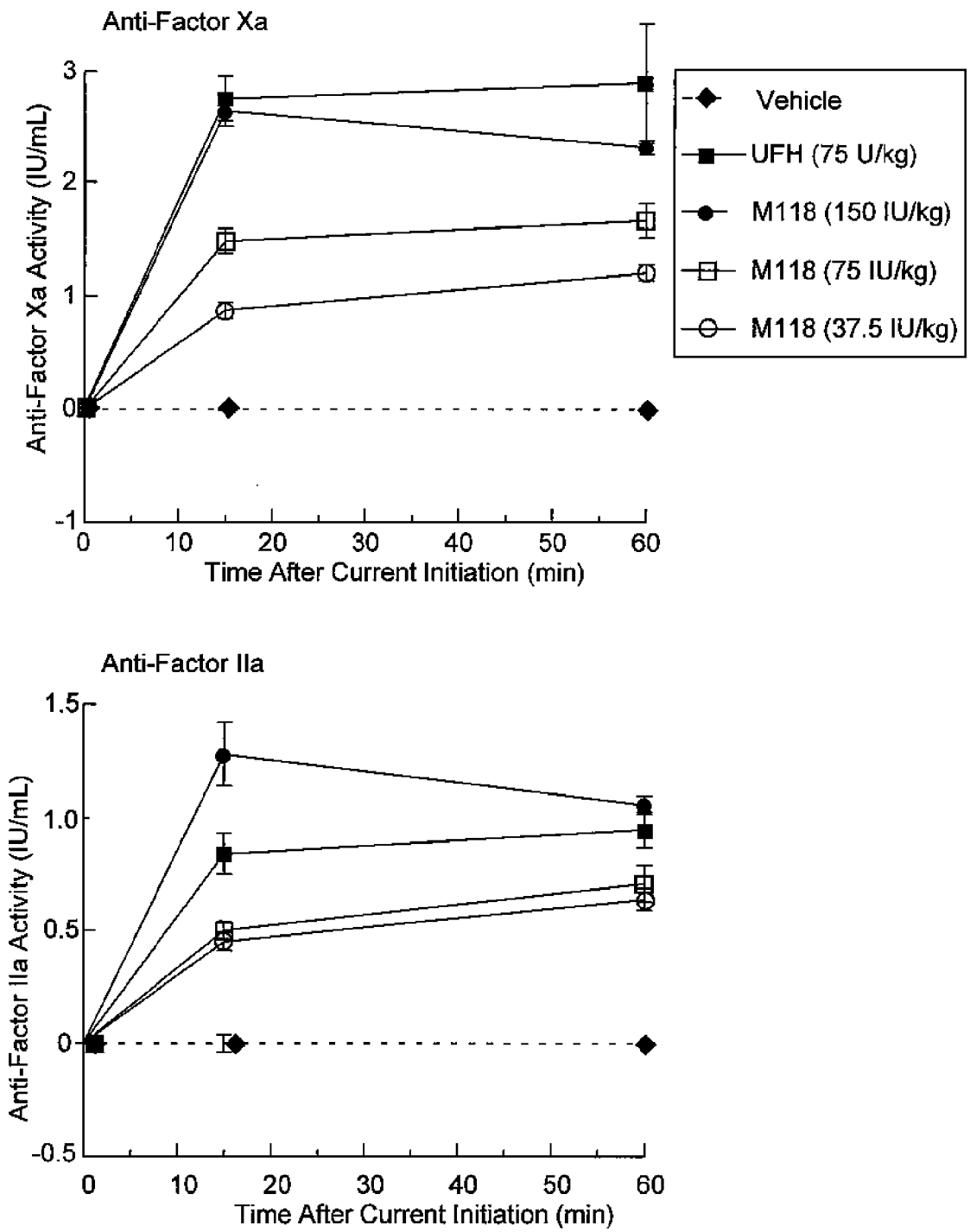
FIG. 13. Anti-Factor Xa activity (top) and anti-Factor IIa activity (bottom) vs. time in a canine model of deep arterial thrombosis (Lucchesi's model). The vehicle control group shown in the graphs subsequently received M118-REH at 150 IU/kg. Error bars are ±SE. UFH, unfractionated heparin.
Figure 14:
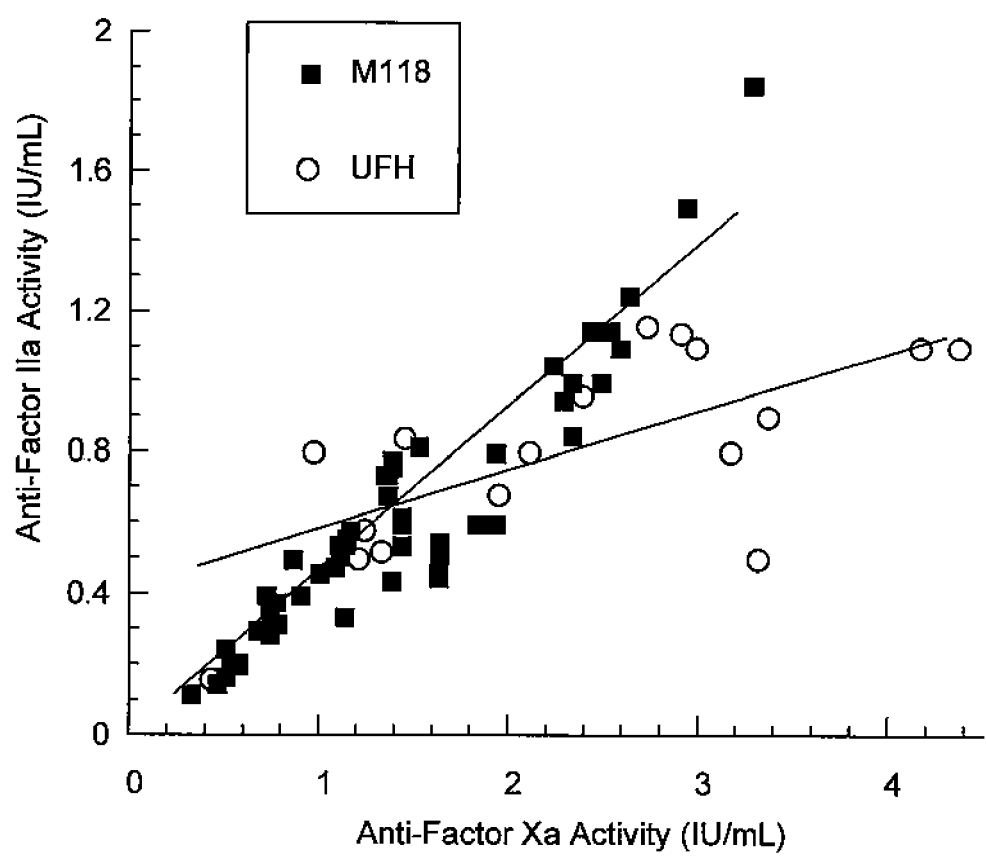
FIG. 14. Correlation of anti-Factor Xa and IIa activities in a canine model of deep arterial thrombosis (Lucchesi's model). Individual points represent data from a single animal. All animals in all treatment groups are shown. Correlation coefficients ($r^2$) were 0.890 and 0.465 in the M118-REH and unfractionated heparin (UFH) groups, respectively.
Figure 15:
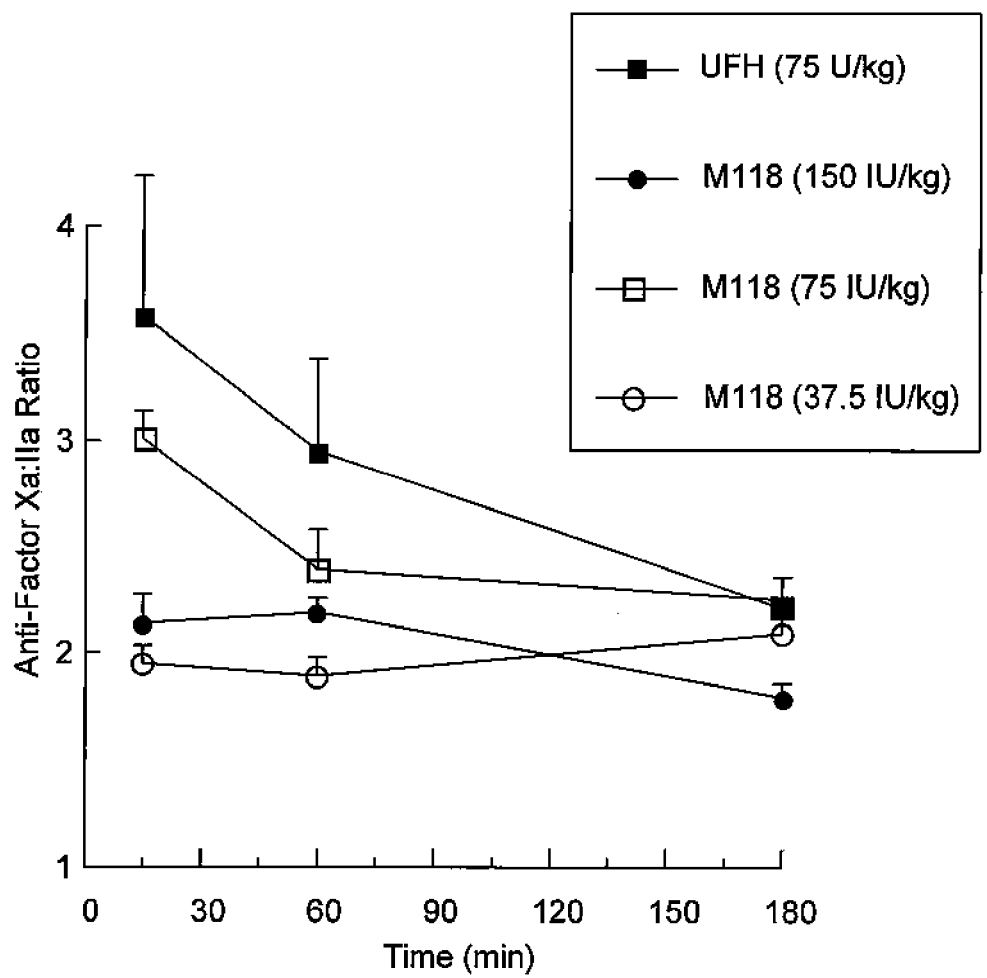
FIG. 15. Anti-Factor Xa:IIa ratio over time in a canine model of deep arterial thrombosis. Error bars are +SE (top halves only are shown to maximize clarity). UFH, unfractionated heparin.

Various doses of M118-REH were compared to a standard dose of UFH (75 U/kg). M118-REH exhibited dose-dependent inhibition of both Factor Xa and IIa, with the highest dose of M118-REH (150 IU/kg) demonstrating similar anti-Factor Xa activity relative to UFH (FIG. 13 and Table 16). Anti-Factor IIa activity increased proportionally with anti-Factor Xa activity for both M118-REH and UFH, although the correlation coefficient was greater for M118-REH ($r^2$=0.890) than UFH ($r^2$=0.465) (FIG. 14). Finally, the ratio of anti-Factor Xa activity to anti-Factor IIa plasma activity over time was generally more constant with M118-REH than UFH, consistent with the known variable metabolism of the large and polydisperse UFH molecules (FIG. 15).

TABLE 16

Summary of Selected Hematologic Endpoints

| Treatment | ACT (sec)* | Anti-Factor Xa (IU ± SD)* | Anti-Factor IIa (IU ± SD)* |
|---|---|---|---|
| Control | 69 ± 6 | 0.0 ± 0.0 | 0.0 ± 0.0 |
| M118-REH (37.5 IU/kg)† | 101 ± 7‡ | 1.20 ± 0.16 | 0.64 ± 0.12 |
| M118-REH (75 IU/kg)† | 108 ± 13‡ | 1.66 ± 0.37 | 0.71 ± 0.20 |
| M118-REH (150 IU/kg)† | 141 ± 28§ | 2.31 ± 0.13 | 1.06 ± 0.09 |
| UFH (75 U/kg)† | 163 ± 55‖ | 2.89 ± 1.31 | 0.95 ± 0.19 |

ACT, activated clotting time;
IU, international unit;
SD, standard deviation;
UFH, unfractionated heparin
*Recorded at 60 min after initiation of test article infusion;
†Bolus dose;
‡p < 0.05, M118-REH vs. UFH;
§p < 0.01, M118-REH vs. control;
‖p < 0.01, UFH vs. control.

Coagulation Assays

Figure 16:
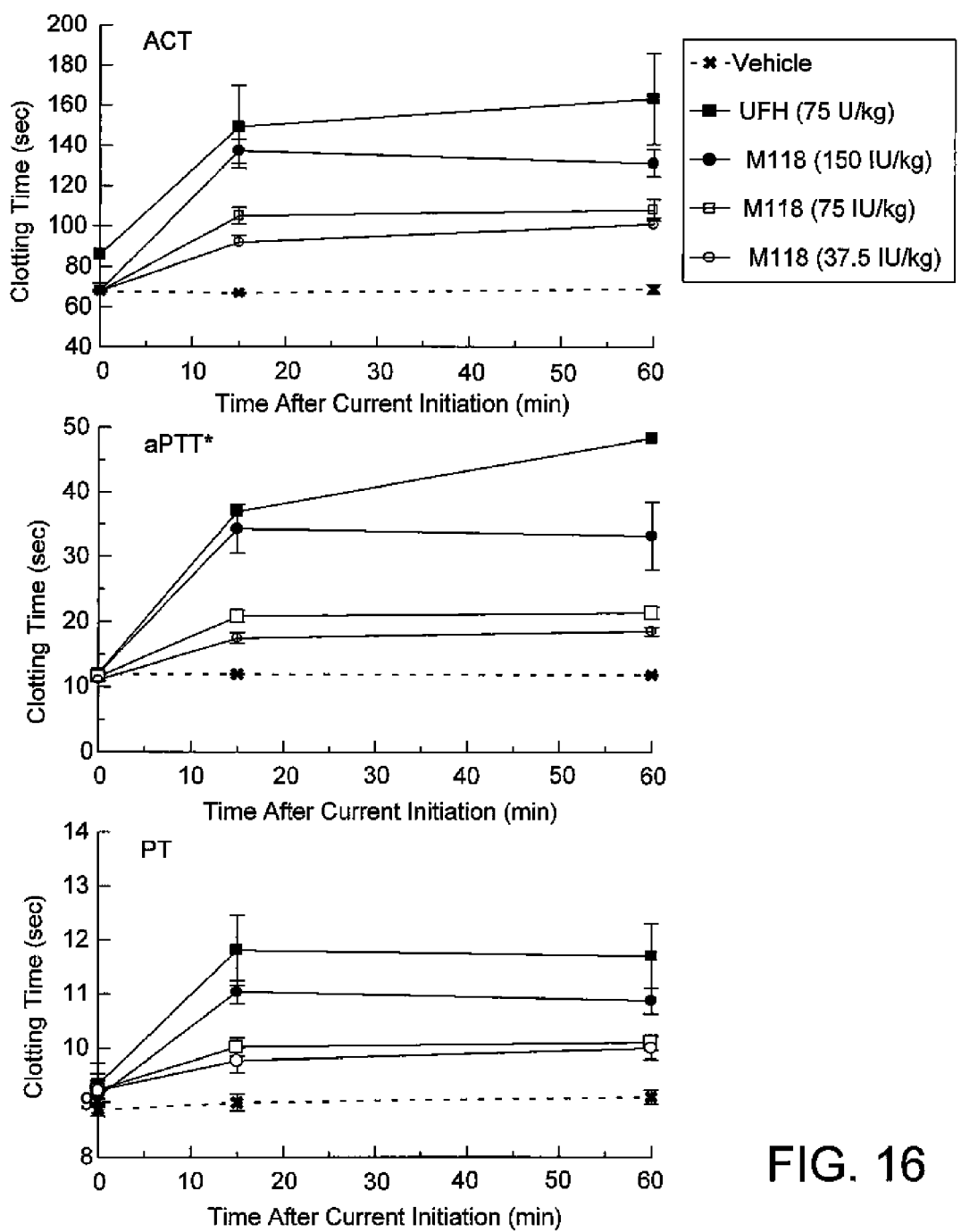
FIG. 16. Coagulation activity vs. time as assessed by ACT (top), aPTT (middle), and PT (bottom) assays in a canine model of deep arterial thrombosis. The vehicle control group shown in the graphs subsequently received M118-REH at 150 IU/kg. Error bars are ±SE. UFH, unfractionated heparin.

Next, the anti-coagulant activity of M118-REH was compared to a standard dose of UFH. M118-REH dose-dependent inhibition of clotting was observed within 15 minutes in all coagulation assays and was maintained during the course of the 60-minute observation period (FIG. 16). At 60 minutes, significantly longer clotting times in the ACT assay were observed after UFH treatment than M118-REH at 37.5 or 75 anti-Xa IU/kg (Table 16). The difference between UFH and M118-REH in the ACT assay was non-significant when M118-REH was administered at 150 anti-Xa IU/kg (Table 16). Control experiments demonstrated that differences between treatment groups in the coagulation assays were not attributable to alterations in the concentrations of the fibrinogen substrate (data not shown).

Antithrombotic Effects

Figure 17:
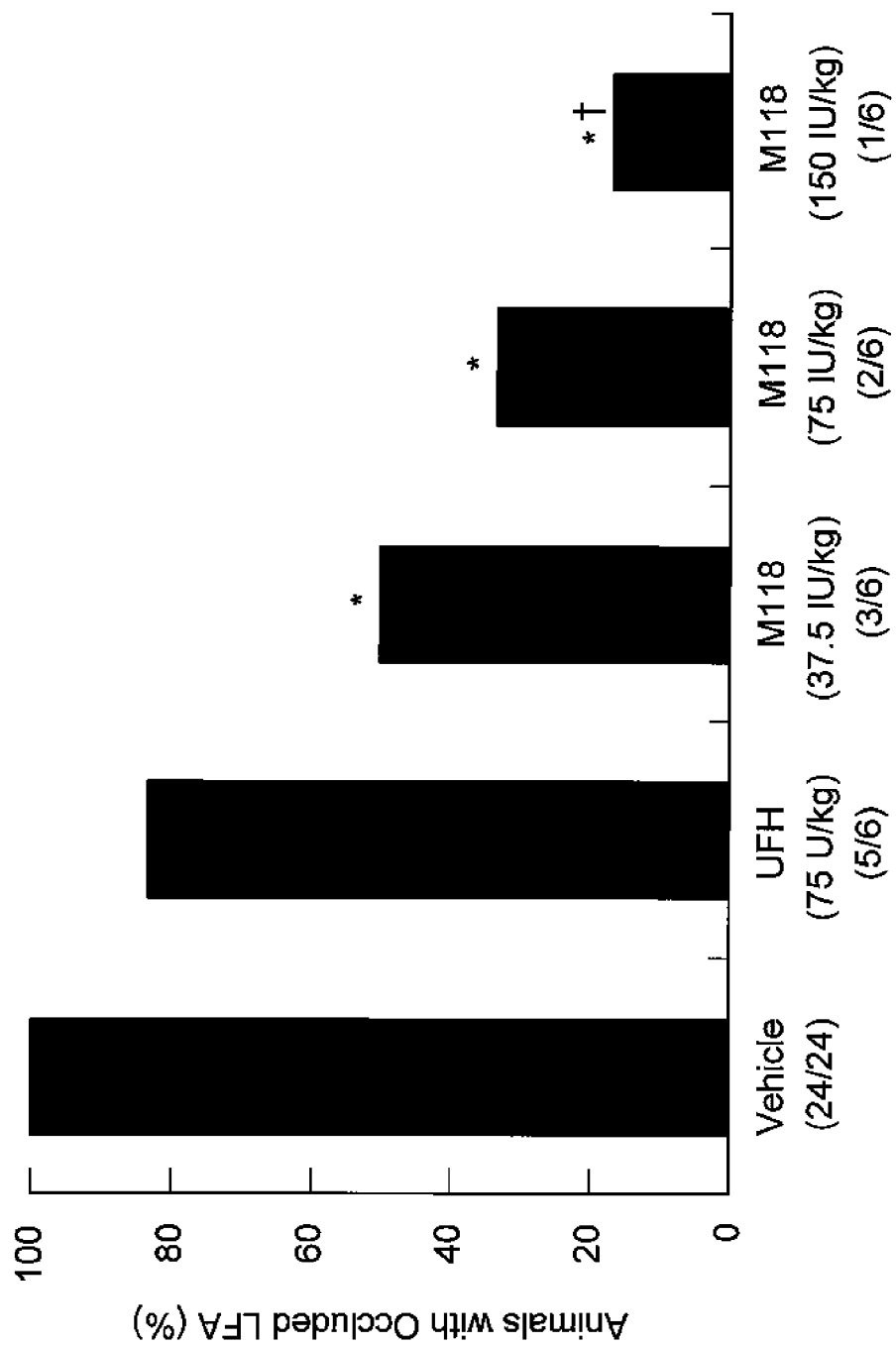
FIG. 17. Percentage of animals with occluded femoral arteries in a canine model of deep arterial thrombosis. Animals were monitored by Doppler flow for up to 180 minutes post current initiation. Occlusion was defined as blood flow through an injured artery that was ≤2% of baseline flow. UFH, unfractionated heparin.

Based on the observation that M118-REH at a dose of 150 anti-Xa IU/kg had similar anticoagulant properties to heparin at a standard dose of 75 U/kg, the antithrombotic efficacy of M118-REH at 150 anti-Xa IU/kg, as well as at lower doses, was compared to UFH in the canine model of deep arterial thrombosis. During infusion of vehicle, full occlusion of the control artery occurred in 24/24 [100%] animals within the observation period of 180 minutes (FIG. 17). In the UFH treatment group, 5/6 (83.3%) animals reached the model-defined decrease in Doppler flow. By comparison, full occlusion occurred in 3/6 (50%), 2/6 (33.3%), and 1/6 (16.7%) animals receiving M118-REH bolus doses of 37.5, 75, and 150 anti-Xa IU/kg, respectively, consistent with a dose-response relationship. The treatment differences between M118-REH- and vehicle-treated arteries for occlusion rates were statistically significant at all M118-REH bolus doses (P<0.05). The difference between M118-REH at a bolus dose of 150 anti-Xa IU/kg and UFH was also significant (P<0.05). Thus, M118-REH at 150 anti-Xa IU/kg showed superior efficacy to UFH at 75 U/kg, despite the fact that the anticoagulant activity of M118-REH and UFH were comparable at these doses. M118-REH at the lower tested doses (37.5 and 75 anti-Xa IU/kg), which were associated with lower anticoagulant activities, had antithrombotic effects that were more generally similar to UFH.

Mean times to occlusion were 59±25, 132±42, 165±23, 161±41, and 165±36 minutes in animals treated with vehicle, UFH, M118-REH (37.5 anti-Xa IU/kg), M118-REH (75 anti-Xa IU/kg), and M118-REH (150 anti-Xa IU/kg), respectively. It should be noted that mean occlusion times in the active-treated arteries were under-estimates of their true values, since many arteries, particularly in the M118-REH treatment groups, did not fully occlude by the prespecified endpoint of 180 minutes (such arteries were arbitrarily assigned an occlusion time of 180 minutes for the analysis). Mean thrombus weights were 24.0±9.15 mg in the vehicle-treated arteries, 19.4±9.47 mg in the UFH-treated arteries, and 24.5±12.17 mg, 19.8±6.24 mg, and 12.8±5.99 mg in the M118-REH-treated arteries at 37.5, 75, and 150 anti-Xa IU/kg, respectively. The differences between treatment groups for mean time to occlusion and mean thrombus weight did not reach statistical significance.

Cutaneous Bleeding Times

CBT varied from 80±15.5 to 160±52.5 seconds during vehicle administration at the protocol-specified time points in all groups (Table 17). UFH and M118-REH treatment resulted in minimal increases in CBT, and the effects were highly variable. Group means ranged from 135±90.5 to 275±306.8 seconds after UFH treatment and 110±36.3 to 190±86.3 seconds after M118-REH administration at all time points.

and 100 bpm targets pre-specified in the protocol. The maximum difference in mean arterial pressures and heart rate between the vehicle- and active-treated arteries in any given animal was 6 mm Hg and 5 beats per minute, respectively (P-values for differences were non-significant).

Summary

M118-REH at 150 anti-Xa IU/kg showed statistically superior antithrombotic efficacy to a standard dose of UFH (75 U/kg), despite the fact that M118-REH and UFH showed comparable activity in ACT, aPTT, and PT assays at these concentrations. Thus, the incidence of full thrombus-induced occlusion of the femoral artery was significantly lower in M118-REH-treated than UFH-treated animals (1/6 [16.7%] vs. 5/6 [83.3%], respectively; P<0.05).

The antithrombotic effects observed in the M118-REH treatment groups were achieved without evidence of complications. No instances of spontaneous bleeding were documented, and only minimal increases in CBT were observed at all M118-REH concentrations and experimental time points. Additionally, there were no unexpected mortalities or clinically meaningful changes in cardiovascular parameters and clinical chemistry.

Two features of the coagulation data in this study were noteworthy. First, M118-REH was measurable in a dose-dependent fashion by point-of-care ACT assays. Its ACT response was well correlated to anti-Factor Xa activity compared with UFH. This feature may simplify administration of LMWHs in interventional and surgical settings. Second, M118-REH exhibited not only in vitro anti-Factor Xa activity, but also significant anti-Factor IIa activity, a characteristic that further distinguishes M118-REH from currently avail-

TABLE 17

Cutaneous Bleeding Times

| Treatment | Baseline CBT (sec ± SD) | Femoral Artery | CBT (sec ± SD) | | |
|---|---|---|---|---|---|
| | | | 15 min | 60 min | 180 min |
| UFH (75 U/kg) | 100 ± 31.0 | Control | 125 ± 29.5 | 138 ± 45.5 | 100 ± 36.3 |
| | | Treated | 135 ± 90.5 | 145 ± 35.1 | 275 ± 306.8 |
| M118-REH (37.5 IU/kg) | 95 ± 35.1 | Control | 80 ± 15.5 | 130 ± 36.3 | 115 ± 58.2 |
| | | Treated | 145 ± 64.1 | 125 ± 48.1 | 110 ± 36.3 |
| M118-REH (75 IU/kg) | 140 ± 24.5 | Control | 130 ± 36.3 | 130 ± 17.3 | 160 ± 52.5 |
| | | Treated | 160 ± 45.2 | 190 ± 86.3 | 160 ± 31.0 |
| M118-REH (150 IU/kg) | 110 ± 41.0 | Control | 115 ± 51.7 | 110 ± 36.3 | 115 ± 48.1 |
| | | Treated | 150 ± 50.2 | 125 ± 64.1 | 135 ± 94.4 |

UFH, unfractionated heparin,
SD, standard deviation,
IU, international units,
U, units.

Hemodynamic Parameters

No clinically meaningful changes were observed in cardiovascular parameters or clinical chemistry during the course of the experiments. Across the study population, differences between poststenotic hyperemic responses at the vehicle- and active-treated arteries were ≤13 mL/min in all animals. The goal of limiting hypoxia-induced hyperemic response to ≤80% of the baseline response to physical occlusion was met in all but 2 arteries: 1 in which the response was 81% (M118-REH [75 anti-Xa IU/kg]; control artery); and 1 in which the response was 88% (M118-REH [75 anti-Xa IU/kg]; active treatment artery). Mean arterial pressure and heart rate during the course of the procedure in all treatment groups were 68-78 mm Hg and 96-111 bpm, respectively, close to the 70 mm Hg able LMWH options (J. Hirsh et al. "Heparin and low-molecular-weight heparin: mechanisms of action, pharmacokinetics, dosing, monitoring, efficacy, and safety," *Chest*. 2001; 119:64S-94S). Enoxaparin, for instance, is characterized by a ratio of anti-Factor Xa activity to IIa activity of 17.2; by comparison, the analogous ratio for UFH is 3.3 (U. Cornelli and J. Fareed. "Human pharmacokinetics of low molecular weight heparins," *Semin Thromb Hemost*. 1999; 25 Suppl 3:57-61). In this study, M118-REH had a ratio of anti-Factor Xa to IIa activity that was approximately 2-2.5 (FIG. 15), demonstrating enhanced anti-Factor IIa activity relative to other LMWHs. The ratio was generally more consistent over time than UFH, as predicted by the known variable metabolism of the large and polydisperse UFH molecules.

TABLE 18

Summary Table of Thrombotic and Selected Hematologic Endpoints

| Treatment | Occlusion (%) | Thrombus Weight (mg) | TTO (min)$^a$ | ACT (sec)$^b$ | Anti-Factor Xa$^b$ | Anti-Factor IIa$^b$ |
|---|---|---|---|---|---|---|
| Control (RFA) | 24/24 (100%) | 24.0 ± 9.2 | 59 ± 25 | 69 ± 6$^c$ | 0.00 ± 0.00 | 0.00 ± 0.00 |
| UFH (Grp 1) | 5/6 (83%) | 19.4 ± 9.5 | 132 ± 42$^e$ | 163 ± 55$^e$ | 2.89 ± 1.31 | 0.95 ± 0.19 |
| M118 (Grp 4) | 3/6 (50%)$^c$ | 24.5 ± 12.2 | 165 ± 23$^e$ | 101 ± 7$^d$ | 1.20 ± 0.16 | 0.64 ± 0.12 |
| M118 (Grp 2) | 2/6 (33%)$^c$ | 19.8 ± 6.2 | 161 ± 41$^e$ | 108 ± 13$^d$ | 1.66 ± 0.37 | 0.71 ± 0.20 |
| M118 (Grp 3) | 1/6 (17%)$^{c,d}$ | 12.8 ± 6.0$^e$ | 165 ± 36$^e$ | 131 ± 16 | 2.31 ± 0.13 | 1.06 ± 0.09 |

TTO = Time to occlusion;
ACT = Activated clotting time;
RFA = Right femoral artery;
UFH = unfractionated heparin;
Grp = Group.
$^a$TTO > 180 min was set at 180 min.
$^b$Value recorded at 60 min after initiation of test article infusion.
$^c$P < 0.05 vs. control.
$^d$P < 0.05 vs. UFH.
$^e$P < 0.01 vs. control.

In Vivo Neutralization:

In vivo studies were performed employing Sprague-Dawley rats and New Zealand rabbits. M118-REH, enoxaparin or two unfractionated heparins (UFH) were administered intravenously at different doses at t=0. Neutralization of the pharmacologic effects of each of these treatments were evaluated by tail vein injection of protamine sulfate 5 minutes after t0 at ratios of 0.5 and 1 mg to 100 anti-Xa IU (or 100 USP Unit or 1 mg in case of UFH). Blood samples were obtained and tested for anti-Xa and anti-IIa activity at baseline (just prior to protamine injection) 5, 30 and 60 minutes post-protamine sulfate administration.

Complete and rapid neutralization of M118-REH anti-Xa activity by protamine sulfate in vivo was achieved at ratios of 0.5 mg:100 anti-Xa IU (>98%) in rats and 1 mg:100 anti-Xa IU (more than 99% in rats and 95% in rabbits) at 5 minutes-post intravenous protamine sulfate delivery. There was no "rebound" of anti-Xa activity observed within 1 hour post protamine sulfate administration.

Figure 11:
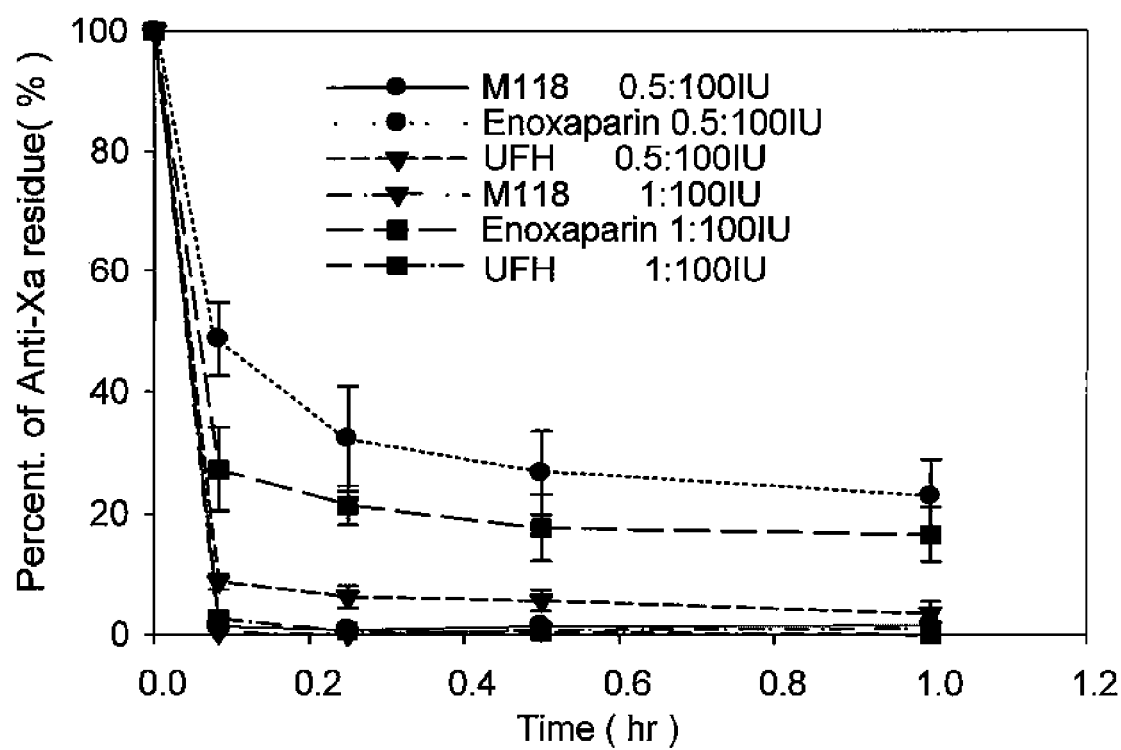
FIG. 11 is a graph depicting neutralization of anti-Xa activity of heparins in Sprague-Dawley rat model (M118-REH, enoxaparin sodium and UFH) by protamine sulfate. Graph was plotted with percent of remaining anti-Xa activity vs. time at ratios of 0.5 or 1 mg:100 anti-Xa IU of protamine to heparin (or 0.5 or 1 mg: 1 mg in case of UFH).

Neutralization of anti-Xa activity was comparable between M118-REH and UFH at ratios of 0.5 mg and 1 mg to 100 anti-Xa IU (or 100 USP or 1 mg UFH). Greater than 40% and 20% of the anti-Xa activity remained 5 minutes after protamine sulfate injection in rats dosed with enoxaparin at ratios of 0.5 and 1 mg:100 anti-Xa IU, respectively. Approximately 38% of the anti-Xa activity remained in rabbits administered enoxaparin at 1 mg: 100 anti-Xa IU protamine sulfate. More than 90% of the anti-IIa activity following each of the heparins was neutralized at ratios of 0.5 and 1 mg to 100 anti-Xa IU. The magnitude of reversal of anti-IIa activity by protamine sulfate was equivalent among the three treatments, i.e. M118-REH, enoxaparin or UFH. The results are depicted in FIG. 11.

In Cynomologus monkeys, protamine sulfate (PS) reversed both M118-REH anti-Xa and anti-IIa activity at a similar extent in a dose dependent fashion. M118-REH was administered intravenously to conscious cynomologus monkeys, in some cases followed by administration of PS. Blood samples were obtained and evaluated for M118-REH concentration as measured by anti-Xa and anti-IIa activity and coagulation profile. Hematology, cutaneous bleeding times and signs of clinical toxicity were monitored for 24 hours.

M118-REH activity was detectable immediately following iv administration at a dose of 150 anti-Xa IU/kg. First order elimination kinetics for M118-REH was observed with t1/2 of 0.50±0.04 hr (anti-Xa) and 0.68±0.05 hr (anti-IIa). Furthermore, PS rapidly reversed M118-REH anti-Xa and anti-IIa activity in a dose-dependent manner. The majority of anti-Xa (93.6±1.2%) and anti-IIa (90.14±1.2%) activity was rapidly neutralized by PS at a ratio of 1.5 mg PS per 100 IU anti-Xa activity, the higher dose studied. ACT and aPTT measurements closely correlated with anti-Xa activity (r2=0.95 and 0.99, respectively). M118-REH increased ACT 2-3 times and was reversed to baseline values within 5 minutes following intravenous PS administration. No signs of clinical toxicity or adverse bleeding were observed.

Administration of M118-REH causes a consistent and rapid anticoagulant affect that can be rapidly reversed by injection of PS. M118-REH anticoagulation is easily measured and monitored by ACT and aPTT. The reversibility and monitorability of M118-REH are unique compared with compared with other commercially available LMWHs.

The results of neutralization studies of M118-REH in the NHP model are presented in Tables 19-21 below.

TABLE 19

Neutralization of M118-REH in the NHP Model - Most aPTT and ACT Came Back to Normal After Dosing.

| | | UFH^ 1 mg:100 IU | M118-REH^ 1 mg:100 Anti-Xa IU | M118-REH^ 1.5 mg:100 Anti-Xa IU | M118-REH^ 2 mg:100 Anti-Xa IU |
|---|---|---|---|---|---|
| ACT | Baseline | 99.5 ± 9.2 | 85.3 ± 4.2 | 93.0 ± 5.1 | 97.0 ± 4.2 |
| | Post-M118-REH | 168.5 ± 14.9 | 174.3 ± 12.3 | 193.0 ± 9.7 | 139.0 ± 21.2 |
| | 5' Post Protamine | 97.5 ± 14.9 | 103.0 ± 4.4 (NS) | 99.2 ± 7.5 (NS) | 89.5 ± 0.7 (NS) |

TABLE 19-continued

Neutralization of M118-REH in the NHP Model - Most aPTT and ACT Came Back to Normal After Dosing.

| | | UFH^^ 1 mg:100 IU | M118-REH^ 1 mg:100 Anti-Xa IU | M118-REH^ 1.5 mg:100 Anti-Xa IU | M118-REH^^ 2 mg:100 Anti-Xa IU |
|---|---|---|---|---|---|
| aPTT | Baseline | 31.95 ± 0.1 | 23.4 ± 2.7 | 20.4 ± 0.9 | 26.1 ± 0.8 |
| | Post-M118-REH | 46.9 ± 31.9† | 177.9 ± 59.0* | 162.6 ± 85.5* | 48.1 ± 1.8 |
| | 5' Post Protamine | 24.2 ± 0.4 | 32.5 ± 4.4 | 29.6 ± 6.0 (NS) | 25.9 ± 1.6 (NS) |

NS: no significant difference compared to UFH
*aPTT > 212 sec in some samples;
†½ lower than baseline after UFH dosing
^M118-REH dosed at 150 IU/kg i.v.
^^M118-REH dosed at 75 IU/kg, UFH dosed at 75 IU/kg

TABLE 20

Neutralization of M118-REH in the NHP Model - Significant Anti-Xa/IIa Activities Remained

| | | UFH 1 mg: 100 IU | M118-REH 1 mg:100 anti-Xa IU | M118-REH 1.5 mg:100 anti-Xa IU | M118-REH 2 mg:100 anti-Xa IU |
|---|---|---|---|---|---|
| Anti-Xa | Baseline | 0.3 ± 0.4 | 0.0 ± 0.0 | 0.0 ± 0.0 | n/a |
| | Post-M118-REH | 2.0 ± 0.3 | 3.6 ± 0.4 | 6.1 ± 0.8 | 1.2 ± 0.1 |
| | 5' Post Protamine | 0.1 ± 0.1 | 0.5 ± 0.0 | 0.4 ± 0.1 | 0.2 ± 0.1 |
| Anti0-IIa | Baseline | 0.4 ± 0.4 | 0.0 ± 0.1 | 0.0 ± 0.0 | n/a |
| | Post-M118-REH | 1.9 ± 0.4 | 2.1 ± 0.3 | 3.0 ± 1.2 | 1.6 ± 0.0 |
| | 5' Post Protamine | 0.1 ± 0.1 | 0.3 ± 0.1 | 0.3 ± 0.1 | 0.4 ± 0.2 |

TABLE 21

Neutralization of M118-REH in the NHP Model - Percent of Reduction for Different Parameters After Protamine

| | UFH 1 mg:100 IU | M118-REH 1 mg:100 anti-Xa IU | M118-REH 1.5 mg:100 anti-Xa IU | M118-REH 2 mg::100 anti-Xa IU |
|---|---|---|---|---|
| ACT | 41.5 ± 14.0 | 40.8 ± 2.2 | 47.7 ± 1.2 | 34.9 ± 9.4 |
| aPTT | 32.4 ± 46.9 | 80.6 ± 5.4 | 74.8 ± 16.2 | 46.0 ± 16.9 |
| Anti-Xa | 97.3 ± 3.8 | 85.2 ± 2.0 | 93.6 ± 1.2 | 84.0 ± 9.1* |
| Anti-IIa | 97.2 ± 3.9 | 83.4 ± 4.2 | 90.1 ± 1.2 | 75.1 ± 10.1* |

†equation: (post-M118-REH − post-protamine) * 100/post-M118-REH
*assay instable

Figure 12:
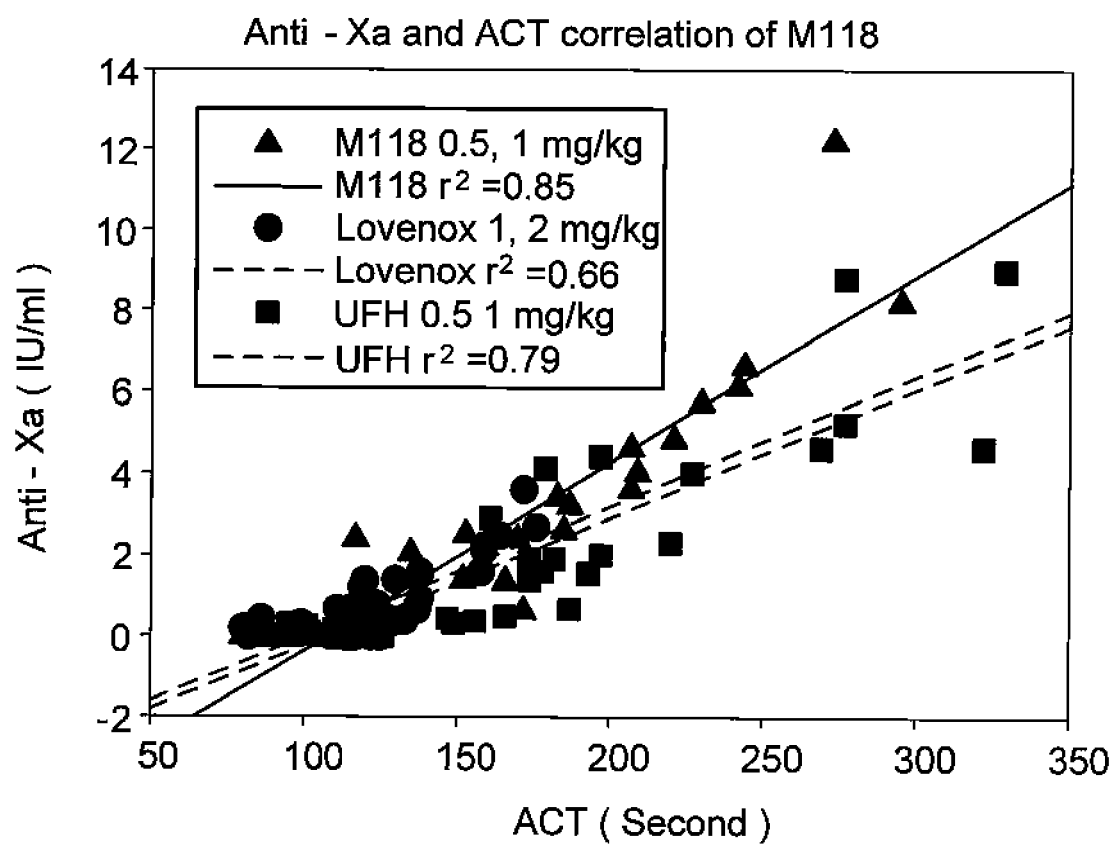
FIG. 12 is a graph depicting correlation of ACT measurement and anti-Xa activity of M118-REH (triangle and line), enoxaparin (open circle with dashed line) and UFH (square with dashed line). This data suggests that the M118-REH at the specified doses demonstrates the best correlation of ACT with anti-Xa activity when compared to enoxaparin or UFH ($r^2=0.85$).

In Vivo Bedside Monitoring Study in Preclinical Models:

M118-REH, enoxaparin and unfractionated heparin were administrated intravenously at different doses in rats or rabbits. Blood samples were obtained for ACT measurement and anti-Xa test. Hemachron Junior and ACT plus cuvette were used for ACT measurement while anti-Xa was measured with Coag-A-Mate MTX II. The correlation between anti-Xa and ACT was compared among these three heparins. In New Zealand White rabbits, 1 mg/kg M118-REH and UFH were injected via ear marginal vein. Blood samples were collected at 5', 15', 30' 1, 2, 3, 4 hrs after heparin delivery. In Sprague-Dawley rats, M118-REH and UFH were dosed at 0.5 and 1 mg/kg while enoxaparin dosed at 1 mg/kg and 2 mg/kg. Those doses achieved significant anti-Xa and ACT elevation both in rats and rabbits. For M118-REH, the correlation factor ($r^2$) of anti-Xa to ACT was 0.79 in rabbits and 0.85 in rats. The correlation factors ($r^2$) between anti-Xa and ACT for UFH were 0.31 in rabbits and 0.79 in rats, while for enoxaparin it was only 0.66 in rats. The results are show in FIG. 12.

In NHP models, after intravenous injection, M118-REH presented first order of elimination with half life as 0.50±0.04 or 0.68±0.05 hour by anti-Xa and anti-IIa measurement, respectively. Distribution volumes (Vd) are 32.01±2.21 (anti-Xa) or 48.58±0.95 mL/kg (anti-IIa) respectively. Clearance (Cl) are 37.24±4.65 (anti-Xa) and 43.92±5.38 (anti-IIa) mL/hr/kg. The ACT and aPTT results are closely correlated to anti-Xa activity (correlation ratio r=0.95 and 0.99 respectively).

In Vivo Hemorrhage Test:

Low molecular weight heparin is generated by depolymerization of unfractionated heparin with different chemical or enzymatic processes. Bleeding time measurements have been frequently employed in the development of new antithrombotics as an indication for risk of bleeding. This objective of this study was to investigate the risk of bleeding by standard bleeding time measurement for M118-REH and compare the risk to that posed by comparable treatments such as enoxaparin and unfractionated heparin.

M118-REH, enoxaparin and unfractionated heparin were administrated intravenously as a single bolus dose of 0.5 mg/kg via a marginal ear vein in rabbits. Bleeding time (BT) measurements were made on the ear at baseline and 5, 15, 30, 60, 120 and 180 minutes after test article administration. M118-REH caused a 3-4 fold increase in BT at 5 minutes compared to 60 minutes post-administration (p<0.05). A similar response in BT was observed by treatment with enoxaprin and UFH. Bleeding times returned to within normal range by 120 minutes and remained near baseline values for the remaining time points. No other adverse clinical findings were observed in any of treatment groups at the dose tested.

As shown in Table 22, in NHP models, M118-REH caused prolongation of Curtis bleeding time (CBT) after intravenous injection, there is no statistically significant difference from baseline (p<0.05).

TABLE 22

CBT of M118-REH after intravenous injection at 150 anti-Xa IU/kg in the NHP model.

| | Time point (hour) | | | |
|---|---|---|---|---|
| | 0 | 0.25 | 1 | 1.5 |
| Bleeding time (minutes) | 1.3 ± 0.6 | 2.5 ± 0.7 NS | 2.5 ± 1.0 NS | 2.5 ± 1.3 NS |

In beagles, UFH produced longer CBT than M118-REH after bolus injection and continuous infusion.

In Vivo Coagulation System:

Platelet Interaction:

In NHP models, there was no observation on the influence on platelet aggregation triggered by ADP after M118-REH bolus intravenous administration.

Fibrinolytic Pathway Intervention:

In NHP models, as shown in Table 18 below, after M118-REH intravenous bolus injection, fibrinogen level was consistent and there was no statistical significant difference from baseline.

TABLE 23

Fibrinogen and Prothrombin time (PT) after M118-REH intravenous injection at 150 anti-Xa IU/kg in the NHP model.

| | Fibrinogen (mg/dL) | Prothrombin Time (second) |
|---|---|---|
| baseline | 174.3 ± 35.0 | 11.4 ± 0.5 |
| 5' | 168.3 ± 28.0 | 16.0 ± 0.9** |
| 30' | 166.0 ± 30.5 | 13.8 ± 0.9* |
| 60' | 172.0 ± 29.7 | 14.1 ± 1.1* |
| 90' | 170.0 ± 27.9 | 12.8 ± 2.2 |
| 360' | 163.7 ± 29.5 | 11.4 ± 0.9 |
| 360' | 164.3 ± 27.0 | 10.8 ± 0.3 |
| 1440' | 176.0 ± 2.0 | 10.7 ± 0.3 |

Multiple Ascending Dose Studies

In repeat dose IV studies in the rat, increase in exposure to M118 appeared to be proportional to the increase in dosage on study Days 0 and 13. In male rats, exposure to M118 in terms of total anti-Xa activity increased from Day 0 to Day 13, but remained similar in terms of total anti-IIa activity. In female rats, exposure to M118 decreased from Day 0 to Day 13. Female rats appeared to have higher exposure to M118 than male rats on Day 0, but on Day 13 exposures to M118 were similar between genders. In repeat dose IV studies in the dog, systemic exposure to M118 increased as dosage increased over the 5 to 50 mg/kg/day range. However exposure to M118 generally did not increase proportionally with increasing M118. There was no evidence of accumulation over the 14 day period. Half-lives for anti-Xa and anti-IIa activity in dog plasma ranged from 1.0 to 3.2 hours with no particular trend related to dosage or gender. The half-lives tended to be shorter on Day 13 than on Day 0. There was no consistent trend related to M118 dosage with respect to the apparent systemic clearance or the apparent volume of distribution of anti-Xa and anti-IIa activities.

What is claimed is:

1. A low molecular weight heparin (LMWH) composition comprising:
oligosaccharide chains that have the following structure:

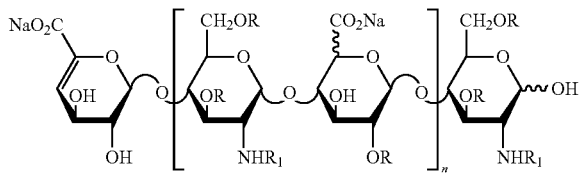

and oligosaccharide chains that have the following structure:

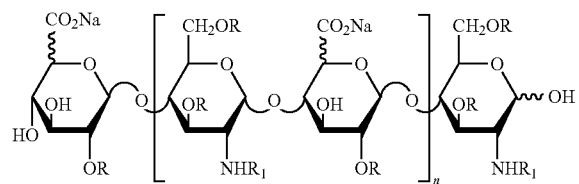

wherein
R is H or $SO_3Na$;
$R_1$ is $SO_3Na$ or $COCH_3$; and
n=2-50;
wherein the composition has the following properties:
(a) an average value for n of 9-16,
(b) 5 to 15% $\Delta UH_{NAc,6S}GH_{NS,3S,6S}$ as measured by mole %,
(c) weight average molecular weight of 5500 to 8500 Da,
(d) an anti-Xa activity of 170 to 330 IU/mg,
(e) an anti-Xa to anti-IIa ratio of 2:1 to 1:1,
(f) an anti-IIa activity of 130 to 190 IU/mg,
(g) a polydispersity in the range from 1.1 to 1.6, and
(h) the ratio of (e) is constant over a period of about 30 to 120 minutes after administration to a subject.

2. The LMWH composition of claim 1, wherein the weight average molecular weight of the compositions is 5700 to 7900 Da.

3. The LMWH composition of claim 1, wherein the anti-Xa activity is 180 to 300 IU/mg.

4. The LMWH composition of claim 1, wherein the anti-Xa activity is 200 to 300 IU/mg.

5. The LMWH composition of claim 1, wherein the anti-IIa activity is 155 to 195 IU/mg.

6. The LMWH composition of claim 1, wherein 15 to 35% of the total number of chains in the composition have a Δ4,5 unsulfated uronic acid at the non-reducing end.

7. The LMWH composition of claim 1, wherein at least 60% of the chains in the composition have an N-acetylated hexosamine at the reducing end.

8. The LMWH composition of claim 7, wherein at least 80% of the chains of the composition have an N-acetylated hexosamine at the reducing end.

9. The LMWH composition of claim 1, having less than 1000 ng/mg of a heparinase enzyme; less then 1% w/w methanol; less than 1% w/w ethanol; and less than 2000 ppm free sulfate.

10. The LMWH composition of claim 1, wherein the composition is lyophilized.

11. The LMWH composition of claim 1, wherein the composition is a liquid.

12. A pharmaceutical composition comprising the LMWH composition of claim 1, and a pharmaceutically acceptable carrier.

\* \* \* \* \*

UNITED STATES PATENT AND TRADEMARK OFFICE
CERTIFICATE OF CORRECTION

| | |
|---|---|
| PATENT NO. | : 8,609,632 B2 |
| APPLICATION NO. | : 11/805829 |
| DATED | : December 17, 2013 |
| INVENTOR(S) | : Shriver et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 300 days.

Signed and Sealed this
Twenty-first Day of April, 2015

Michelle K. Lee
*Director of the United States Patent and Trademark Office*